(12) United States Patent
Haddad et al.

(10) Patent No.: US 10,852,310 B2
(45) Date of Patent: Dec. 1, 2020

(54) FLUIDIC SYSTEMS INVOLVING INCUBATION OF SAMPLES AND/OR REAGENTS

(71) Applicant: OPKO Diagnostics, LLC, Woburn, MA (US)

(72) Inventors: Douglas M. Haddad, Amesbury, MA (US); Gary J. Fagan, Marblehead, MA (US); Yi Dong, Belmont, MA (US); Matthew Dirckx, Somerville, MA (US); Vincent Linder, Tewksbury, MA (US)

(73) Assignee: OPKO Diagnostics, LLC, Woburn, MA (US)

( * ) Notice: Subject to any disclaimer, the term of this patent is extended or adjusted under 35 U.S.C. 154(b) by 0 days.

(21) Appl. No.: 15/373,056

(22) Filed: Dec. 8, 2016

(65) Prior Publication Data

US 2017/0168077 A1   Jun. 15, 2017

Related U.S. Application Data

(60) Provisional application No. 62/266,488, filed on Dec. 11, 2015.

(51) Int. Cl.
*G01N 33/82* (2006.01)
*B01L 3/00* (2006.01)
(Continued)

(52) U.S. Cl.
CPC ........ *G01N 33/82* (2013.01); *B01L 3/502784* (2013.01); *G01N 33/54366* (2013.01);
(Continued)

(58) Field of Classification Search
CPC ............. G01N 33/82; G01N 33/54366; G01N 33/587; B01L 3/502784; B01L 3/502707
See application file for complete search history.

(56) References Cited

U.S. PATENT DOCUMENTS 3,735,640 A   3/1973   Chizhov et al.
4,318,994 A   3/1982   Meyer et al.
(Continued)

FOREIGN PATENT DOCUMENTS

EP    0 110 771 B1    3/1988
EP    0 643 307 A1    3/1995
(Continued)

OTHER PUBLICATIONS

International Search Report and Written Opinion for PCT/US2016/065633 dated Mar. 31, 2017.
(Continued)

*Primary Examiner* — Melanie Brown
(74) *Attorney, Agent, or Firm* — Wolf, Greenfield & Sacks, P.C.

(57) ABSTRACT

Fluidic devices and methods involving incubation and/or mixing of assay components are provided. In some embodiments, a biological and/or chemical assay may be performed in a fluidic device. The fluidic device may be designed to allow for controlled incubation and/or mixing of two or more assay components. In some such embodiments, the fluidic device may comprise an incubation channel having a relatively large cross-sectional dimension in fluid communication with a detection channel. The incubation channel may allow for adequate mixing and/or incubation of two or more assay components prior to analysis of the assay. In some embodiments, fluidic devices for performing a vitamin D assay are provided.

33 Claims, 17 Drawing Sheets

(51) Int. Cl.
  *G01N 33/543* (2006.01)
  *G01N 33/58* (2006.01)
(52) U.S. Cl.
  CPC ...... *G01N 33/587* (2013.01); *B01L 3/502707* (2013.01); *B01L 2300/0816* (2013.01); *B01L 2300/0867* (2013.01); *B01L 2300/0874* (2013.01); *B01L 2300/0883* (2013.01)

(56) References Cited

U.S. PATENT DOCUMENTS

| | | | |
|---|---|---|---|
| 4,517,302 | A | 5/1985 | Saros |
| 4,963,498 | A | 10/1990 | Hillman et al. |
| 5,051,237 | A | 9/1991 | Grenner et al. |
| 5,219,762 | A | 6/1993 | Katamine et al. |
| 5,268,147 | A | 12/1993 | Zabetakis et al. |
| 5,286,454 | A | 2/1994 | Nilsson et al. |
| 5,376,252 | A | 12/1994 | Ekström et al. |
| 5,478,751 | A | 12/1995 | Oosta et al. |
| 5,486,335 | A | 1/1996 | Wilding et al. |
| 5,571,410 | A | 11/1996 | Swedberg et al. |
| 5,635,358 | A | 6/1997 | Wilding et al. |
| 5,637,469 | A | 6/1997 | Wilding et al. |
| 5,726,026 | A | 3/1998 | Wilding et al. |
| 5,731,212 | A | 3/1998 | Gavin et al. |
| 5,866,345 | A | 2/1999 | Wilding et al. |
| 5,876,675 | A | 2/1999 | Kennedy |
| 5,942,443 | A | 8/1999 | Parce et al. |
| 5,955,028 | A | 9/1999 | Chow |
| 5,957,579 | A | 9/1999 | Kopf-Sill et al. |
| 6,019,944 | A | 2/2000 | Buechler |
| 6,042,709 | A | 3/2000 | Parce et al. |
| 6,046,056 | A | 4/2000 | Parce et al. |
| 6,103,199 | A | 8/2000 | Bjornson et al. |
| 6,136,272 | A | 10/2000 | Weigl et al. |
| 6,146,489 | A | 11/2000 | Wirth |
| 6,146,589 | A | 11/2000 | Chandler |
| 6,168,948 | B1 | 1/2001 | Anderson et al. |
| 6,176,962 | B1 | 1/2001 | Soane et al. |
| 6,184,029 | B1 | 2/2001 | Wilding et al. |
| 6,186,660 | B1 | 2/2001 | Kopf-Sill et al. |
| 6,207,369 | B1 | 3/2001 | Wohlstadter et al. |
| 6,214,560 | B1 | 4/2001 | Yguerabide et al. |
| 6,238,538 | B1 | 5/2001 | Parce et al. |
| 6,241,560 | B1 | 6/2001 | Furusawa et al. |
| 6,251,343 | B1 | 6/2001 | Dubrow et al. |
| 6,274,337 | B1 | 8/2001 | Parce et al. |
| 6,296,020 | B1 | 10/2001 | McNeely et al. |
| 6,331,439 | B1 | 12/2001 | Cherukuri et al. |
| 6,333,200 | B1 | 12/2001 | Kaler et al. |
| 6,361,958 | B1 | 3/2002 | Shieh et al. |
| 6,413,782 | B1 | 7/2002 | Parce et al. |
| 6,416,642 | B1 | 7/2002 | Alajoki et al. |
| 6,429,025 | B1 | 8/2002 | Parce et al. |
| 6,432,720 | B2 | 8/2002 | Chow |
| 6,479,299 | B1 | 11/2002 | Parce et al. |
| 6,488,872 | B1 | 12/2002 | Beebe et al. |
| 6,488,894 | B1 | 12/2002 | Miethe et al. |
| 6,488,896 | B2 | 12/2002 | Weigl et al. |
| 6,551,841 | B1 | 4/2003 | Wilding et al. |
| 6,610,499 | B1 | 8/2003 | Fulwyler et al. |
| 6,613,512 | B1 | 9/2003 | Kopf-Sill et al. |
| 6,613,525 | B2 | 9/2003 | Nelson et al. |
| 6,620,625 | B2 | 9/2003 | Wolk et al. |
| 6,632,619 | B1 | 10/2003 | Harrison et al. |
| 6,638,482 | B1 | 10/2003 | Ackley et al. |
| 6,656,430 | B2 | 12/2003 | Sheppard, Jr. et al. |
| 6,669,831 | B2 | 12/2003 | Chow et al. |
| 6,705,357 | B2 | 3/2004 | Jeon et al. |
| 6,709,869 | B2 | 3/2004 | Mian et al. |
| 6,716,620 | B2 | 4/2004 | Bashir et al. |
| 6,742,661 | B1 | 6/2004 | Schulte et al. |
| 6,761,962 | B2 | 7/2004 | Bentsen et al. |
| 6,780,584 | B1 | 8/2004 | Edman et al. |
| 6,794,197 | B1 | 9/2004 | Indermuhle et al. |
| 6,818,184 | B2 | 11/2004 | Fulwyler et al. |
| 6,827,095 | B2 | 12/2004 | O'Connor et al. |
| 6,828,143 | B1 | 12/2004 | Bard |
| 6,830,936 | B2 | 12/2004 | Anderson et al. |
| 6,858,185 | B1 | 2/2005 | Kopf-Sill et al. |
| 6,875,403 | B2 | 4/2005 | Liu et al. |
| 6,878,271 | B2 | 4/2005 | Gilbert et al. |
| 6,878,755 | B2 | 4/2005 | Singh et al. |
| 6,949,377 | B2 | 9/2005 | Ho |
| 6,953,550 | B2 | 10/2005 | Sheppard, Jr. et al. |
| 6,989,128 | B2 | 1/2006 | Alajoki et al. |
| 7,005,292 | B2 | 2/2006 | Wilding et al. |
| 7,015,046 | B2 | 3/2006 | Wohlstadter et al. |
| 7,018,830 | B2 | 3/2006 | Wilding et al. |
| 7,067,263 | B2 | 6/2006 | Parce et al. |
| 7,087,148 | B1 | 8/2006 | Blackburn et al. |
| 7,087,395 | B1 | 8/2006 | Garrity et al. |
| 7,091,048 | B2 | 8/2006 | Parce et al. |
| 7,482,162 | B2 | 1/2009 | Laurie et al. |
| 7,611,616 | B2 | 11/2009 | Cohen et al. |
| 7,736,890 | B2 | 6/2010 | Sia et al. |
| 7,964,363 | B2 | 6/2011 | Armbruster et al. |
| D645,971 | S | 9/2011 | Taylor et al. |
| 8,030,057 | B2 | 10/2011 | Linder et al. |
| 8,202,492 | B2 | 6/2012 | Linder et al. |
| 8,221,700 | B2 | 7/2012 | Steinmiller et al. |
| 8,222,049 | B2 | 7/2012 | Linder et al. |
| 8,389,272 | B2 | 3/2013 | Linder et al. |
| 8,409,527 | B2 | 4/2013 | Linder et al. |
| 8,475,737 | B2 | 7/2013 | Linder et al. |
| 8,480,975 | B2 | 7/2013 | Steinmiller et al. |
| 8,501,416 | B2 | 8/2013 | Linder |
| 8,567,425 | B2 | 10/2013 | Tan et al. |
| 8,574,924 | B2 | 11/2013 | Sia et al. |
| 8,580,569 | B2 | 11/2013 | Linder et al. |
| 8,591,829 | B2 | 11/2013 | Taylor et al. |
| 8,765,062 | B2 | 7/2014 | Linder et al. |
| 8,802,029 | B2 | 8/2014 | Steinmiller et al. |
| 8,802,445 | B2 | 8/2014 | Linder et al. |
| 8,915,259 | B2 | 12/2014 | Tan et al. |
| 8,932,523 | B2 | 1/2015 | Linder et al. |
| 9,075,047 | B2 | 7/2015 | Linder et al. |
| 9,075,051 | B2 | 7/2015 | Tan et al. |
| 9,116,124 | B2 | 8/2015 | Linder et al. |
| 9,116,148 | B2 | 8/2015 | Linder et al. |
| 9,181,292 | B2 | 11/2015 | Liang |
| 9,234,888 | B2 | 1/2016 | Linder et al. |
| 9,244,083 | B2 | 1/2016 | Teng et al. |
| 9,255,866 | B2 | 2/2016 | Dirckx et al. |
| 9,555,408 | B2 | 1/2017 | Tan et al. |
| 9,561,506 | B2 | 2/2017 | Taylor et al. |
| 9,588,027 | B2 | 3/2017 | Dirckx et al. |
| 9,592,505 | B2 | 3/2017 | Linder et al. |
| 9,643,182 | B2 | 5/2017 | Linder et al. |
| 9,672,329 | B2 | 6/2017 | Vickers et al. |
| 9,682,376 | B2 | 6/2017 | Linder et al. |
| 9,683,993 | B2 | 6/2017 | Linder et al. |
| 9,731,291 | B2 | 8/2017 | Tan et al. |
| 9,770,715 | B2 | 9/2017 | Steinmiller et al. |
| 9,795,697 | B2 | 10/2017 | Linder et al. |
| 2002/0001818 | A1 | 1/2002 | Brock |
| 2002/0019059 | A1 | 2/2002 | Chow et al. |
| 2002/0071788 | A1 | 6/2002 | Fujii et al. |
| 2002/0092767 | A1 | 7/2002 | Bjornson et al. |
| 2002/0142618 | A1 | 10/2002 | Parce et al. |
| 2002/0199094 | A1 | 12/2002 | Strand et al. |
| 2003/0012697 | A1 | 1/2003 | Hahn et al. |
| 2003/0082081 | A1 | 5/2003 | Yves et al. |
| 2003/0118486 | A1 | 6/2003 | Zhou et al. |
| 2003/0124623 | A1 | 7/2003 | Yager et al. |
| 2003/0138969 | A1 | 7/2003 | Jakobsen et al. |
| 2003/0207328 | A1 | 11/2003 | Yguerabide et al. |
| 2004/0077074 | A1 | 4/2004 | Ackley et al. |
| 2004/0115094 | A1 | 6/2004 | Gumbrecht et al. |
| 2004/0132104 | A1 | 7/2004 | Sackrison et al. |
| 2004/0228771 | A1 | 11/2004 | Zhou et al. |
| 2005/0118073 | A1 | 6/2005 | Facer et al. |
| 2005/0161669 | A1 | 7/2005 | Jovanovich et al. |
| 2005/0221281 | A1 | 10/2005 | Ho |

(56) References Cited

U.S. PATENT DOCUMENTS

| | | |
|---|---|---|
| 2005/0238545 A1 | 10/2005 | Parce et al. |
| 2005/0255003 A1 | 11/2005 | Summersgill et al. |
| 2006/0002827 A1 | 1/2006 | Curcio et al. |
| 2006/0078929 A1 | 4/2006 | Bickel et al. |
| 2006/0094119 A1 | 5/2006 | Ismagilov et al. |
| 2006/0257992 A1 | 11/2006 | McDevitt et al. |
| 2006/0275852 A1 | 12/2006 | Montagu |
| 2007/0031283 A1* | 2/2007 | Davis ............... A61B 5/14546 422/400 |
| 2007/0048189 A1 | 3/2007 | Cox et al. |
| 2007/0298433 A1 | 12/2007 | Sia et al. |
| 2008/0085219 A1 | 4/2008 | Beebe et al. |
| 2008/0248590 A1 | 10/2008 | Gulliksen et al. |
| 2008/0273918 A1* | 11/2008 | Linder ................. B01L 3/5027 403/31 |
| 2009/0023201 A1 | 1/2009 | Hongo et al. |
| 2010/0009430 A1* | 1/2010 | Wan ................. B01L 3/502746 435/287.1 |
| 2010/0068725 A1 | 3/2010 | Armbruster et al. |
| 2010/0285603 A1 | 11/2010 | Kobold et al. |
| 2012/0178091 A1* | 7/2012 | Glezer ................. B01L 3/5027 435/6.12 |
| 2014/0134603 A1 | 5/2014 | Sia et al. |
| 2014/0147935 A1 | 5/2014 | Imus Swinkels et al. |
| 2014/0248707 A1 | 9/2014 | Antoni et al. |
| 2014/0342350 A1 | 11/2014 | Dirckx et al. |
| 2015/0087079 A1* | 3/2015 | Coffey ............. G01N 33/54366 436/501 |
| 2015/0118689 A1 | 4/2015 | Egan et al. |
| 2015/0212099 A1 | 7/2015 | Yuan et al. |
| 2015/0233901 A1 | 8/2015 | Linder et al. |
| 2015/0343443 A1 | 12/2015 | Linder et al. |
| 2015/0355202 A1* | 12/2015 | Uchida ................. G01N 33/82 436/131 |
| 2016/0025732 A1 | 1/2016 | Linder et al. |
| 2016/0054343 A1* | 2/2016 | Holmes ................ G01N 35/026 506/2 |
| 2016/0077087 A1 | 3/2016 | Linder et al. |
| 2016/0202276 A1 | 7/2016 | Meunier et al. |
| 2016/0207042 A1 | 7/2016 | Dirckx et al. |
| 2016/0229881 A1 | 8/2016 | Liang |
| 2016/0282349 A1 | 9/2016 | Linder et al. |
| 2016/0305878 A1 | 10/2016 | Steinmiller et al. |
| 2016/0305937 A1 | 10/2016 | Steinmiller et al. |
| 2016/0305938 A1 | 10/2016 | Linder et al. |
| 2016/0320394 A1 | 11/2016 | Dong et al. |
| 2017/0045507 A1* | 2/2017 | Khattak ........... G01N 33/54366 |
| 2017/0089904 A1 | 3/2017 | Dong et al. |
| 2017/0091379 A1 | 3/2017 | Vickers et al. |
| 2017/0091380 A1 | 3/2017 | Vickers et al. |
| 2017/0165661 A1 | 6/2017 | Taylor et al. |
| 2017/0165664 A1 | 6/2017 | Tan et al. |
| 2017/0165665 A1 | 6/2017 | Linder et al. |
| 2017/0167958 A1 | 6/2017 | Dirckx et al. |
| 2017/0168060 A1 | 6/2017 | Vickers et al. |
| 2017/0184572 A1 | 6/2017 | Seo et al. |
| 2017/0238857 A1 | 8/2017 | Taylor et al. |
| 2017/0239656 A1 | 8/2017 | Linder et al. |

FOREIGN PATENT DOCUMENTS

| | | |
|---|---|---|
| EP | 1 054 259 A1 | 11/2000 |
| EP | 1 946 830 A1 | 7/2008 |
| EP | 2 071 026 A1 | 6/2009 |
| WO | WO 91/01003 A | 1/1991 |
| WO | WO 02/22250 A2 | 3/2002 |
| WO | WO 03/054513 A2 | 7/2003 |
| WO | WO 2005/056186 A1 | 6/2005 |
| WO | WO 2005/072858 A1 | 8/2005 |
| WO | WO 2006/018044 A1 | 2/2006 |
| WO | WO 2006/056787 A1 | 6/2006 |
| WO | WO 2006/113727 A2 | 10/2006 |
| WO | WO 2008/118098 A1 | 10/2008 |

OTHER PUBLICATIONS

Extended European Search Report for EP App. No. 16873848.2 dated Jul. 26, 2019.

* cited by examiner

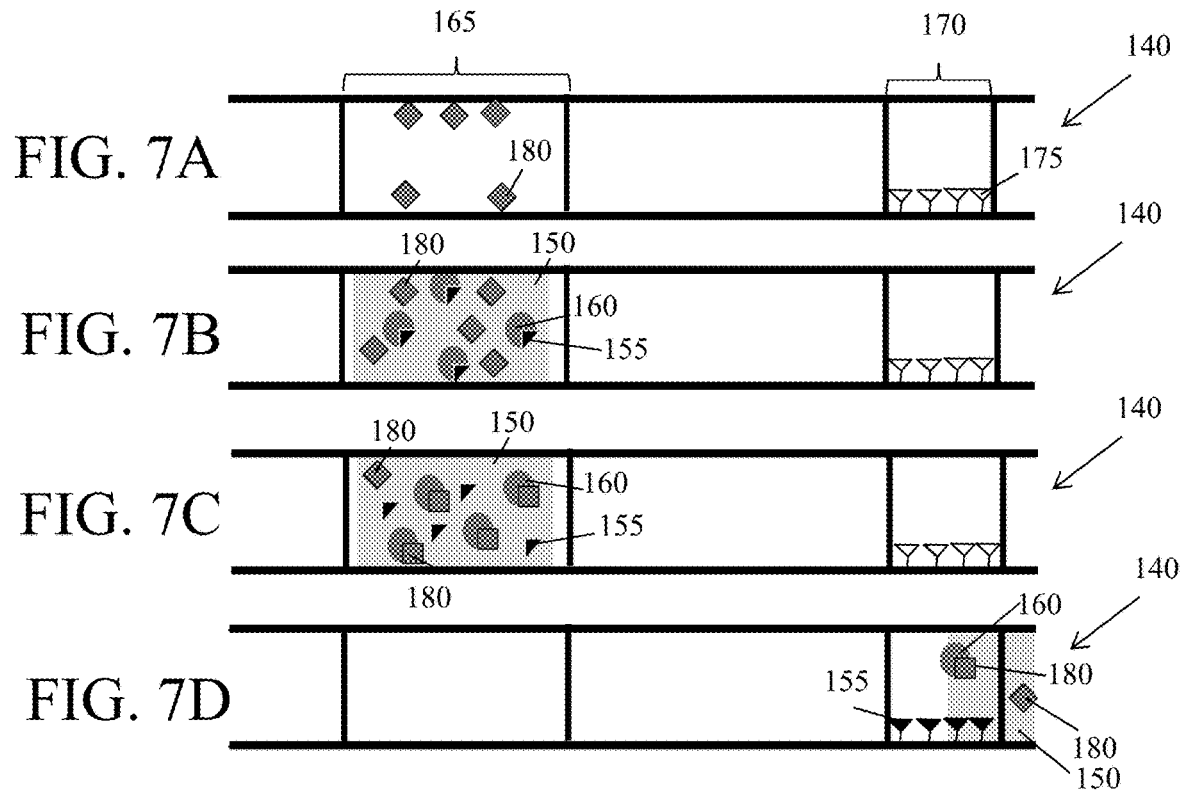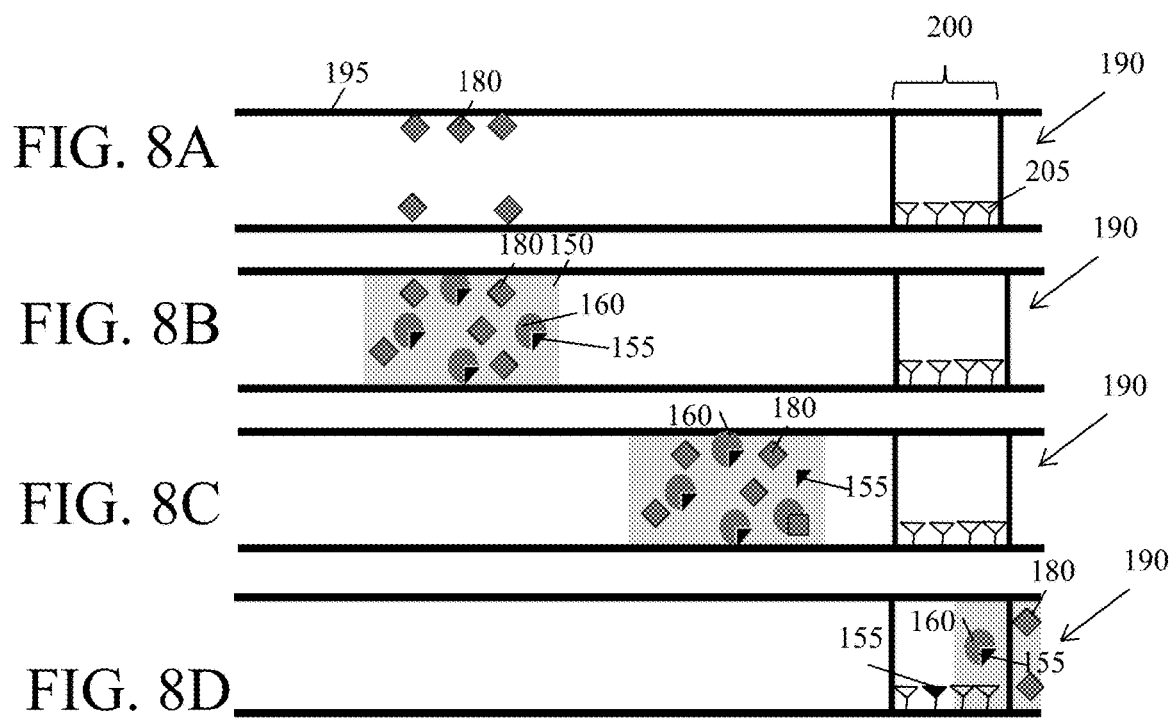

FLUIDIC SYSTEMS INVOLVING INCUBATION OF SAMPLES AND/OR REAGENTS

RELATED APPLICATIONS

This application claims the benefit of U.S. Provisional Patent Application Ser. No. 62/266,488, filed Dec. 11, 2015 entitled "FLUIDIC SYSTEMS INVOLVING INCUBATION OF SAMPLES AND/OR REAGENTS", which is incorporated herein by reference in its entirety for all purposes.

FIELD OF INVENTION

The present embodiments relate generally to systems and methods for flowing fluids in fluidic devices, and more specifically, to systems and methods that involve the incubation and/or mixing of fluids.

BACKGROUND

The manipulation of fluids plays an important role in fields such as chemistry, microbiology, and biochemistry. These fluids may include liquids or gases and may provide reagents, solvents, reactants, or rinses to chemical or biological processes. While various fluidic (e.g., microfluidic) methods and devices, such as microfluidic assays, can provide inexpensive, sensitive and accurate analytical platforms, fluid manipulations—such as the mixture of multiple fluids, sample introduction, introduction of reagents, storage of reagents, separation of fluids, collection of waste, extraction of fluids for off-chip analysis, and transfer of fluids from one chip to the next—can add a level of cost and sophistication. Accordingly, advances in the field that could reduce costs, simplify use, and/or improve fluid manipulations in microfluidic systems would be beneficial.

SUMMARY OF THE INVENTION

Methods for flowing fluids in fluidic devices, and related components, devices and systems associated therewith are provided. The subject matter of this application involves, in some cases, interrelated methods, alternative solutions to a particular problem, and/or a plurality of different uses of fluids and devices.

In one set of embodiments, a fluidic device for determining an amount of vitamin D in a sample is provided. The fluidic device comprises a release agent contained in at least one fluidic channel, wherein the release agent is adapted and arranged to release a vitamin D molecule from a vitamin D binding protein (VDBP). The fluidic device also comprises an anti-vit-D antibody and/or fragments thereof and/or exogenous vitamin D contained in at least one fluidic channel, wherein at least one fluidic channel of the fluidic device is a microfluidic channel. The fluidic device includes a detection zone for determining an amount of vitamin D in a sample.

In one set of embodiments, a series of methods are provided. In one set of embodiments, a method comprises introducing a sample into a fluidic device comprising at least one microfluidic channel, wherein the sample comprises vitamin D bound to a vitamin D binding protein. The method involves exposing the sample to a release agent, releasing the vitamin D from the vitamin D binding protein, and determining an amount of vitamin D in the sample.

In some embodiments, a method, comprises introducing a sample comprising a sample component into a sample collector, and connecting the sample connector to a sample inlet port of an article, wherein the article comprises first and second sides, wherein the first side comprises an incubation channel, and wherein the first side and/or second side comprises a detection channel in fluid communication with the incubation channel, and wherein the sample inlet port is in fluid communication with the incubation channel. The method involves flowing, at a first flow rate, at least a portion of the sample from the sample collector to the incubation channel, flowing at least a portion of the sample into a part, but not all, of the detection channel, and reducing the flow rate of the sample to a second flow rate, wherein the second flow rate is less than the first flow rate and/or is zero. The method also involves modulating the flow rate of the sample to a third flow rate which is greater than or less than the second flow rate, and flowing the sample through remaining parts of the detection channel.

In another embodiment, a method comprises flowing, at a first flow rate, at least a portion of the sample from the sample collector to the incubation channel; flowing at least a portion of the sample into a part, but not all, of the detection channel, detecting at least a portion of the sample at the detection channel; reducing the flow rate of the sample to a second flow rate, wherein the second flow rate is less than the first flow rate and/or is zero; modulating the flow rate of the sample, wherein the third flow rate may be greater than or less than the first or second flow rate; and flowing the sample through remaining parts of the detection channel.

In some embodiments, a method comprises introducing a sample comprising a sample component into a sample collector and connecting the sample connector to a sample inlet port of an article, wherein the article comprises first and second sides, wherein the first side comprises an incubation channel, wherein the first side and/or second side comprises a detection channel in fluid communication with the incubation channel, and wherein the sample inlet port is in fluid communication with the incubation channel. The method may further comprise flowing, at a first flow rate, at least a portion of the sample from the sample collector to the incubation channel; flowing at least a portion of the sample into a part, but not all, of the detection channel, detecting at least a portion of the sample at the detection channel; reducing the flow rate of the sample to a second flow rate, wherein the second flow rate is less than the first flow rate and/or is zero; and flowing the sample through remaining parts of the detection channel.

In another embodiment, a method comprises introducing a sample comprising a sample component into a sample collector and connecting the sample connector to a sample inlet port of an article, wherein the article comprises first and second sides, wherein the first side comprises an incubation channel, and wherein the first side and/or second side comprises a detection channel in fluid communication with the incubation channel, and wherein the sample inlet port is in fluid communication with the incubation channel. The method may further comprise contacting a liquid with a reagent deposited on a surface of the sample collector or a surface of the article and removing at least a portion of the reagent from the surface such that the reagent is dissolved or suspended in the liquid; mixing the sample component with the reagent in at least a portion of the liquid in the incubation channel; and flowing the liquid comprising the sample component and the reagent through at least a portion of the detection channel.

In one embodiment, a method comprises introducing a sample comprising a sample component into a sample collector and connecting the sample connector to a sample inlet port of an article, wherein the article comprises first and second sides, wherein the first side comprises an incubation channel, and wherein the first side and/or second side comprises a detection channel in fluid communication with the incubation channel, and wherein the sample inlet port is in fluid communication with the incubation channel. In such cases, the incubation channel has a width of at least about 100 microns and less than or equal to about 2 mm, a height of at least about 50 microns and less than or equal to about 2 mm, and a volume of at least 5 µL. The detection channel has a width of at least about 50 microns and less than or equal to about 300 microns, and a height of at least about 10 microns and less than or equal to about 300 microns and the detection channel comprises a reagent deposited on a surface of the detection channel. The method may further comprise flowing at least a portion of the sample from the sample collector to the incubation channel; mixing the sample component with a reagent in a liquid in the incubation channel; and flowing the liquid comprising the sample component and the reagent through at least a portion of the detection channel.

In another set of embodiments, fluidic systems are provided. In one embodiment, a fluidic system comprises an article comprising first and second sides, wherein the first side comprises an incubation channel, wherein the first side and/or second side comprises a detection channel, and wherein a first intervening channel passes through the article and is positioned between the incubation channel and the detection channel. The incubation channel has a width of at least about 100 microns and less than or equal to about 2 mm, a height of at least about 50 microns and less than or equal to about 2 mm, and a volume of at least 5 µL. The detection channel has a width of at least about 50 microns and less than or equal to about 300 microns, and a height of at least about 10 microns and less than or equal to about 300 microns, and the detection channel comprising a reagent deposited on a surface of the detection channel. In such cases, a ratio of heights of the incubation channel to the detection channel is at least 2:1. The fluidic system may further comprise a sample inlet port in fluid communication with the incubation channel and an outlet port in fluid communication with the detection channel.

In another embodiment, a fluidic system comprises an article comprising first and second sides, wherein the first side comprises an incubation channel, and wherein the first side and/or second side comprises a detection channel in fluid communication with the incubation channel. The incubation channel has a width of at least about 100 microns and less than or equal to about 2 mm, a height of at least about 50 microns and less than or equal to about 2 mm, and a volume of at least 5 µL. The detection channel has a width of at least about 50 microns and less than or equal to about 300 microns, and a height of at least about 10 microns and less than or equal to about 300 microns, and the detection channel comprising a reagent deposited on a surface of the detection channel. In such cases, a ratio of heights of the incubation channel to the detection channel is at least 2:1. The fluidic system may further comprise a sample inlet port in fluid communication with the incubation channel; an outlet port in fluid communication with the detection channel; and a sample collector adapted and arranged to be connected to the sample inlet port of the article.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 7A-7D show schematic diagrams of an assay comprising an incubation step in a fluidic device comprising an incubation channel according to one set of embodiments;

FIGS. 8A-8D show schematic diagrams of an assay comprising an incubation step in a fluidic device lacking an incubation channel according to one set of embodiments;

DETAILED DESCRIPTION

Figure 1A:
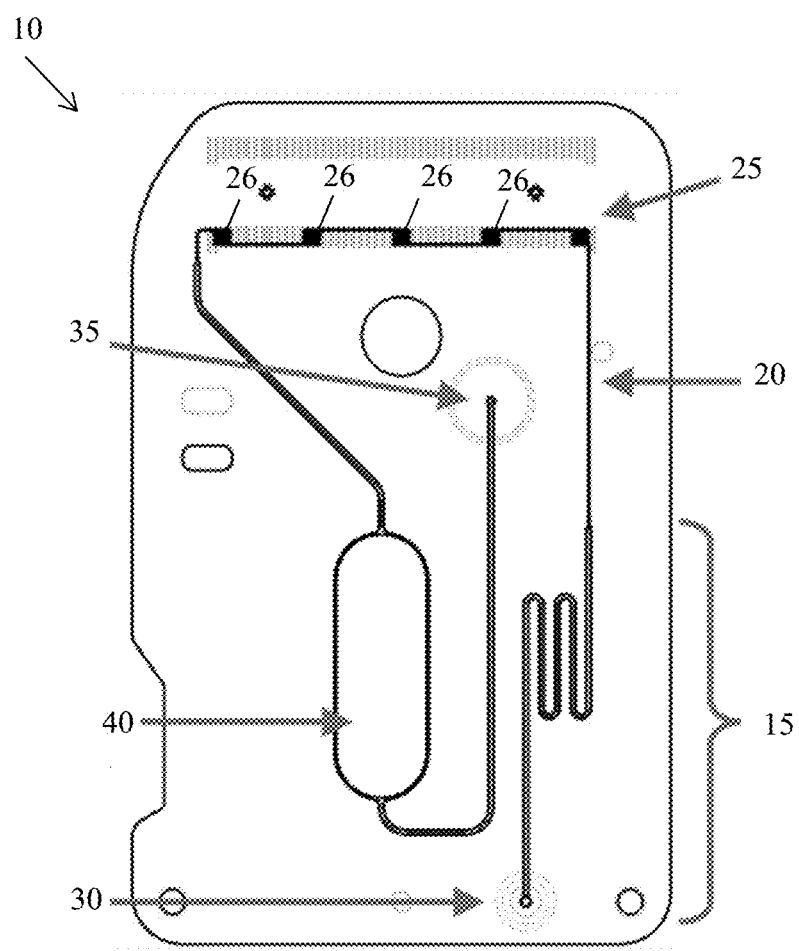
FIGS. 1A-1B show exemplary fluidic devices according to one set of embodiments.

Fluidic devices and methods involving incubation and/or mixing of assay components are provided. In some embodiments, a biological and/or chemical assay may be performed in a fluidic device. The fluidic device may be designed to allow for controlled incubation and/or mixing of two or more assay components (e.g., sample and reagent). In some such embodiments, the fluidic device may comprise an incubation channel having a relatively large cross-sectional dimension in fluid communication with a detection channel. The incubation channel may allow for adequate mixing and/or incubation of two or more assay components prior to analysis of the assay. In some embodiments, fluidic devices for performing a vitamin D assay are provided.

In certain embodiments, the detection channel may be used to provide feedback, e.g., on the presence of a sample component in the incubation channel and/or the extent of incubation and/or mixing. Based on the feedback, one or more component of the fluidic system, such as fluid flow source, may be regulated to allow the requisite degree of mixing and/or incubation to be achieved. In some embodiments, the controlled incubation and/or mixing of assay components in an incubation channel, as described herein, may allow for improved assay performance (e.g., sensitivity, specificity, and/or reproducibility) and simplification in the design and operations of fluidic devices for assays that rely on incubation and/or mixing of assay components.

Though fluidic devices exist for performing biological and/or chemical assays, certain assays cannot be readily and/or accurately performed in conventional fluidic devices due to inadequate mixing and/or incubation of assay components. For example, sufficient incubation is an important part of assays that require the target analyte to be released from a natural binding partner in the sample in order for target analyte to be detected. In some such embodiments, the amount of target analyte released, and accordingly detected, is dependent on the incubation time and insufficient control over incubation results in inaccurate results and/or irreproducibility of the assay. In certain embodiments, assay sensitivity may depend on the length of and/or temperature of incubation. For example, the amount of analyte bound to a detector binding partner (e.g., antibody) may be increased by prolonged contact and/or incubation at elevated temperatures. Conventional fluidic devices have tried to address this problem by altering the design of the fluidic device and fluid handling in the fluidic device. However, many of these conventional devices suffer from problems such as clogging, rely on complex device constructions that may be difficult to fabricate, and/or rely on complex assay methods that may be difficult to implement, e.g., at a point of care setting. The fluidic devices, described herein, may allow for sufficient mixing and/or incubation without the shortcomings of many conventional fluidic devices and can be used to perform assays not readily and/or accurately implemented in conventional fluidic devices.

In some embodiments, a biological and/or chemical assay comprising an incubation step and/or mixing step may be performed in a fluidic device. As described herein, the fluidic device may be designed to allow for controlled incubation and/or mixing of two or more assay components (e.g., sample component and a reagent; reagent and a diluent; reagent and a buffer). In one exemplary embodiment, a fluidic device 10 comprises an incubation channel 15 as shown illustratively in FIG. 1A. The incubation channel may be in fluid communication with a detection channel 20. As shown in illustratively in FIG. 1A, the detection channel is positioned between the incubation channel and a detection zone 25. The detection zone may include several analysis regions 26. However, in other embodiments, the detection channel may be a part of the detection zone (e.g., the detection channel may be a channel of the detection zone, associated with one or more detectors).

In other embodiments, a portion of the incubation channel may be a part of the detection zone (e.g., an area associated with one or more detectors). Such a configuration may allow detection of the sample while in the incubation channel, e.g., to ensure that the leading edge of the sample (e.g., the sample/air interface) is positioned in the incubation channel during an incubation step. For example, as shown illustratively in FIG. 1B, a portion of the incubation channel 15 comprises a detection zone 27, while portions of detection channel 20 comprise other detection zones 26. Upon detection of the sample at detection zone 27, the sample may be stopped or the flow rate reduced to incubate all or a portion of the sample in the incubation channel. In some embodiments, substantially no binding of the sample takes place in the incubation channel at detection zone 27.

In certain embodiments, the sample that resides in the incubation channel during incubation is in the form of a fluid plug. For example, a fluid sample may be flanked on both ends by air plugs so that a first air plug, a fluid sample, and a second air plug are positioned in the incubation channel during incubation.

In some embodiments, the dimensions (and/or cross-sectional area) of the channel at detection zone 27 are the same, or are similar to, dimensions (and/or cross-sectional area) of the incubation channel upstream of detection zone 27, e.g., as described herein. Accordingly, the dimensions (and/or cross-sectional area) of the incubation channel at the detection zone may be larger than the dimensions (and/or cross-sectional area) of the channels at the detection zone 25 where binding of a sample component may take place.

One or more of the incubation channel, detection channel, and/or detection zone may be connected to a feedback system, which may be used to control one or more aspects of incubation step and/or mixing. For instance, in some embodiments, a detection zone may be used to detect a sample component prior to the arrival of at least a portion of the sample (e.g., at least about 80% of the sample) at a downstream reaction area. One or more signals or data may be generated corresponding to the sample component. Using this data, a control system may modulate subsequent fluid flow in the fluidic device. For instance, based on the data, the control system may reduce the flow rate of the sample to a flow rate less than the initial flow rate and/or to zero to allow for additional incubation or mixing. In some embodiments, a method of modulating fluid flow to control incubation and/or mixing in the fluidic device illustrated in FIG. 1A may comprise introducing a sample into a sample collector (e.g., a blood collector). Suitable sample collectors are described below and in U.S. Pat. No. 8,202,492, issued Jun. 19, 2012 (filed May 1, 2008) and entitled "Fluidic Connectors and Microfluidic Systems" [C1256.70000US01], which is incorporated by reference in its entirety. The sample collector (e.g., blood collector) may comprise one or more channels. In some embodiments, the sample collector may comprise one or more reagents, e.g., deposited inside and/or on at least a portion of at least one channel surface of the sample collector. In some such cases, the sample may remove at least a portion of the reagent(s) and dissolve or suspend the reagent(s). In other embodiments, however, the sample collector does not contain a reagent.

Figure 1B:
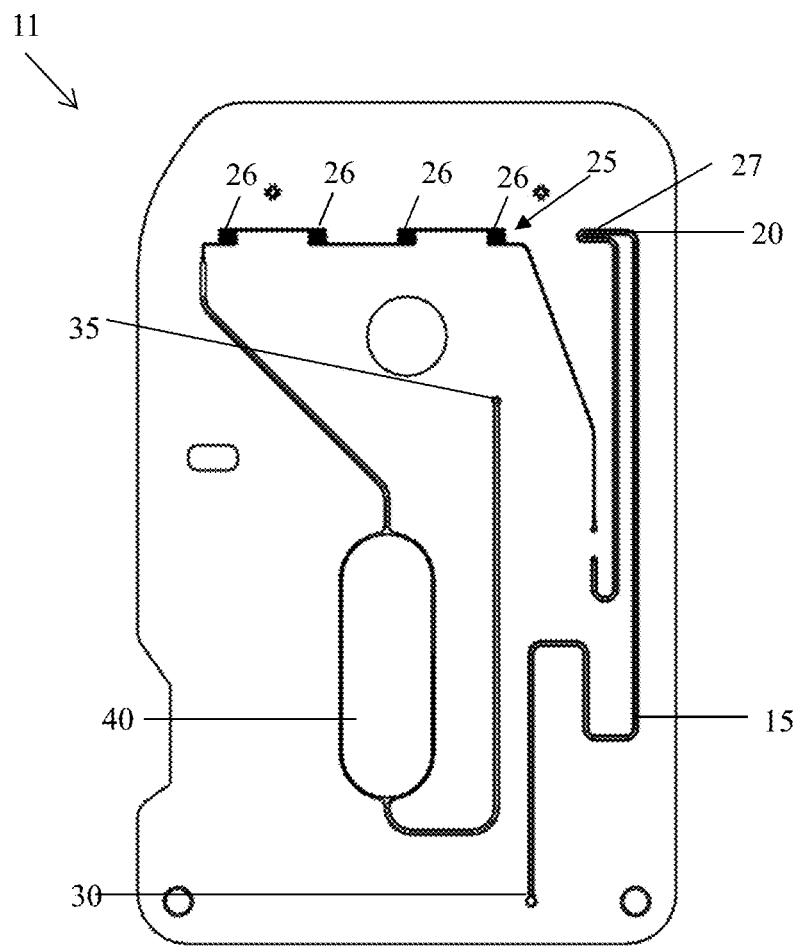

Referring to FIGS. 1A and 1B, the sample collector containing the sample may then be connected to a sample inlet port 30 of the fluidic device. The sample collector may be a fluidic connector in certain embodiments. In some embodiments, the sample collector may provide fluid communication between two channels on the fluidic device that prior to connection of the sample collector were not in fluid communication with each other. For instance, in some embodiments, a sample collector comprising a channel is used to connect two independent channels in a fluidic device so as to allow fluid communication between the two independent channels. One or both of the independent channels may optionally be pre-filled with reagents (e.g., antibody solutions, washing buffers and amplification reagents), which can be used to perform the analysis. These reagents may be stored (e.g., sealed) in the channels of the substrate for long periods of time (e.g., 1 year) prior to use. Prior to connection of the sample collector and the fluidic device, the channel of the sample collector may be filled with a sample (e.g., blood). The sample may be obtained, for example, by pricking a finger of a user until blood is drawn from the finger into the channel (e.g., by capillary forces). Upon connection of the sample collector and the channels of the fluidic device, the sample can pass through a detection zone and/or analysis regions within the fluidic device.

In embodiments in which the sample collector is connected to the fluidic device, a volume or pressure source may be connected to a fluid flow source port 35 (e.g., an outlet) and an applied force (e.g., a vacuum or reduce pressure) may cause the sample to flow into the fluidic device. In some embodiments, the sample may flow directly into the incubation channel after entering the sample inlet port. In other embodiments, the sample may enter another structure (e.g., a channel) prior to entering the incubation channel. In some instances, the incubation channel may have one or more dimensions (e.g., length, width, height) and/or volume that allows the incubation channel to contain substantially all of the sample (e.g., at least about 80% of the volume of the sample; at least about 95% of the volume of the sample, the entire sample). For example, the incubation chamber may be configured to contain samples having a volume of at least about 0.0005 mL, at least about 0.001 mL, 0.005 mL, at least about 0.01 mL, at least about 0.02 mL, at least about 0.03 mL, at least about 0.05 mL, at least about 0.08 mL, or at least about 0.01 mL and less than or equal to about 1 mL, less than or equal to about 0.75 mL, less than or equal to about 0.5 mL, less than or equal to about 0.25 mL, or less than or equal to about 0.1 mL. All combinations of the above-referenced ranges are possible. In some instances, the volume of the incubation channel may be similar to the volume of the sample. For instance, in some embodiments, the ratio of the volume of the incubation channel to the volume of the sample may be less than or equal to about 3:1, less than or equal to about 2.5:1, less than or equal to about 2:1, less than or equal to about 1.5:1, or less than or equal to about 1:1 and at least about 0.6:1, at least about 0.7:1, at least about 0.8:1, or at least about 0.9:1. All combinations of the above-referenced ranges are possible. In some embodiments, the incubation channel may have a larger cross-section area than another channel (e.g., detection channel) in the fluidic device. In other embodiments, the incubation channel is designed to be smaller in volume than the volume of the sample, e.g., such that it cannot contain a relatively large percentage of the sample.

In some embodiments, at least a portion of the sample is incubated in the incubation channel for a period of time. As described herein, the flow of the sample may be stopped, or the flow rate reduced, during the incubation step.

In some embodiments, the volume or pressure source may be modulated to a predetermined setting for a predetermined length of time so that at least a portion of the sample flows into the incubation channel. In some such embodiments, a detector, e.g., for determining whether or not the incubation channel has been filled with the sample, is not needed or present at the incubation channel. Instead, the filling of the incubation channel, including the predetermined volume or pressure source settings and time (e.g., vacuum level and time of application of the vacuum) may be determined and adjusted based on the type of sample and its flow properties (e.g., whole blood capillary whole blood drawn from a finger stick, venous whole blood, plasma, serum, urine, saliva, etc., including its viscosity). as well as the channel dimensions leading up to and including the incubation channel (e.g., width, height, length, and thereby volume). The pressure source level and timing of application of the pressure source may be tailored for the particular application.

In certain embodiments, at least a portion, but not all, of the sample enters into the incubation channel upon the incubation step. In some cases, the sample enters into the incubation channel, but does not enter into any downstream channels such as the detection channel, detection zone, waste zone, or outlet of the device. In other embodiments, at least a portion of the sample enters into the incubation channel, but the leading edge of the sample (e.g., an air/sample interface) does not enter into, or stop at, a channel downstream of the incubation channel within a range of cross-sectional areas.

For instance, the sample may be stopped, or the flow rate reduced for incubation, when the leading edge of the sample reaches a channel having a relatively large cross-sectional area so that the sample does not clog the channel during and/or after incubation. In general, there is an increased tendency for certain samples (especially at a sample/air interface) to clog in channels having a relatively small cross-sectional area due to drying, clotting, and/or coagulation of the sample, which can increase resistance to fluid flow when sample flow is resumed.

In some embodiments, this tendency to clog may be addressed by having the sample (including the leading edge of the sample such as the sample/air interface) stop, or flow rate reduced when the sample reaches, a channel having a certain cross-sectional area. The cross-sectional area of the channel may be, for example, at least 0.008 $mm^2$, at least 0.01 $mm^2$, at least 0.02 $mm^2$, at least 0.03 $mm^2$, at least 0.04 $mm^2$, at least 0.05 $mm^2$, at least 0.06 $mm^2$, at least 0.08 $mm^2$, at least 0.10 $mm^2$, at least 0.12 $mm^2$, at least 0.14 $mm^2$, at least 0.16 $mm^2$, at least 0.18 $mm^2$, at least 0.20 $mm^2$, at least 0.30 $mm^2$, at least 0.40 $mm^2$, at least 0.50 $mm^2$, at least 0.60 $mm^2$, at least 0.70 $mm^2$, at least 0.80 $mm^2$, at least 0.90 $mm^2$, or at least 1.00 $mm^2$. In some embodiments, the cross-sectional area may be less than or equal to 1.00 $mm^2$, less than or equal to 0.90 $mm^2$, less than or equal to 0.80 $mm^2$, less than or equal to 0.70 $mm^2$, less than or equal to 0.60 $mm^2$, less than or equal to 0.50 $mm^2$, less than or equal to 0.40 $mm^2$, less than or equal to 0.30 $mm^2$, less than or equal to 0.25 $mm^2$, less than or equal to 0.20 $mm^2$, less than or equal to 0.175 $mm^2$, less than or equal to 0.15 $mm^2$, less than or equal to 0.1 $mm^2$, less than or equal to 0.05 mm$^2$, less than or equal to 0.04 mm$^2$, less than or equal to 0.02 mm$^2$, less than or equal to 0.015 mm$^2$, or less than or equal to 0.010 mm$^2$. Combinations of the above-referenced ranges are also possible. Other ranges are also possible. In some embodiments, the incubation channel has a cross-sectional area in one or more of the above-referenced ranges.

In some embodiments, a detection channel of a detection zone (e.g., where binding of a sample component takes place) has a cross-sectional area that is smaller than a cross-sectional area of the incubation channel. The detection channel of a detection zone may have, for example, a cross-sectional area of at least 0.001 mm$^2$, at least 0.002 mm$^2$, 0.004 mm$^2$, 0.005 mm$^2$, 0.006 mm$^2$, 0.008 mm$^2$, at least 0.01 mm$^2$, at least 0.02 mm$^2$, at least 0.03 mm$^2$, at least 0.04 mm$^2$, at least 0.05 mm$^2$, at least 0.06 mm$^2$, at least 0.08 mm$^2$, or at least 0.10 mm$^2$. In some embodiments, the cross-sectional area may be less than or equal to 0.016 mm$^2$, less than or equal to 0.014 mm$^2$, less than or equal to 0.012 mm$^2$, less than or equal to 0.010 mm$^2$, less than or equal to 0.008 mm$^2$, less than or equal to 0.006 mm$^2$, less than or equal to 0.005 mm$^2$, or less than or equal to 0.004 mm$^2$, less than or equal to 0.003 mm$^2$, or less than or equal to 0.002 mm$^2$. Combinations of the above-referenced ranges are also possible. Other ranges are also possible.

In some embodiments, the sample may flow through the incubation channel and a portion of the sample may reach the detection channel. As described herein, in some embodiments, the detection channel may have a significantly smaller cross-sectional area than the incubation channel. Accordingly, the flow rate inside the detection channel and/or the volume of the detection channel may be significantly less than the flow rate and/or volume of the incubation channel. In some embodiments, at least a portion of the sample may enter into a detection region (e.g., detection channel and/or detection zone) whereby the presence or absence of the sample or sample component and/or one or more characteristic of the sample or sample component are detected. In some such embodiments, the portion of the sample may flow into part, but not all, of the detection region (e.g., detection channel, detection zone). In certain embodiments, a small percentage of the sample (e.g., less than or equal to about 10%, less than or equal to about 5%) may flow into the detection region to initiate such analysis. One or more signals generated from such detection may be sent to a control system. For instance, detection may involve detecting the presence of a sample via a light absorbance or a transmission measurement.

In some cases, the feedback from the detection may be used to alter one or more component of the fluidic system to modulate fluid flow. For example, detection of the sample passing across the detection zone may trigger control of whether or not a particular valve is actuated to modulate fluid flow in the incubation channel. In some such embodiments, the one or more signals generated from the detection of the sample may be compared to one or more pre-set values, and based (at least in part) on this feedback and comparison, a control system may modulate (e.g., cease or reduce) fluid flow in the incubation channel and/or other portion of the fluidic device (e.g., entire fluidic device) if the measured signals falls out of range with the pre-set values. In some instances, fluid flow of one portion of the device may be regulated separately from another portion of the device using, e.g., a valve such as a vent valve. Vent valves for the regulation of fluid flow are described in U.S. Patent Publication No. 2011/0120562, filed Nov. 24, 2010, entitled "Fluid Mixing and Delivery in Microfluidic Systems," [C1256.70005US01], which is incorporated by reference in its entirety.

In some embodiments, based on the information from the signal, the volume or pressure source may be modulated to increase or decrease the flow rate, or in other cases, the flow rate may be maintained. In one example, the sample may have a first flow rate before detection (e.g., at a detection region such as the detection zone) and the sample may have a second flow rate after detection. The second flow rate may be significantly less than the first flow rate. For instance, the second flow rate may be less than or equal to about 50% (e.g., less than or equal to about 40%, less than or equal to about 30%, less than or equal to about 20%, less than or equal to about 10%, less than or equal to about 5%, less than or equal to about 1%) of the first flow rate. In some instances, the second flow rate may be zero. The reduction in flow rate may allow sufficient incubation and/or mixing to occur before the remaining portion of the sample leaves the incubation channel and/or arrives at a certain downstream location, such as a reaction area/analysis region. In other embodiments, the second flow rate may be greater than or equal to the first flow rate.

In some embodiments, the first flow rate, the second flow rate, or the third flow rate as described herein may each independently be at least $\frac{1}{100}$ mm/s, at least $\frac{1}{50}$ mm/s, at least $\frac{1}{20}$ mm/s, at least $\frac{1}{10}$ mm/s, at least $\frac{1}{5}$ mm/s, at least 1 mm/s, at least 2 mm/s, at least 4 mm/s, at least 6 mm/s, at least 8 mm/s, at least 10 mm/s, at least 12 mm/s, at least 14 mm/s, at least 16 mm/s, at least 18 mm/s, at least 20 mm/s, at least 25 mm/s, at least 30 mm/s, at least 40 mm/s, at least 50 mm/s, at least 60 mm/s, at least 70 mm/s, at least 80 mm/s, at least 90 mm/s, at least 100 mm/s, at least 120 mm/s, at least 150 mm/s, at least 200 mm/s, at least 500 mm/s, at least 700 mm/s, or at least 1000 mm/s. In some embodiments, the first flow rate, the second flow rate, or the third flow rate as described herein may each independently be less than or equal to 2000 mm/s, less than or equal to 1000 mm/s, less than or equal to 700 mm/s, less than or equal to 500 mm/s, less than or equal to 200 mm/s, less than or equal to 100 mm/s, less than or equal to 80 mm/s, less than or equal to 60 mm/s, less than or equal to 40 mm/s, less than or equal to 20 mm/s, less than or equal to 10 mm/s, less than or equal to 1 mm/s, or less than or equal to $\frac{1}{10}$ mm/s. Combinations of the above referenced ranges for each of the first flow rate, the second flow rate, or the third flow rate as described herein are also possible. Other ranges are also possible.

In some embodiments, one or more of the flow rates descibed above may be used to implement flow conditions such that the blood cells in a sample move away from the surface of the channel (e.g., microchannel), leaving only the plasma component of the sample to interact with the surface (where the immunoreaction takes place).

Figure 2:
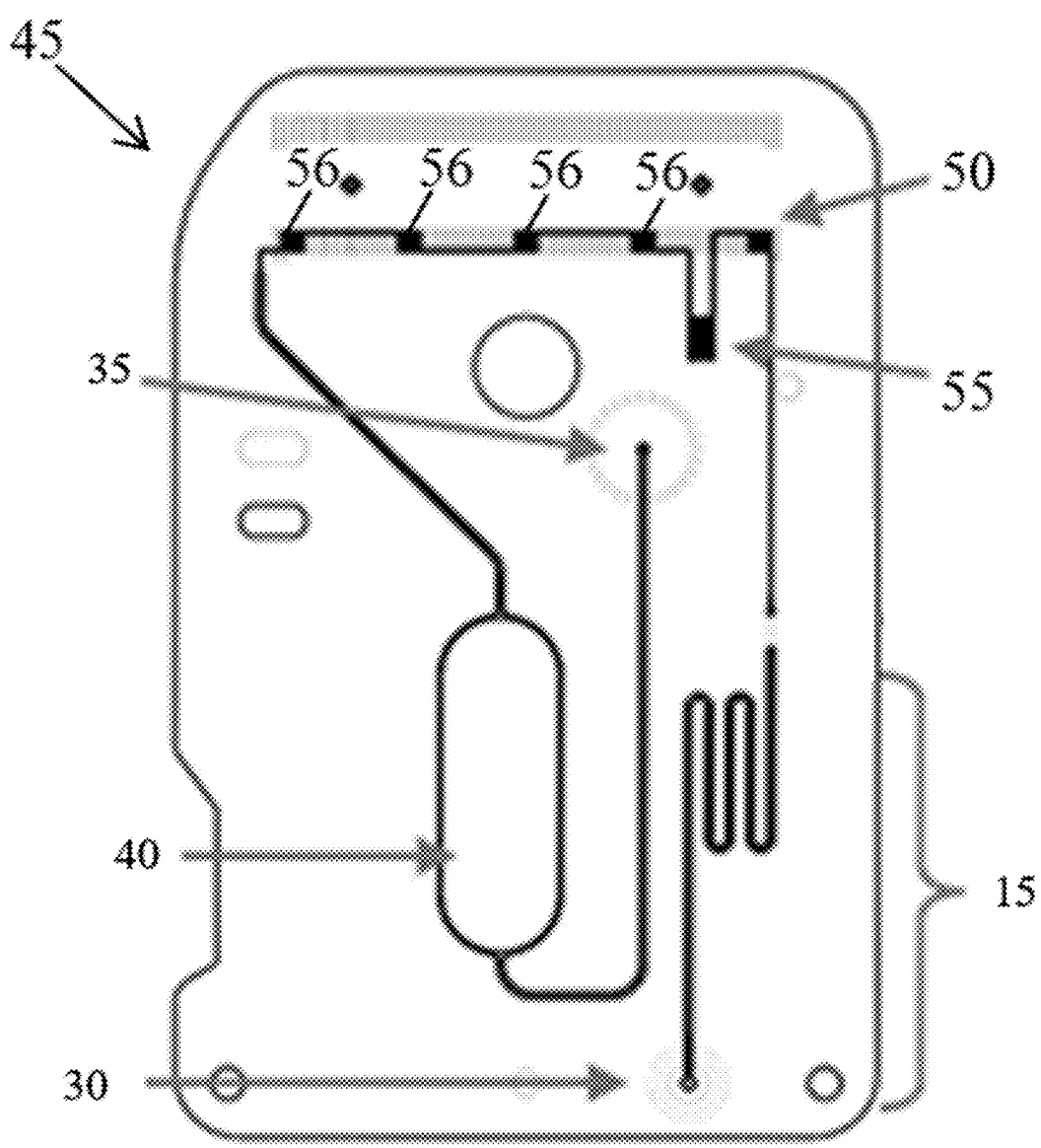
FIG. 2 shows a fluidic device according to one set of embodiments.

In some embodiments, to prevent the portion of the sample at the detection zone from reaching an analysis region and/or another downstream detection zone, the fluidic device may comprise an additional channel 55 between a detection zone 50 and a downstream feature of the fluidic device (e.g. additional analysis regions 56) as shown illustratively in FIG. 2. As a result of detecting a component of a sample at analysis region 56, fluid flow may cease or be reduced so that the sample is further incubated or mixed in the mixing channel. After sufficient incubation or mixing, the sample may then continue towards the remaining analysis regions of the detection zone where a component of the sample can be detected and/or analyzed.

In some embodiments in which the flow rate is adjusted after detection of the sample or sample component in a detection region, after a certain period of time, which may be preset based on the assay or determined by subsequent detection of the sample or sample component, the flow rate may be modulated to a third flow rate which is greater than or less than the second flow rate. For instance, after a preset incubation time the flow rate may increase to a third flow rate that is greater than the second flow rate. The third flow rate may be greater than, less than, or equal to the first flow rate. In some embodiments, the fluidic device may be configured to allow for fluid flow to be slowed significantly or stopped without negatively influencing subsequent operations (e.g., fluid flow) in the fluidic device. For instance, fluid flow may be stopped and restarted in the fluidic device without clogging occurring.

In some embodiments, a method may further involve reducing the temperature of the sample, a reagent, and/or channels (e.g., incubation channel, or channels at a detection zone) to a temperature less than a temperature used during an incubation step after the incubation step occurs. For example, the temperature may be reduced during a detection step. Such a temperature reduction may, in some embodiments, improve and/or increase the flow rate of the sample through the detection zone. For example, the temperature may be reduced to less than or equal to 60° C., less than or equal to 55° C., less than or equal to 50° C., less than or equal to 45° C., less than or equal to 40° C., less than or equal to 37° C., less than or equal to 35° C., less than or equal to 30° C., or less than or equal to 25° C. In some embodiments, the temperature may be at least 15° C., at a temperature of at least 20° C., at a temperature of at least 25° C., at least 30° C., at least 35° C., at least 40° C., at least 45° C., at least 50° C., or at least 55° C. Combinations of the above-referenced ranges are also possible (e.g., at least 20° C. and less than or equal to 55° C.). First or third temperatures described herein may each independently have a value in one or more of the above-referenced ranges.

Accordingly, in some embodiments, a method may involve a sample or reagent (or a channel, such as an incubation channel) having a first temperature (e.g., a temperature in one or more ranges described herein, including the temperatures noted above for the reduced temperatures). The sample or reagent may then be incubated at (or a channel may be exposed to) a second temperature, wherein the second temperature is greater than the first temperature. The second temperature may have a value as described herein for an incubation temperature. The sample or reagent (or a channel) may then have or be exposed to a third temperature, wherein the third temperature is less than the second temperature. The third temperature may be a temperature in one or more ranges described herein, including the temperatures noted above for the reduced temperatures. In some cases, the third temperature is the same as the first temperature, although different first and third temperatures are also possible. In some cases, for example, the third temperature is greater than the first temperature, but is less than the second temperature.

As noted above, after the controlled incubation and/or mixing period the remaining portion of the sample may be flowed through the detection channel, which may be separate from or part of a detection zone as described herein. In some instances, the detection channel may comprise a reagent deposited on at least a portion of at least one surface of the detection channel. The reagent may interact (e.g., bind, react) with another reagent or sample component in the sample. From the detection channel, the sample may pass through other downstream components of the fluidic device including one or more analysis regions/reaction areas. Excess sample and/or other assay components (e.g., reagents) may be collected in waste chamber 40 of the fluidic device as illustrated in FIG. 1A.

Figure 3:
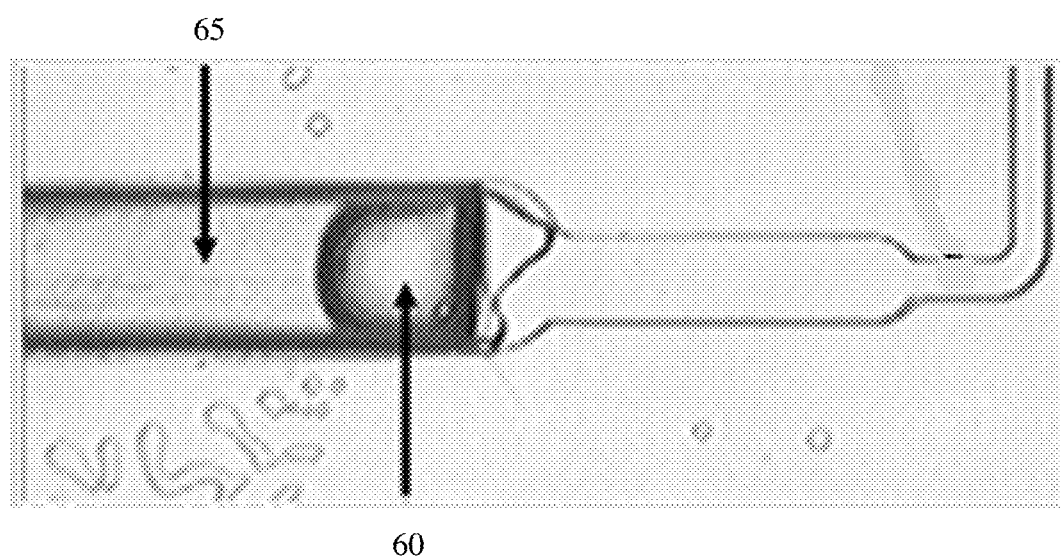
FIG. 3 is an image of a junction in a conventional fluidic device according to one set of embodiments.
Figure 4A:
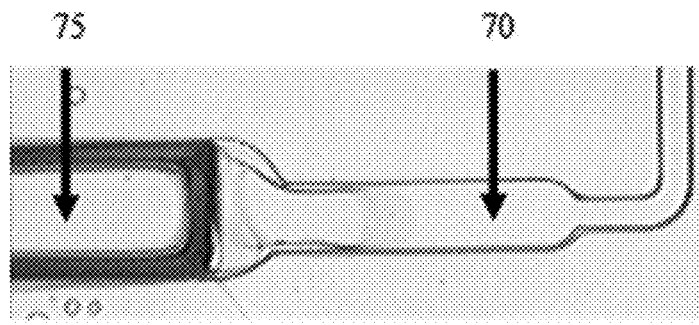
FIGS. 4A-D are images of fluid flow in a junction of a conventional fluidic device according to one set of embodiments.
Figure 4B:
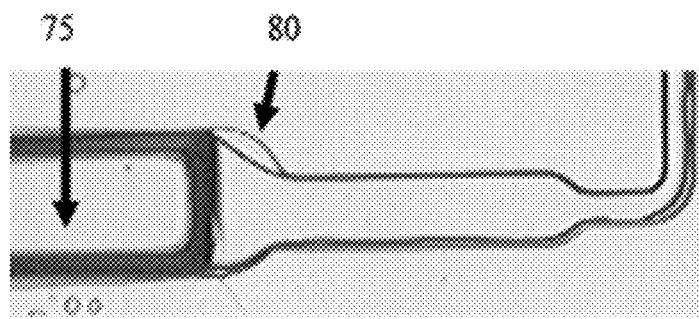
Figure 4C:
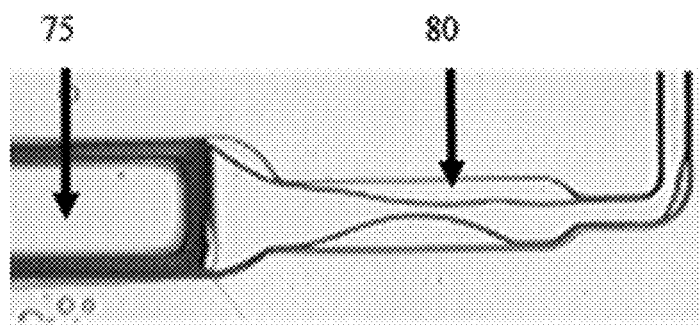
Figure 4D:
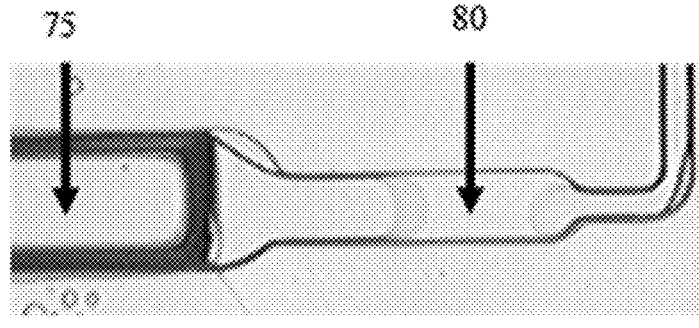

As described herein, the fluidic device may be configured to allow for controlled fluid handling without negatively affecting the operation of the fluidic device. For instance, fluid flow in the incubation channel may be ceased and restarted without clogging the channels in the fluidic device. In many conventional fluidic devices, transitions in channel geometry from large to small cross-sectional area, like the transition from the incubation channel to the detection channel in some embodiments described herein, may negatively affect operation of the fluidic device. For instance, in some embodiments in which the fluidic device is used for multi-phase fluid flow (e.g., gaseous plugs adjacent to liquid plugs) and includes a transition in the cross-sectional area of the channel, undesirable processes such as clogging, droplet formation, and/or trapping of fluid may occur. An example of clogging of a fluid at a geometrical transition is shown in FIG. 3. FIG. 3 shows an image of the junction of a channel having a large cross-sectional area adjacent to a channel having a small cross-sectional area. An air bubble 60 is trapped at the junction and acts as a clog preventing flow of a liquid 65. Air bubble 60 trapped at geometrical constriction can shed multiple air small bubbles (with a volume equal to a fraction of the trapped air bubble 60), resulting in a series of bubbles being present downstream of the constriction. Each air bubble present in the downstream channel will increase resistance to flow, and the presence of multiple air bubbles can, in some cases, reduce the flow rate to nearly no flow (e.g., they may cause the channel to clog). The change in geometry between the channel having a relatively large cross-sectional area and the channel having a relatively small cross-sectional area can be designed so that no air bubble would be trapped at the change in geometry.

FIG. 4 shows a sequence of images that illustrate droplet formation at a geometrical transition. FIG. 4A shows a liquid plug 70 downstream of a gas fluid plug 75. The liquid plug has entered the channel with the smaller cross-sectional area and the gas plug is beginning to enter the channel having the smaller cross-sectional area. As the liquid plug flow through this junction followed by the air plug 75, a small volume of liquid 80 is captured in the junction as shown in FIGS. 4B and 4C. As shown in FIG. 4D, this volume of liquid may serve as a source of droplets which form in the air flow, potentially causing analytical problems downstream. Moreover, trapped volume from multiple fluids can mix at this junction, and combine to form droplets which might impact reactions downstream.

A fluidic device, as described herein, may be designed to avoid clogging, trapping one or more fluids, formation of air bubbles, and/or releasing a trapped fluid at inappropriate times. In some embodiments, a junction between an incubation channel and a detection channel may be configured to prevent these problems. For instance, in some embodiments, a fluidic device may include channels positioned on two sides of an article. The channels may be connected by an intervening channel, e.g., that passes through the thickness of the article used to form the channels of the fluidic device. An intervening channel refers to a channel that connects two channels lying on two different planes. The specific geometry of the channels and the positions of the channels within the fluidic devices described herein may allow clogging and/or trapping of one or more fluids to be avoided. For example, the presence of an intervening channel (e.g., that passes through the thickness of the article) may allow an incubation channel having a relatively large cross-sectional dimension to be fluidically connected to a detection channel having a relatively small cross-sectional dimension, without an abrupt change in cross-sectional dimensions of the channels that contributes to the clogging and/or trapping of fluids as shown in FIG. 3.

In some embodiments, channels (e.g., incubation channel, detection channel) having non-circular cross-sections are fabricated on the first and/or the second side of an article. The channels on the first side of the article are connected with channels on the second side of the article via intervening channels, which, in some embodiments, may have circular cross sections and can pass through the thickness of the article from the first side to the second side. In this way, each of the channels on the first side can be connected fluidically to the channels on the second side to form a single continuous channel. An advantage of such a configuration is that from a fabrication perspective, channels having non-circular cross sections can be easily fabricated on planar surfaces, and channels having circular cross sections can be easily fabricated in the form of through-holes between the two surfaces of an article.

Figure 5A:
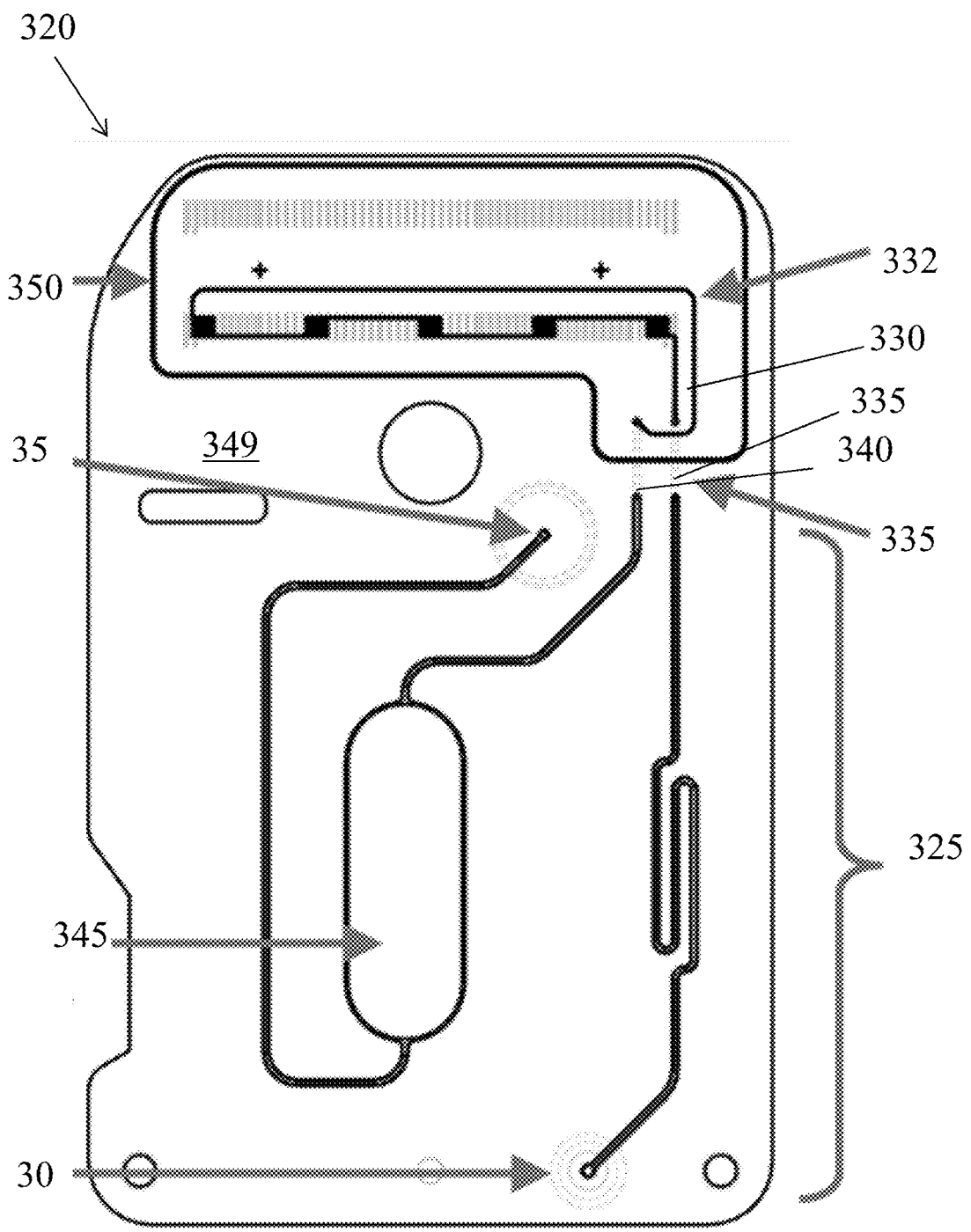
FIGS. 5A-5C show (A) a fluidic device, (B) pieces used to form certain fluidic devices, and (C) a fluidic device according to certain embodiments.

Moreover, in some embodiments, the use of intervening channels may also simplify the fabrication of the fluidic device by, e.g., expanding the fabrications methods that can be utilized. For example, in embodiments in which the fluidic device is formed at least in part by injection molding, channels in a molded part are defined by a tool insert which contains the inverse features on its surface. For a given channel on a single surface of an article, it is often preferred that the features which define the channel are on a single monolithic piece (e.g., a single component or substrate). Crossing a channel across two pieces may be problematic. For instance, it may be difficult to line up features perfectly, resulting in channels which are imperfect. The interface between the two pieces may result in flash, where the molten material (e.g., plastic) used to form the article flows into any tiny gap between the pieces. Such flash may result in leaks in a finished article or otherwise impede the function of the article. An intervening channel can serve as a method to join two or more channels, each fabricated on different pieces, while avoiding problems with the interface of the pieces. FIG. 5A shows a fluidic device 320 where the relatively large channels (e.g., incubation channel 325 of the fluidic device are molded against one piece, e.g., piece 355 in FIG. 5B), yet the relatively small channels (e.g., detection channel 330 in detection zone 332), on the same surface, are molded against a separate piece (e.g., mounted within piece 350 in FIG. 5B). Thus, the device or substrate may include a first piece 349 and a second piece 350 that are formed from two different molds and attached to one another to form the channel system.

Figure 5B:
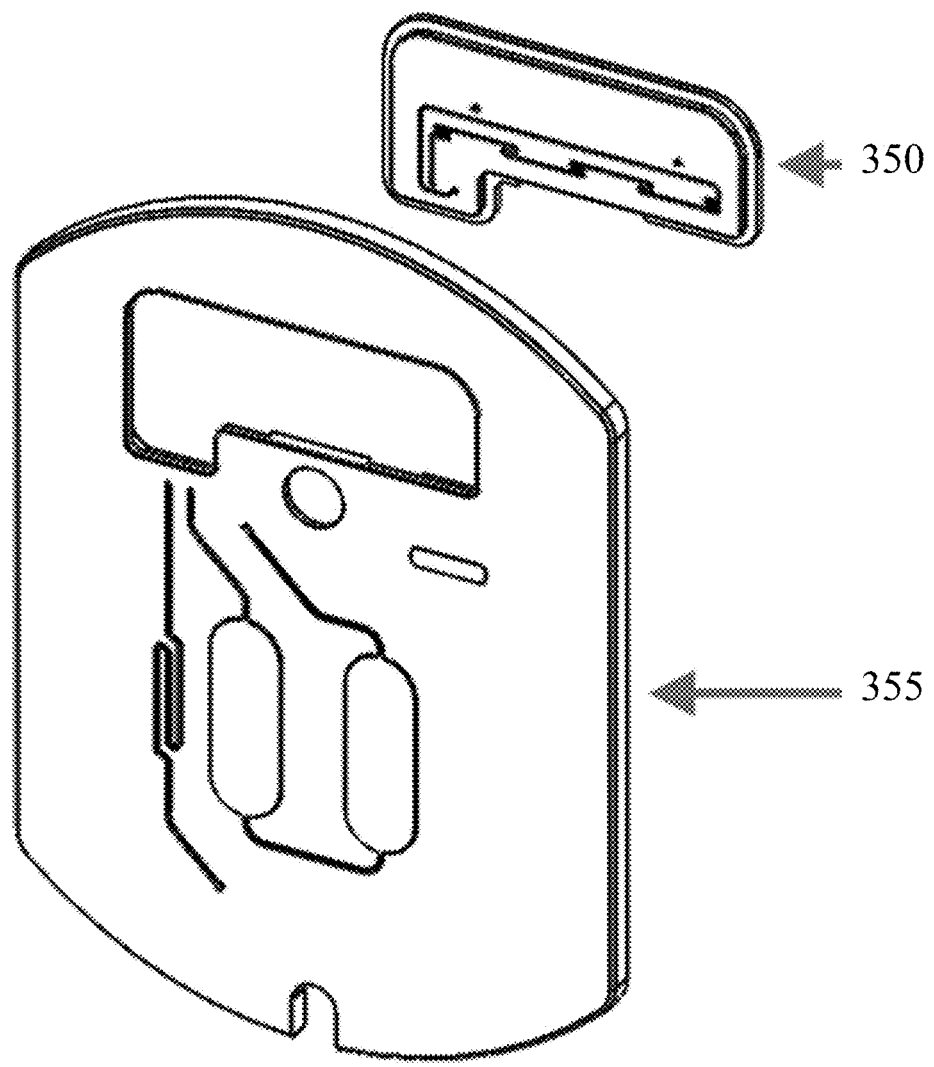

As shown illustratively in FIG. 5A, an intervening channel 335 connects the incubation channel with the detection channel. Another intervening channel 340 downstream of the analysis regions connects the small channels to the large outlet channel which leads to a waste zone 345. An advantage of this design is that different fabrication techniques can be used to make the two pieces. For example, certain fabrication techniques, such as lithography and etching, may be suitable for small features, but impractical for larger features or for features of multiple heights. Conversely, techniques such as mechanical milling may be well suited for larger features, but incapable of producing smaller features. FIG. 5B shows such two-part mold pieces that were used to produce the fluidic device shown in FIG. 5A.

In some embodiments, the incubation and detection channel are not on the same side of an article of the fluidic device. In some such embodiments, an intervening channel may form a bridge between an incubation channel (e.g., formed in a first surface of the article) and a detection channel (e.g., formed in a second surface of the article).

Figure 5C:
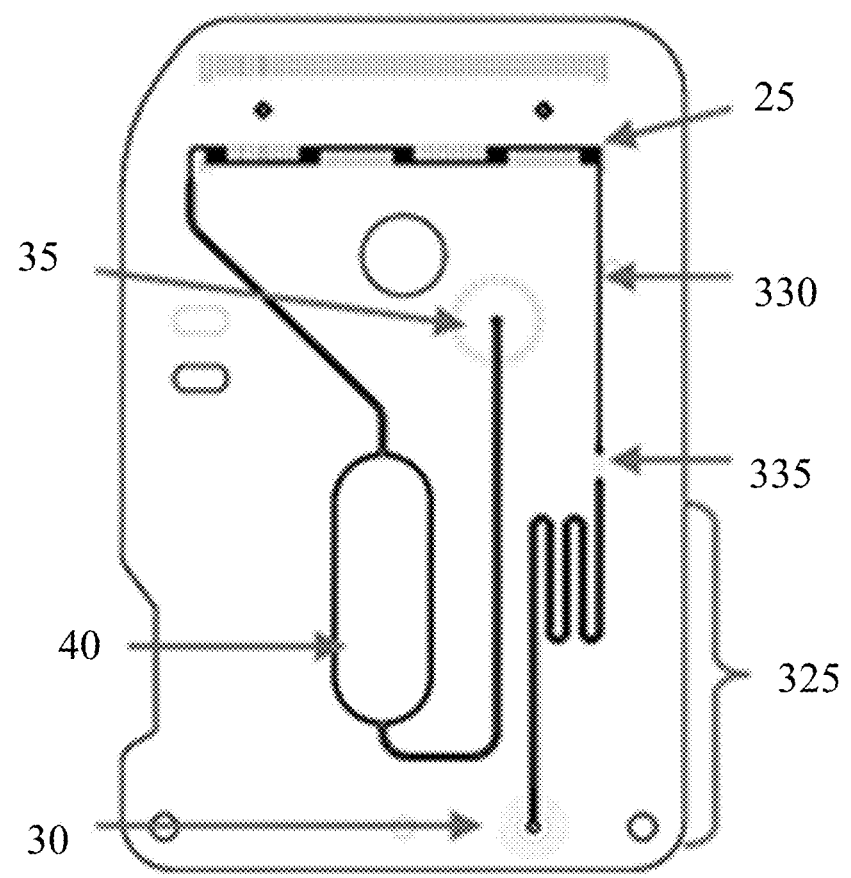

In another embodiment, both the incubation channel and the detection channel are formed on the same side of an article as shown in FIG. 5C (e.g., in a first surface of the article), and the channels are connected by an intervening channel 335 and a channel formed on the second surface of the article. The intervening channel and channel formed on the second surface of the article may act as bridging channels, e.g., channels that bridge the incubation channel and detection channel.

Figure 6:
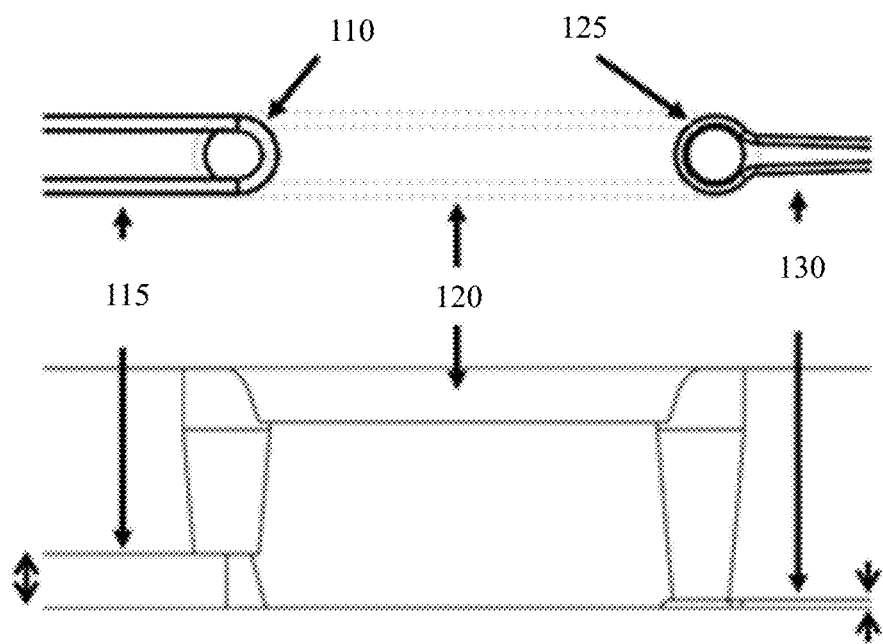
FIG. 6 shows a cross-section of a fluidic device comprising an intervening channel according to one set of embodiments.

A non-limiting example of a bridge is shown in FIG. 6. As shown in FIG. 6, the bridge may comprise a through-hole 110 (e.g., an intervening channel) that forms a non-zero angle (e.g., perpendicular to) with respect to the plane of an incubation channel 115, a bridging channel 120 on the opposite side of the article and substantially parallel to the incubation channel, and a through hole 125 (e.g., an intervening channel) from the bridging channel to the detection channel 130, which is on the same plane/side as the incubation channel. In some embodiments, one or more of the through-holes (e.g., an intervening channel) may have a substantially circular cross-section.

In some embodiments, the dimensions of the incubation channel and detection channel play a role in proper performance of the fluidic device. In some embodiments, the incubation channel may have a width of less than or equal to about 2 mm, less than or equal to about 3 mm, less than or equal to about 1 mm, less than or equal to about 750 microns, less than or equal to about 600 microns, less than or equal to about 500 microns, less than or equal to about 300 microns, or less than or equal to about 200 microns. In some instances, the incubation channel may have a width of greater than or equal to about 100 microns, greater than or equal to about 200 microns, greater than or equal to about 400 microns, greater than or equal to about 600 microns, greater than or equal to about 900 microns, greater than or equal to about 1 mm, or greater than or equal to about 1.5 mm. Combinations of the above-referenced ranges are also possible (e.g., greater than or equal to about 100 micron and less than or equal to about 2 mm).

In some embodiments, the incubation channel may have a height of less than or equal to about 2 mm, less than or equal to about 3 mm, less than or equal to about 1 mm, less than or equal to about 750 microns, less than or equal to about 600 microns, less than or equal to about 500 microns, less than or equal to about 300 microns, less than or equal to about 200 microns, or less than or equal to about 100 microns. In some instances, the incubation channel may have a height of greater than or equal to about 50 microns, greater than or equal to about 75 microns, greater than or equal to about 100 microns, greater than or equal to about 200 microns, greater than or equal to about 400 microns, greater than or equal to about 600 microns, greater than or equal to about 900 microns, greater than or equal to about 1 mm, or greater than or equal to about 1.5 mm. Combinations of the above-referenced ranges are also possible (e.g., greater than or equal to about 50 micron and less than or equal to about 2 mm).

In some embodiments, the incubation channel may have a volume of at least about 0.001 mL, at least about 0.005 mL, at least about 0.01 mL, at least about 0.02 mL, at least about 0.03 mL, at least about 0.05 mL, at least about 0.08 mL, or at least about 0.01 mL. In some instances, the incubation channel has a volume less than or equal to about 1 mL, less than or equal to about 0.75 mL, less than or equal to about 0.5 mL, less than or equal to about 0.25 mL, or less than or equal to about 0.1 mL. Combinations of the above-referenced ranges are also possible.

In some embodiments, the detection channel may have a width of less than or equal to about less than or equal to about 300 microns, less than or equal to about 250 microns, less than or equal to about 200 microns, less than or equal to about 150 microns, less than or equal to about 100 microns, or less than or equal to about 75 microns. In some instances, the detection channel may have a width of greater than or equal to about 50 microns, greater than or equal to about 75 microns, greater than or equal to about 100 microns, greater than or equal to about 150 microns, greater than or equal to about 200 microns, or greater than or equal to about 250 microns. Combinations of the above-referenced ranges are also possible (e.g., greater than or equal to about 50 microns and less than or equal to about 300 microns).

In some embodiments, the detection channel may have a height of less than or equal to about less than or equal to about 300 microns, less than or equal to about 250 microns, less than or equal to about 200 microns, less than or equal to about 150 microns, less than or equal to about 100 microns, less than or equal to about 75 microns, less than or equal to about 50 microns, or less than or equal to about 25 microns. In some instances, the detection channel may have a height of greater than or greater than or equal to about 10 microns, greater than or equal to about 15 microns, greater than or equal to about 25 microns, equal to about 50 microns, greater than or equal to about 75 microns, greater than or equal to about 100 microns, greater than or equal to about 150 microns, greater than or equal to about 200 microns, or greater than or equal to about 250 microns. Combinations of the above-referenced ranges are also possible (e.g., greater than or equal to about 10 microns and less than or equal to about 300 microns).

In some embodiments, the ratio of the height of the incubation channel to the detection channel may be at least about 1.5:1, at least about 2:1 (e.g., at least about 5:1, at least about 8:1, at least about 10:1, at least about 15:1, at least about 20:1, at least about 30:1, at least about 40:1, at least about 50:1). In some embodiments, the ratio of the height of the incubation channel to the detection channel may be less than or equal to about 1,000:1, less than or equal to about 750:1, less than or equal to about 500:1, less than or equal to about 400:1, less than or equal to about 300:1, less than or equal to about 200:1, less than or equal to about 100:1, less than or equal to about 50:1, less than or equal to about 10:1, or less than or equal to about 7:1. Combinations of the above-referenced ranges are also possible.

In some embodiments, the ratio of the width of the incubation channel to the detection channel may be at least about 1.5:1, at least about 2:1 (e.g., at least about 5:1, at least about 8:1, at least about 10:1, at least about 15:1, at least about 20:1, at least about 30:1, at least about 40:1, at least about 50:1). In some embodiments, the ratio of the width of the incubation channel to the detection channel may be less than or equal to about 1,000:1, less than or equal to about 750:1, less than or equal to about 500:1, less than or equal to about 400:1, less than or equal to about 300:1, less than or equal to about 200:1, less than or equal to about 100:1, less than or equal to about 50:1, less than or equal to about 10:1, or less than or equal to about 7:1. Combinations of the above-referenced ranges are also possible.

In certain embodiments, including an incubation channel having a height that is greater than the height of a detection channel can allow the volume of the incubation channel to be increased in a manner that would facilitate incubation and/or mixing within the incubation channel, compared to such a process in an incubation channel having the same or smaller height than that of the detection channel. It is often challenging to fabricate channels having different heights within the same substrate, especially using fabrication methods such as injection molding (e.g., using the same injection molding tool). One option for addressing this challenge is by separating the incubation channel from the detection channel using one or more intervening channels as described herein.

In some embodiments, the ratio of volume of the incubation channel to the detection channel is at least about 2:1 (e.g., at least about 5:1, at least about 8:1, at least about 10:1, at least about 15:1, at least about 20:1, at least about 30:1, at least about 40:1, at least about 50:1, at least about 100:1, or at least about 200:1). In some embodiments, the ratio of volume of the incubation channel to the detection channel is less than or equal to about 1,000:1, less than or equal to about 750:1, less than or equal to about 500:1, less than or equal to about 400:1, less than or equal to about 300:1, or less than or equal to about 200:1. Combinations of the above-referenced ranges are also possible.

As described herein, a biological and/or chemical assay may be performed in a fluidic device. In some embodiments, the assay may comprise an incubation step and/or mixing step. For instance, the assay may require the incubation and/or mixing of two or more assay components (e.g., sample and a reagent) under certain conditions (e.g., temperature, concentration, pH) for a specific period of time. In some such embodiments, the sensitivity and/or specificity of the assay may depend on achieving the requisite degree of incubation and/or mixing prior to another step in the assay process and/or arrival at another location in the fluidic device. For example, as shown illustratively in FIGS. 7-10, a sample may comprise an analyte that is bound or otherwise associated with a molecule in the sample. The association between the analyte and the molecule may interfere with the detection of the analyte. In some such cases, the analyte may be exposed to certain reagents and/or conditions to cause dissociation of the analyte and the molecule and/or prevent re-association. The exposure time may influence the amount of free analyte that is available for detection. In some embodiments, a fluidic device designed to allow for controlled incubation may have improved sensitivity and/or specificity compared to conventional fluidic devices.

A non-limiting example of an assay comprising an incubation step that may be performed in the fluidic device, as described herein, is shown in FIGS. 7A-7D. In some embodiments, a sample 150 containing an analyte 155 associated with a molecule 160 may be analyzed in a fluidic device 140 comprising an incubation channel 165 in fluid communication with a reaction area/analysis region 170 comprising a binding partner 175 for the analyte. The assay may comprise incubating the sample with a reagent 180. The reagent may, for example, be capable of dissociating the analyte from the molecule. It should be appreciated, however, that the reagent may have different functions in other embodiments. For instance, in some embodiments, the reagent may be a component of an immune reaction (e.g., detector antibody), a component of a chemical reaction (e.g., reducing agent for a silver amplification reaction), a buffer, a diluent, a preservative for one or more component in the sample (e.g., anticoagulant), and/or combinations thereof.

In some instances, the reagent may be deposited on at least a portion of the surface of the incubation channel 165 as illustrated in FIG. 7A. The reagent may be deposited on the surface of the incubation channel prior to introduction of the sample into the device and/or may be stored in the incubation channel prior to first use. Introduction of sample or another liquid into the incubation channel may cause at least a portion of the reagent to be dissolved, reconstituted, and/or suspended in the sample as illustrated in FIG. 7B. In other embodiments, the sample or a liquid may be combined with the reagent during collection of the sample and/or prior to introduction of the sample or liquid into the incubation channel of the fluidic device. For instance, the reagent may be contained in the sample collector used to collect the sample and/or used to introduce the sample into the fluidic device (e.g., deposited on at least a portion of the surface of a channel within the sample collector). Regardless of when the reagent and the sample or another liquid are combined, incubation, e.g., of the sample and/or sample component and the reagent, may occur in the incubation channel as shown in FIG. 7B.

As used herein, "prior to first use" of the device means a time or times before the device is first used by an intended user after commercial sale. First use may include any step(s) requiring manipulation of the device by a user. For example, first use may involve one or more steps such as puncturing a sealed inlet or removing a cover from an inlet to introduce a reagent into the device, connecting two or more channels to cause fluid communication between the channels, preparation of the device (e.g., loading of reagents into the device) before analysis of a sample, loading of a sample onto or into the device, preparation of a sample in a region of the device, performing a reaction with a sample, detection of a sample, etc. First use, in this context, does not include manufacture or other preparatory or quality control steps taken by the manufacturer of the device. Those of ordinary skill in the art are well aware of the meaning of first use in this context, and will be able easily to determine whether a device of the invention has or has not experienced first use. In one set of embodiments, devices of the invention are disposable after first use, and it is particularly evident when such devices are first used, because it is typically impractical to use the devices at all after first use.

In some embodiments, the incubation step may require the reagent to be incubated with the sample, a sample component, or a liquid for a certain period of time and/or under certain conditions (e.g., temperature). For example, as illustrated in FIG. 7C, the reagent may cause the analyte to be released from the molecule by competitively associating with the molecule. In some such embodiments, the substantial dissociation of the analyte from the molecule may require a certain amount of time. In some instances, the reagent may need to be incubated with the analyte at a specific temperature or pH to increase the rate of dissociation and/or association. The incubation channel and/or feedback system may allow incubation to occur for a controlled period of time and/or temperature before a substantial portion of the sample reaches the incubation channel and/or is involved in a subsequent assay step as illustrated in FIG. 7C. After the desired incubation has occurred, the sample may flow to the reaction area, where the free analyte may bind to its binding partner (FIG. 7D).

In one set of embodiments, a fluidic device described herein may be suitable for performing an assay involving vitamin D. Vitamin D exists in blood in several forms, including bound to vitamin D binding protein (VDBP) (e.g., ~90%), bound to other carrier proteins such as albumin (e.g., ~9%), and unbound or free form (e.g., ~1%). Typically, an accurate measurement of the amount of vitamin D present in blood should be able to detect vitamin D initially present in these and/or other forms.

Competitive immunoassays are one method of measuring the content of biologically-relevant molecules, or analytes. In one embodiment of this method, the solution of interest is exposed to a known amount of antibodies (e.g., labeled antibodies) for the target analyte. The resultant mixture is then introduced to an excess of analytes (e.g., immobilized analytes) to which the free antibodies can bind. After this step, the analyte- and antibody-containing solution is washed away and the amount of antibodies bound to immobilized analytes can be detected using, e.g., colorimetric, luminescent, chemiluminescent, electrochemiluminescent, fluorescent, time-resolved fluorescent, or radioactive assays. Because the initial amount of antibody is known, the amount of antibodies bound to the analyte present in the initial sample can be calculated and thus the analyte content in the initial solution can be determined. For this assay to yield accurate information, all, or substantially all, of the analyte in the solution or sample of interest should be available for binding, i.e., it should be unbound to any binding entity that would make it difficult or impossible for the analyte to bind with a known antibody used for detection (e.g., a labelled antibody). For this reason, it can be challenging to perform accurate assays for highly bound analytes, such as vitamin D in blood, because vitamin D has a high affinity for its binding protein.

In another embodiment of a method of measuring the content of biologically-relevant molecules or analytes, the solution of interest (e.g., sample) is exposed to a known amount of exogenous Vitamin D, such as labeled Vitamin D. The resultant mixture is then introduced to a limited quantity of anti-Vit-D antibodies (e.g., immobilized antibodies) and/ or fragments thereof to which both the Vitamin D from the solution of interest and the exogenous Vitamin D (added labeled Vitamin D) can compete for binding. After this step, the Vitamin-D- and labeled Vitamin-D-containing solution is washed away and the amount of exogenous Vitamin D (e.g., labeled Vitamin D) bound to immobilized anti-Vit-D-antibodies and/or fragments thereof can be detected using, e.g., colorimetric, luminescent, chemiluminescent, electrochemiluminescent, fluorescent, time-resolved fluorescent, or radioactive assays. Because the initial amount of exogenous Vitamin D (e.g., labeled Vitamin D) is known, the amount of exogenous Vitamin D not captured by the antibody can be calculated and is a function of the endogenous Vitamin D analyte originally present in the solution of interest. For this assay to yield accurate information, all, or substantially all, of the analyte in the solution or sample of interest should be available for binding, i.e., it should be unbound to any binding entity that would make it difficult or impossible for the analyte to bind with the antibody used for capture. For this reason, it can be challenging to perform accurate assays for highly bound analytes, such as vitamin D in blood, because vitamin D has a high affinity for its binding protein.

In some embodiments, anti-Vit-D antibody fragments that include only a single binding site for vitamin D on each fragment, are used.

Releasing vitamin D from its binding proteins can be challenging due to its high binding affinities for VDBP and albumin (estimated to be $7*10^8$ $M^{-1}$ and $6*10^5$ $M^{-1}$, respectively). While it is possible to release vitamin D from albumin by pretreatment steps comprising dilution, exposure to mild detergent, and/or displacement of vitamin D with an anti-vit-D antibody and/or fragments thereof, release of vitamin D from VDBP is typically more challenging. Certain existing methods for VDBP release typically rely upon the use of harsh treatments such as incubating the serum with organic solvents, strong acids, strong bases, or performing an enzymatic digestion. Certain existing release agents include ethanol, methanol, acetonitrile, aniline sulfonic acid, triethanolamine, ethylene glycol and enzymes such as pepsin. Certain commercial assays rely on either extraction using organic solvent (e.g., acetonitrile) or a dilution step of the sample with a release cocktail that can denature the VDBP to achieve release. These steps are typically performed at room temperature for bench-top assay kits, or near 37 C for random access instruments. In some cases, certain harsh conditions (e.g., some alkaline pH treatments) are sufficiently chaotropic to also denature the detection antibodies (e.g., anti-vit-D antibodies and/or fragments thereof) which require a properly folded structure for the assay to function properly. Accordingly, the release steps in certain existing methods typically take place in the absence of the detection antibodies, and/or the reagents used for the release steps are removed before subjecting the released vitamin D to the detection antibody. Additionally, certain assays require a relatively long incubation time (e.g., at least 30 mins) to achieve release.

The release methods used in certain commercial assays described above are generally difficult to implement or may not be desirable in a point-of-care test format, such as in certain fluidic devices described herein. The harsh treatment to denature VDBP is likely to result in lysis of blood cells, negatively affecting sample quality. For milliliter- or microliter-scale samples, manual solvent extraction and sequential addition of reagents are generally incompatible with work flow and the normal skills sets of intended users. Multiple dilutions of samples can also be challenging due to normal variations in hematocrit for different patients. The implementation of these and other steps in a fluidic device may require an increase in cost and complexity of the system, and may present additional technological challenges such as possible clogs due to cell debris (e.g., due to denaturation of proteins). Moreover, point-of-care applications would benefit from an assay format where unprocessed blood can be introduced into the test system without the need to first obtain plasma or serum and where the operator has minimal input after initiating the detection assay.

The fluidic systems and methods presented in some embodiments described herein represent a substantial improvement in vitamin D assay technology by, for example, incorporating the use of heat treatment and/or release agents, and in some embodiments transfer molecules, to rapidly release vitamin D from VDBP under mild conditions.

As described herein, in one particular set of embodiments, a fluidic device may be suitable for performing an assay involving vitamin D. For instance, the fluidic device may be used to determine the amount of vitamin D in a sample such as whole blood, plasma, or serum. For example, the sample may be capillary whole blood or venous blood anti-coagulated with EDTA, citrate or heparin. In some embodiments, the fluidic device comprises several components or parts, including, for example, a release agent contained in at least one fluidic channel. The release agent may be adapted and arranged to release a vitamin D molecule from a vitamin D binding protein. The fluidic device may also include an anti-vit-D antibody and/or fragments thereof (e.g., a metal-particle labelled anti-vit-D antibody and/or fragments thereof) contained in at least one fluidic channel. In certain embodiments, at least one fluidic channel of the fluidic device is a fluidic microchannel (e.g., a channel having at least one cross-sectional dimension of less than 1 mm). In other embodiments, larger channels may be used. The fluidic device may also include a detection zone for determining an amount of vitamin D (e.g., endogenous vitamin D) in a sample. For example, in some embodiments, the detection zone may include immobilized vitamin D (e.g., exogenous vitamin D attached to a solid surface, such as a surface of a channel in the detection zone) or immobilized anti-vitamin D antibody and/or fragments thereof (e.g., Vitamin D antibody and/or fragments thereof attached to a solid surface, such as a surface of a channel in the detection zone). Additional components may also be present as described herein.

In some embodiments, a method involving the release of vitamin D (e.g., endogenous vitamin D) may be performed in a fluidic device or system described herein. The method may comprise, for example, introducing a sample into a fluidic device comprising at least one microfluidic channel, wherein the sample comprises vitamin D bound to a vitamin D binding protein. The method may involve exposing the sample to the release agent and releasing the vitamin D from the vitamin D binding protein. In some cases the release step takes place in an incubation channel and may optionally involve an incubation step. For instance, the sample and other reagents (e.g., release agent, buffer) may be incubated in the incubation channel at a reduced flow rate for a certain period of time. The method may also involve determining an amount of vitamin D (e.g., endogenous vitamin D) in the sample, e.g., both free vitamin D (e.g., vitamin D that is not bound to any binding protein) and vitamin D that was previously bound to a binding entity such as vitamin D binding protein and/or albumin. In some embodiments, one or more of the steps of vitamin D release and detection may occur in a microfluidic channel. For example, at least one, or each, of the exposing, releasing, and determining steps may take place in a microfluidic channel.

As described herein, a fluidic device may be used to promote the release of vitamin D from a carrier protein. This carrier protein may be vitamin D binding protein, albumin, or a different carrier protein. Combinations of carrier proteins (e.g. vitamin D binding protein and albumin) are also possible. The determination of the amount of vitamin D in a sample may comprise a determination of both free vitamin D and vitamin D that was previously bound to a vitamin D binding protein.

In some embodiments, a competitive assay format may be used to determine the amount of vitamin D in a sample. For example, any released vitamin D and free vitamin D may bind to a fraction of the anti-vitamin D antibodies and/or fragments thereof (e.g., labelled anti-vit-D antibodies and/or fragments thereof) during or after the release step. An excess of anti-vitamin D antibodies (e.g., labeled antibodies) and/or fragments thereof may be present in the assay/device such that the remainder of the anti-vitamin D antibodies (e.g., labeled antibodies) and/or fragments thereof are unbound and can bind to vitamin D that may be immobilized in the detection zone. In such embodiments, the concentration of vitamin D in the initial sample (e.g., released vitamin D and free vitamin D) is inversely proportional to the measured signal level of the immobilized labeled anti-vitamin D antibodies and/or fragments thereof in the detection zone. In some embodiments, a fixed quantity of exogenous Vitamin D such as tagged Vitamin D (e.g., labeled Vitamin D) may be present in the assay/device (e.g., stored in the device, as described herein) such that the exogenous Vitamin D (e.g., tagged Vitamin D) competes with the sample's Vitamin D to bind to anti-vitamin D antibody and/or fragments thereof that may be immobilized in the detection zone. In such embodiments, the concentration of vitamin D (e.g., endogenous vitamin D) in the initial sample (e.g., released vitamin D and free vitamin D) is inversely proportional to the measured signal level of the exogeneous Vitamin D (e.g., tagged Vitamin D) captured in the detection zone. In some embodiments, silver amplification chemistry is used to enhance a signal as described herein.

In some embodiments, reagents that may be used for the release and/or detection of vitamin D may be stored in the fluidic device. For example, one or more of a release agent, a buffer, a detection entity (e.g., a nanoparticle-labelled detection antibody such as anti-vit-D antibody and/or fragments thereof, a secondary antibody, exogenous Vitamin D such as tagged Vitamin D (e.g., labeled Vitamin D)) may be stored in the fluidic device. The reagent(s) may be stored in the device prior to first use of the device and/or prior to addition of the sample into the device. The release agent may be stored in any suitable form. For example, the reagent may be wet (e.g., in the form of a liquid or a solution), or dry/substantially dry. In some embodiments, the reagent is a lyophilized solid which may or may not be reconstituted upon addition to the sample or other reagent (e.g., buffer). In certain embodiments, the reagent is a coating on a channel (e.g., a coating in an analysis region, or a coating in a detection zone).

In some embodiments, a fluidic channel containing the release agent comprises an inlet and an outlet, a seal covering the inlet, and a seal covering the outlet so as to store the release agent in the fluidic device. In some embodiments, the device (e.g., a fluidic channel of the device) contains anti-vit-D antibody and/or fragments thereof. In some embodiments, the fluidic channel containing the anti-vit-D antibody and/or fragments thereof comprises an inlet and an outlet, a seal covering the inlet, and a seal covering the outlet so as to store the anti-vit-D antibody and/or fragments thereof in the fluidic device. In some embodiments, the release agent is stored in the same channel as the anti-vit-D antibody and/or fragments thereof. For instance, the release agent and the anti-vit-D antibody and/or fragments thereof may be in fluid communication with one another during storage. In some such embodiments, the release agent and the anti-vit-D antibody and/or fragments thereof are separated from one another by at least one air plug. For example, in certain embodiments, a first fluid (e.g., a first liquid) comprises the release agent and a second fluid (e.g., a second liquid) comprises the anti-vit-D antibody and/or fragments thereof. The first and second fluids may be separated by a third fluid, which may be immiscible with the first and second fluids. For example, the third fluid may be a gas or a hydrophobic liquid. In other embodiments, the release agent and the anti-vit-D antibody or fragments thereof may be present in the same fluid during storage. In yet other embodiments, the release agent and the anti-vit-D antibody and/or fragments thereof may be stored in separate channels. For example, in some embodiments the release agent and the anti-vit-D antibody and/or fragments thereof are not in fluid communication with one another during storage. In some embodiments, the fluids can be in fluid communication with one another upon piercing one or more seals of the inlet and/or outlet of the channel(s). Other configurations are also possible.

As described above, in some embodiments, a fluidic channel containing the release agent comprises an inlet and an outlet, a seal covering the inlet, and a seal covering the outlet so as to store the release agent in the fluidic device. In some embodiments, the device (e.g., a fluidic channel of the device) contains exogenous Vitamin D, such as tagged/labelled Vitamin D. In some embodiments, the fluidic channel containing the exogenous Vitamin D (e.g., tagged/labelled Vitamin D) comprises an inlet and an outlet, a seal covering the inlet, and a seal covering the outlet so as to store the exogenous Vitamin D (e.g., tagged/labelled Vitamin D) in the fluidic device. In some embodiments, the release agent is stored in the same channel as the exogenous Vitamin D (e.g., tagged/labelled Vitamin D.) For instance, the release agent and the exogenous Vitamin D (e.g., tagged/labelled Vitamin D) may be in fluid communication with one another during storage. In some such embodiments, the release agent and the exogenous Vitamin D (e.g., tagged/labelled Vitamin D) are separated from one another by at least one air plug. For example, in certain embodiments, a first fluid (e.g., a first liquid) comprises the release agent and a second fluid (e.g., a second liquid) comprises the exogenous Vitamin D (e.g., tagged/labelled Vitamin D). The first and second fluids may be separated by a third fluid, which may be immiscible with the first and second fluids. For example, the third fluid may be a gas or a hydrophobic liquid. In other embodiments, the release agent and the exogenous Vitamin D (e.g., tagged/labelled Vitamin D) may be present in the same fluid during storage. In yet other embodiments, the release agent and the exogenous Vitamin D (e.g., tagged/labelled Vitamin D) may be stored in separate channels. For example, in some embodiments the release agent and the exogenous Vitamin D (e.g., tagged/labelled Vitamin D) are not in fluid communication with one another during storage. In some embodiments, the fluids can be in fluid communication with one another upon piercing one or more seals of the inlet and/or outlet of the channel(s). Other configurations are also possible.

Other reagents or combinations of reagents may also be stored in the fluidic system as described herein. For example, in some embodiments silver amplification reagents may be stored together with (e.g., in fluid communication with) the vitamin D assay reagents (e.g., anti-vit-D antibody and/or fragments thereof or exogenous Vitamin D such as tagged/labelled Vitamin D) in a fluidic device. In some embodiments, the two sets of reagents may be separated by an immiscble fluid (e.g., a gaseous plug or a hydrophobic plug).

In other embodiments, silver amplification reagents may be stored separately from (e.g., not in fluid communication with) the vitamin D assay reagents (e.g., anti-vit-D antibody and/or fragments thereof or exogenous Vitamin D such as tagged/labelled Vitamin D) in a fluidic device. For example, the silver amplification reagents may be stored in separate channels from the vitamin D assay reagents (e.g., anti-vit-D antibody and/or fragments thereof or exogenous Vitamin D such as tagged/labelled Vitamin D) in a fluidic device.

In certain embodiments in which both silver amplification reagents and vitamin D assay reagents (e.g., anti-vit-D antibody and/or fragments thereof or exogenous Vitamin D such as tagged/labelled Vitamin D) are stored in a fluidic device, the silver amplification reagents may be positioned upstream of the vitamin D assay reagents with respect to the direction of fluid flow/intended fluid flow during operation of the device. In some cases, the two sets of reagents may be separated by an immiscble fluid (e.g., a gaseous plug or a hydrophobic plug). Other configurations are also possible.

As described herein, in some embodiments, one or more of the channels of a fluidic device or system may be microfluidic channels (e.g., channels having at least one cross-sectional dimension of less than 1 mm). For example, in some cases at least one, both, or all of the fluidic channel containing (e.g., storing) the release agent and the fluidic channel containing the anti-vit-D antibody and/or fragments thereof or the exogenous Vitamin D (e.g., tagged/labelled Vitamin D) may be microfluidic channels. The channel(s) in the detection zone (e.g., a detection channel) may be microfluidic in some embodiments. Other configurations are also possible.

In some embodiments, a fluidic device is designed to perform a vitamin D assay under conditions that measure the bioavailable vitamin D (e.g., in a sample). Bioavailable vitamin D, as used herein, refers to the vitamin D (e.g., endogenous vitamin D) that is either free in solution or bound to proteins other than the vitamin D binding protein (for example, bound to albumin). Because the affinity between Vitamin D and proteins other than vitamin D binding protein is weaker than the affinity between Vitamin D and the vitamin D binding protein, conditions suitable for releasing bioavailable vitamin D (e.g., detergent type, detergent concentration, temperature/time of release) may be milder than those for releasing all the vitamin D. When using whole blood as a matrix, and a fluidic device as a platform to perform the immunoassay, the use of mild release conditions may be attractive so that deterioration of the sample (e.g., blood) during the release step may be reduced or avoided. Such sample deterioration can result in poor flow performance of the treated blood inside channels (e.g., microchannels) and/or other outcomes that may contribute to inaccurate results. In some embodiments, bioavailable vitamin D may be measured in a fluidic device comprising a detection zone. In some embodiments, the selection of the release conditions can be tailored such that substantially all (e.g., at least 95%, at least 97%, at least 99%) of the red blood cells in the sample do not lyse or aggregate until at least completion of the flow of the sample over the detection zone has occurred.

In some embodiments involving a vitamin D assay (e.g., in a fluidic device), at least a portion of the sample (or a reagent) is incubated in an incubation channel for a period of time. As described herein, the flow of the sample may be stopped, or the flow rate reduced, during the incubation step. For example, in some embodiments, a sample or reagent may be incubated (e.g., in an incubation channel and/or a portion of a detection channel described herein) for a time of at least 1 minute, at least 3 minutes, at least 5 minutes, at least 7 minutes, at least 9 minutes, at least 11 minutes, at least 13 minutes, at least 15 minutes, at least 17 minutes, at least 19 minutes, at least 20 minutes, at least 30 minutes, at least 40 minutes, at least 50 minutes, at least 60 minutes. The time may be less than or equal to 60 minutes, less than or equal to 50 minutes, less than or equal to 40 minutes, less than or equal to 30 minutes, less than or equal to 20 minutes, less than or equal to 19 minutes, less than or equal to 17 minutes, less than or equal to 15 minutes, less than or equal to 13 minutes, less than or equal to 12 minutes, less than or equal to 11 minutes, less than or equal to 10 minutes, less than or equal to 9 minutes, less than or equal to 7 minutes, less than or equal to 5 minutes, less than or equal to 3 minutes, or less than or equal to 1 minute. Combinations of the above-referenced ranges are also possible (e.g. at least 5 minutes and less than or equal to 15 minutes). Other ranges are also possible.

A sample or reagent may be incubated at any suitable temperature. In some embodiments, a sample or reagent may be incubated (e.g., in an incubation channel and/or a portion of a detection channel described herein) at a temperature (e.g., an incubation temperature) of at least 15° C., at a temperature of at least 20° C., at a temperature of at least 25° C., at least 30° C., at least 35° C., at least 40° C., at least 45° C., at least 50° C., at least 55° C., or at least 60° C. The temperature may be less than or equal to 65° C., less than or equal to 60° C., less than or equal to 55° C., less than or equal to 50° C., less than or equal to 45° C., less than or equal to 40° C., less than or equal to 35° C., less than or equal to 30° C., or less than or equal to 25° C. Combinations of the above-referenced ranges are also possible (e.g., at least 45° C. and less than or equal to 55° C.). Other ranges are also possible.

A sample or reagent may be diluted into a buffer of any suitable pH. In some embodiments, the sample or reagent may be diluted into a buffer with an acidic or basic pH. In some embodiments, a sample or reagent may be diluted into a buffer with a pH of at least 1.0, at least 1.5, at least 2.0, at least 2.5, at least 3.0, at least 3.5, at least 4.0, at least 4.5, at least 5.0, at least 5.25, at least 5.5, at least 5.75, at least 6.0, at least 6.5, at least 7.0, at least 7.5, at least 8.0, at least 8.5, at least 9.0, at least 9.5, at least 10.0, at least 10.5, at least 11.0, at least 11.5, at least 12.0, or at least 12.5. The pH of the buffer may be less than or equal to 13.0, less than or equal to 12.5, less than or equal to 12.0, less than or equal to 11.5, less than or equal to 11.0, less than or equal to 10.5, less than or equal to 10.0, less than or equal to 9.5, less than or equal to 9.0, less than or equal to 8.5, less than or equal to 8.0, less than or equal to 7.5, less than or equal to 7.0, less than or equal to 6.5, less than or equal to 6.0, less than or equal to 5.75, less than or equal to 5.5, less than or equal to 5.25, or less than or equal to 5.0. Combinations of the above-referenced ranges are also possible (e.g., pH of at least 5.0 and less than or equal to 9.0). Other ranges are also possible. The pHs described above may independently be a first pH or a second pH described herein.

In some embodiments, a sample or reagent may be diluted into a first buffer having a pH as described above (e.g., a first pH), and then a second buffer with a suitable pH (e.g., a second pH) different from (e.g., less than or greater than) a pH of the first buffer. In some embodiments, a sample or reagent may be diluted into a second buffer with a pH (e.g., second pH) of at least 5.0, at least 5.25, at least 5.5, at least 5.75, at least 6.0, at least 6.5, at least 7.0, at least 7.5, at least 8.0, at least 8.5, or at least 9.0. The pH (e.g., second pH) of the second buffer may be less than or equal to 9.0, less than or equal to 8.5, less than or equal to 8.0, less than or equal to 7.5, less than or equal to 7.0, less than or equal to 6.5, less than or equal to 6.0, less than or equal to 5.75, less than or equal to 5.5, less than or equal to 5.25, or less than or equal to 5.0. Combinations of the above-referenced ranges are also possible (e.g., pH of at least 5 and less than or equal to 9). Other ranges are also possible.

In some embodiments, a sample or reagent may be diluted into a first buffer having a first pH as described above, and then a second buffer with a second pH as described above, followed by exposure to an antibody or other suitable binding entity.

In some embodiments, at least a portion of the sample is exposed to a release agent for a period of time. As described herein, the flow of the sample may be stopped, or the flow rate reduced, during the release step. For example, in some embodiments, a sample may be exposed to a release agent (e.g., in a portion of a detection channel described herein) for a time of at least 1 minute, at least 3 minutes, at least 5 minutes, at least 7 minutes, at least 9 minutes, at least 11 minutes, at least 13 minutes, at least 15 minutes, at least 17 minutes, at least 19 minutes, at least 20 minutes, at least 30 minutes, at least 40 minutes, at least 50 minutes, at least 60 minutes. The time may be less than or equal to 60 minutes, less than or equal to 50 minutes, less than or equal to 40 minutes, less than or equal to 30 minutes, less than or equal to 20 minutes, less than or equal to 19 minutes, less than or equal to 17 minutes, less than or equal to 15 minutes, less than or equal to 13 minutes, less than or equal to 12 minutes, less than or equal to 11 minutes, less than or equal to 10 minutes, less than or equal to 9 minutes, less than or equal to 7 minutes, less than or equal to 5 minutes, less than or equal to 3 minutes, or less than or equal to 1 minute. Combinations of the above-referenced ranges are also possible (e.g. at least 5 minutes and less than or equal to 15 minutes). Other ranges are also possible.

The sample or reagent may comprise any suitable fluid. In some embodiments, the sample or reagent may comprise whole blood, serum, or plasma. Other fluids are also possible.

A sample or a reagent may be diluted to any suitable degree. In some cases, the dilution step may occur in a fluidic device (e.g., in a channel of a microfluidic device). In some embodiments, a sample or reagent may be diluted to a degree (e.g., as a percent of the final volume that contains the diluent) of at least 0 vol % (undiluted), at least 10 vol %, at least 20 vol %, at least 30 vol %, at least 40 vol %, at least 50 vol %, at least 60 vol %, at least 70 vol %, at least 80 vol %, at least 90 vol %, at least 95 vol %, at least 98 vol %, or at least 99 vol % (diluted at a 1:100 ratio). The dilution degree may be less than or equal to 99 vol %, less than or equal to 98 vol %, less than or equal to 95 vol %, less than or equal to 90 vol %, less than or equal to 80 vol %, less than or equal to 70 vol %, less than or equal to 60 vol %, less than or equal to 50 vol %, less than or equal to 40 vol %, less than or equal to 30 vol %, less than or equal to 20 vol %, less than or equal to 10 vol %. Combinations of the above-referenced ranges are also possible (e.g. at least 0 vol % and less than or equal to 90 vol %). Other ranges are also possible.

A sample or reagent may be exposed to any suitable release agent. In some cases, the sample or reagent may be exposed to the release agent in a channel of a fluidic device (e.g., in a microfluidic channel of a microfluidic device). The release agent may be a detergent in some embodiments; for example, a non-ionic detergent, an anionic detergent, or a cationic detergent. In some cases, the release agent may comprise a carboxyl head group and a fluorinated or non-fluorinated carbon chain. In other cases, the release agent may comprise an amine oxide head group and a fluorinated or non-fluorinated carbon chain. Fluorinated carbon chains may be perfluorinated or non-perfluorinated. In some embodiments, the release agent may comprise one or more of a molecule having a betaine head group, such as a betaine head group with fluorinated (e.g., perfluoroalkyl or fluorinated alkyl) and/or hydrocarbon side chains (e.g., FS50), a perfluoroalkyl amine oxide (e.g., FS51), N,N-Dimethyl-N-dodecylglycine betaine (Empigen BB), or a fluorinated/perfluorinated acid (e.g., perfluorooctanoic acid, perfluorohexanoic acid).

In some embodiments, a release agent includes a fluorinated species, which includes a carbon chain (e.g., a fluorinated alkyl). In some embodiments, the release agent or fluorinated species may comprise or have the formula $-C_nF_mR_y$, where n is an integer between 6 and 18, m is an integer greater than 1, R is either zero, an atom, or a group of atoms (e.g., hydrogen, oxygen, sulfur, nitrogen, carbon or an endgroup described herein), and y is an integer greater than or equal to 0. In some embodiments, n is at least 6, at least 8, at least 10, at least 12, at least 14, or at least 16. In some cases, n is less than or equal to 16, is less than or equal to 14, is less than or equal to 12, is less than or equal to 10, or is less than or equal to 8. Combinations of the above-referenced ranges are also possible. In some embodiments, m is at least 2, at least 4, at least 8, at least 12, at least 16, at least 20, at least 24, at least 28, or at least 30. In some cases, m is less than or equal to 32, less than or equal to 28, less than or equal to 24, less than or equal to 20, is less than or equal to 16, is less than or equal to 12, is less than or equal to 8, or is less than or equal to 4. Combinations of the above-referenced ranges are also possible. The fluorinated species may comprise, for example, the formula $-C_8F_{15}H_2$, $-C_8F_{16}H_1$, $-C_8F_{17}$, or $-C_6F_{13}$. The chain may include, in some embodiments, the formula $-C_nF_{2n+1}$. The fluorinated carbon chain may be a side chain of a molecule in some embodiments. The release agent may include one or more endgroups or head groups described herein.

In some embodiments, a release agent includes a hydrocarbon chain (e.g., an alkyl). In some embodiments, the release agent or hydrocarbon chain may comprise or have the formula $-C_nH_mR_y$, where n is an integer between 6 and 18, m is an integer greater than 1, R is either zero, an atom, or a group of atoms (e.g., hydrogen, oxygen, sulfur, nitrogen, carbon or an endgroup described herein), and y is an integer greater than or equal to 0. In some embodiments, n is at least 6, at least 8, at least 10, at least 12, at least 14, or at least 16. In some cases, n is less than or equal to 16, is less than or equal to 14, is less than or equal to 12, is less than or equal to 10, or is less than or equal to 8. Combinations of the above-referenced ranges are also possible. In some embodiments, m is at least 2, at least 4, at least 8, at least 12, at least 16, at least 20, at least 24, at least 28, or at least 30. In some cases, m is less than or equal to 32, less than or equal to 28, less than or equal to 24, less than or equal to 20, is less than or equal to 16, is less than or equal to 12, is less than or equal to 8, or is less than or equal to 4. Combinations of the above-referenced ranges are also possible. The release agent or carbon chain may comprise, for example, the formula $-C_8H_{17}$ or $-C_6H_{13}$. The chain may include, in some embodiments, the formula $-C_nH_{2n+1}$. The hydrocarbon chain may be a side chain of a molecule in some embodiments. The release agent may include one or more endgroups or head groups described herein.

In some cases, a release agent may have a combination of one or more (e.g., two) hydrocarbon chain(s) comprising or having the formula $-C_nH_mR_y$ (e.g., $C_6H_{13}$) and one or more fluorinated species that includes a carbon chain comprising or having the formula $-C_nF_mR_y$ (e.g., $C_6F_{13}$), where n, m, R and y are defined herein. For example, the hydrocarbon and/or fluorinated carbon chains may be present on an —N— or —N+— containing group in some cases. In some cases, the release agent may also include an endgroup described herein (e.g., a carboxylate group).

In certain embodiments, a release agent includes one or more carbon chains (e.g., $C_n$, where n is at least 6), in which at least some of the hydrogen atoms of the carbon chain(s) is/are replaced by fluorine atoms. For example, in some embodiments, at least 10%, at least 20%, at least 30%, at least 40%, at least 50%, at least 60%, at least 70%, at least 80%, at least 90%, or at least 95% of the total number of hydrogen atoms of the carbon chain(s) is/are replaced by fluorine atoms. In some cases, less than or equal to 100%, less than or equal to 80%, less than or equal to 60%, less than or equal to 40%, or less than or equal to 20% of the total number of hydrogen atoms of the carbon chain(s) is/are replaced by fluorine atoms. Combinations of the above-referenced ranges are also possible. In some cases, a carbon chain including fluorine atoms (e.g., a fluorinated species)

may comprise a fluorine to hydrogen ratio of, for example, at least 0.2:1, at least 0.5: 1, at least 1:1, at least 2:1, at least 5:1, or at least 10:1. The fluorine to hydrogen ratio may be less than or equal to 10:1, less than or equal to 5:1, less than or equal to 2:1, less than or equal to 1:1, less than or equal to 0.5:1, or less than or equal to 0.2:1. Combinations of the above-referenced ranges are also possible. Other ranges are also possible. In some cases, the fluorinated species is perfluorinated.

In some embodiments, an endgroup may be H, an alkyl, an alkenyl, an alkynyl, a heteroalkyl, a heteroalkenyl, a heteroalkynyl, a halide (e.g., a fluorine), an acyl, an aryl, a heteroaryl, or an amine, optionally substituted. In other cases, an endgroup may be a carboxyl, a carbonyl, a carboxylic acid, a carboxylate, a thiolcarbonyl, a thioester, a thioether, a thiolcarboxylic acid, an aldehyde, a ketone, an alkoxy, an aryloxy, an acyloxy, an aralkyl, an arylalkyl, a heterocycle, an amino, an amine oxide, a methylol, a hydroxyalkyl, a mercaptoalkyl, a hydrocarbon, an isocyanate, a sulfate, a phosphate, an ester, an ether, a silane, a urethane, a carbonate, a thiol, a hydroxide, or a thiolurethane, optionally substituted. An endgroup may be charged (e.g., anionic or cationic) or uncharged.

In certain embodiments, a release agent may be a competitor of vitamin D for the binding pocket of the VDBP. For example, the release agent may be a small molecule that resembles vit-D enough to bind to the VDBP, and different enough to not cross-react with the anti-vitamin D antibodies and/or fragments thereof. Other release agents and combinations of release agents are also possible. In certain embodiments, a release agent is chosen to allow the release step to take place in an aqueous solvent (e.g., aqueous solution or suspension, such as in water or a buffer).

The particular release agent (e.g., such as a detergent or other species described herein) may be chosen based, at least in part, on its ability to not denature the other reagents or components used in the assay (e.g., anti-vit-D antibodies and/or fragments thereof, vitamin D (exogenous vitamin D or exogenous vitamin D), tagged/labelled vitamin D, vit-D-binding protein, detection antibodies (e.g., primary or secondary detection antibodies) and/or fragments thereof). For example, in some embodiments, the release agent is not an enzyme (e.g., not one of pepsin, trypsin, or proteinase K), not a an organic solvent (e.g., not one of BME, DMF, acetonitrile, ANS, SDS), not a reducing agent, not an acid (e.g., not one of acetic acid, malonic acid, citric acid), and/or not a surfactant (e.g., not a perfluoro-acid). Accordingly, in some embodiments, a method described herein may allow release of vitamin D from its binding protein (e.g., vit-D binding protein) in the presence of a detection antibody and/or fragments thereof (e.g., anti-vit-D-antibody and/or fragments thereof). For instance, in some cases the release of vitamin D from its binding protein may take place without further purification or solvent-removal steps before the released vitamin D is allowed to bind with a detection antibody and/or fragments thereof. In certain embodiments, the release of vitamin D from its binding protein may take place while the sample and/or released vitamin D is in fluid communication with the detection antibody and/or fragments thereof (e.g., anti-vit-D-antibody and/or fragments thereof).

In some embodiments, a method described herein may allow release of vitamin D from its binding protein (e.g., vit-D binding protein) in the presence of exogenous Vitamin D (e.g., tagged/labelled vitamin D). For instance, in some cases the release of vitamin D from its binding protein may take place without further purification or solvent-removal steps before the released vitamin D is allowed to compete with exogenous Vitamin D (e.g., tagged/labelled vitamin D). In certain embodiments, the release of vitamin D from its binding protein may take place while the sample and/or released vitamin D is in fluid communication with the exogenous Vitamin D (e.g., tagged/labelled vitamin D). The released vitamin D and exogenous Vitamin D (e.g., tagged/labelled vitamin D) may compete for binding with an antibody (e.g., anti-vitamin D antibody) or fragment thereof as described herein.

In some embodiments, the release agent (e.g., detergent) is present in a buffer. The release agent may be reconstituted by a buffer or directly by the sample (e.g., in embodiments in which the release agent is in solid or lyophilized form), or initially present in solution. Any suitable concentration of release agent (e.g., detergent) may be possible (e.g., upon mixing with a buffer). In some embodiments, the release agent (e.g., detergent) has a concentration of at least 0.01 wt %, at least 0.05 wt %, at least 0.1 wt %, at least 0.2 wt %, at least 0.4 wt %, at least 0.6 wt %, at least 0.8 wt %, at least 1 wt %, at least 1.2 wt %, at least 1.4 wt %, at least 1.6 wt %, at least 1.8 wt %, at least 2 wt %, at least 2.2 wt %, at least 2.4 wt %, at least 2.8 wt %, at least 3 wt %, at least 3.5 wt %, at least 4 wt %, at least 4.5 wt %, or at least 5 wt %. The release agent (e.g., detergent) concentration may be less than or equal to 5 wt %, less than or equal to 4.5 wt %, less than or equal to 4 wt %, less than or equal to 3.5 wt %, less than or equal to 3 wt %, less than or equal to 2.8 wt %, less than or equal to 2.6 wt %, less than or equal to 2.4 wt %, less than or equal to 2.2 wt %, less than or equal to 2 wt %, less than or equal to 1.8 wt %, less than or equal to 1.6 wt %, less than or equal to 1.4 wt %, less than or equal to 1.2 wt %, less than or equal to 1 wt %, less than or equal to 0.8 wt %, less than or equal to 0.6 wt %, less than or equal to 0.4 wt %, less than or equal to 0.2 wt %, or less than or equal to 0.1 wt %. Combinations of the above-referenced ranges are also possible (e.g., a concentration of at least 0.2 wt % and less than or equal to 0.6 wt %). In some embodiments, the release agent (e.g., detergent) may comprise at least one of 0.4-0.8% FS50, 0.4% FS51, and 0.4% Empigen BB. Other ranges are also possible. The release agent may have a concentration in one or more of the above-referenced ranges prior to or after being mixed with the sample. For instance, in some embodiments, the release agent may have a concentration in one or more of the above-referenced ranges after being reconstituted by a buffer in a fluidic device, and/or during storage of the reagent in the device.

The release agent may be in any suitable form. In some embodiments, the release agent may be a dried solid, a lyophilized solid, e.g., a lyophilized solid derived from a liquid solution. In some embodiments, the release agent may be a liquid (e.g., a liquid solution, such as an aqueous solution). Other forms are also possible.

A sample or release agent may, in some embodiments, be exposed to a transfer molecule. The transfer molecule may help maintain the highly hydrophobic free vitamin D in solution and/or facilitate transport of released vitamin D from VDBP to the anti-vit-D antibodies and/or fragments thereof. The transfer molecule may be a member of the beta-cyclodextrin family such as methyl-beta-cyclodextrin, or comprise an acetyl-, succinyl-(2-hydroxypropyl)-, 2-hydroxypropyl-, carboxymethyl-, sulfate, 2-hydroxyethyl, succinyl-, and/or butyl group. Other transfer molecules and combinations of transfer molecules are also possible. In some embodiments, one or more transfer molecules can be stored in a channel of a fluidic device, as described herein.

In some embodiments, a reagent contained (e.g., stored) in a fluidic device may be one or more small molecules that compete with vitamin D for binding to VDBP to prevent re-association of the released vitamin D with VDBP. The one or more small molecules that compete with vitamin D for binding to VDBP may include, for example, one or more of the following compounds:

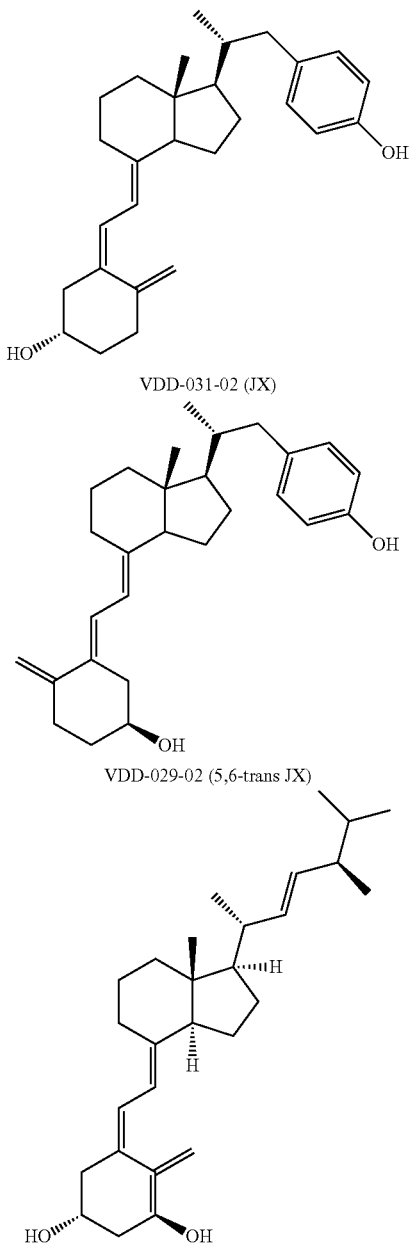

VDD-031-02 (JX)

VDD-029-02 (5,6-trans JX)

However, in other embodiments, an assay described herein is performed without such small molecules.

The sample or reagent may be exposed to a buffer containing any suitable buffering agent. In some embodiments, the buffer may be a citrate buffer, an acetate buffer, a malonate buffer, or a tris buffer. Combinations of the above-referenced buffers are also possible (e.g., an acetate-malonate buffer). Other buffers and buffer combinations are also possible.

A sample or reagent may be diluted into a buffer of any suitable concentration. In some embodiments, a sample or reagent may be diluted into a buffer with a concentration of at least1 mM, at least 5 mM, at least 10 mM, at least 20 mM, at least 30 mM, at least 40 mM, at least 50 mM, at least 60 mM, at least 70 mM, 80 mM, at least 90 mM, at least 100 mM, at least 110 mM, at least 120 mM, at least 130 mM, at least 140 mM, at least 150 mM, at least 160 mM, at least 170 mM, at least 180 mM, at least 190 mM, at least 200 mM, at least 250 mM, 300 mM, at least 350 mM, at least 400 mM, at least 450 mM, at least 500 mM, at least 550 mM, at least 600 mM, at least 650 mM, at least 700 mM, at least 750 mM, at least 800 mM, at least 850 mM, or at least 900 mM. The concentration of the buffer may be less than or equal to 900 mM, less than or equal to 850 mM, less than or equal to 800 mM, less than or equal to 750 mM, less than or equal to 700 mM, less than or equal to 650 mM, less than or equal to 600 mM, less than or equal to 550 mM, less than or equal to 500 mM, less than or equal to 450 mM, less than or equal to 400 mM, less than or equal to 350 mM, less than or equal to 300 mM, less than or equal to 250 mM, less than or equal to 200 mM, less than or equal to 190 mM, less than or equal to 180 mM, less than or equal to 170 mM, less than or equal to 160 mM, less than or equal to 150 mM, less than or equal to 140 mM, less than or equal to 130 mM, less than or equal to 120 mM, less than or equal to 110 mM, less than or equal to 100 mM, less than or equal to 90 mM, less than or equal to 80 mM, less than or equal to 70 mM, less than or equal to 60 mM, less than or equal to 50 mM, less than or equal to 40 mM, less than or equal to 30 mM, less than or equal to 20 mM, less than or equal to 10 mM, less than or equal to 5 mM, or less than or equal to 1 mM. Combinations of the above-referenced ranges are also possible (e.g., concentration of at least 50 mM and less than or equal to 150 mM). Other ranges are also possible. The buffer may have a concentration in one or more of the above-referenced ranges prior to or after being mixed with the sample. For instance, in some embodiments, the buffer may have a concentration in one or more of the above-referenced ranges during storage of the buffer in the device.

In some embodiments, the fluidic system contains a labeled molecule in a channel. This labeled molecule may be a monoclonal or polyclonal antibody that binds with vitamin D, a labeled secondary antibody (e.g., monoclonal or polyclonal antibody) that binds with a primary antibody that binds with vitamin D, or a labeled/tagged Vitamin D molecule (e.g., exogenous Vitamin D). In some embodiments, the label may be a metal particle, such as a metal nanoparticle, e.g., a gold nanoparticle. In some embodiments, the label comprises a metal nanoparticle-labeled Vitamin D, or a gold-labeled Vitamin D. In some embodiments, the labeled molecule is a gold-labeled anti-vitamin D antibody and/or gold-labeled fragments thereof, or a gold-labeled vitamin D molecule. Other labeled molecules are also possible. The labeled anti-vitamin D antibody and/or labeled fragments thereof may be in any form, including a dried solid or a lyophilized solid. The labeled vitamin D (e.g., exogenous Vitamin D) may be in any form, including a dried solid or a lyophilized solid. Other forms are also possible.

In some embodiments, vitamin D (e.g., exogenous Vitamin D) may be present (e.g., stored in a fluidic device), such as in detection zone of a fluidic device. In some embodiments, the detection zone may be coated with vitamin D (e.g., exogenous Vitamin D) covalently coupled to a binding entity. The binding entity may be, for example, a protein such as bovine serum albumin, or human IgG (or a gamma globulin fraction from human blood), or a polymer such as a polysaccharide (e.g., dextran or chemically-modified dextran such as amino dextran). Other binding entities or combination of binding entities are also possible. The vitamin D (e.g., exogenous Vitamin D) present in the device (and not derived from the sample) may be used to facilitate detection of vitamin D released/present in a sample, as described herein. In some embodiments, the vitamin D (e.g., exogenous Vitamin D) present in the device (e.g., stored in a fluidic device), and not derived from the sample, is labelled/tagged vitamin D.

In some embodiments, anti-vitamin D antibody and/or fragments thereof may be present (e.g., stored in a fluidic device), such as in detection zone of a fluidic device. For example, in some embodiments the detection zone is coated with anti-Vitamin D antibody and/or fragments thereof covalently coupled to a binding entity, or the detection zone is coated with vitamin D covalently coupled to a binding entity. Other binding entities or combination of binding entities are also possible. The anti-vitamin D antibody and/or fragments thereof present in the device (and not derived from the sample) may be used to facilitate detection of vitamin D released/present in a sample, as described herein. In some embodiments, the anti-vitamin D antibody and/or fragments thereof present in the device (e.g., stored in a fluidic device, such as in detection zone of a fluidic device), and not derived from the sample, is labelled/tagged anti-vitamin D antibody and/or labelled/tagged fragments thereof.

In some embodiments, a fluidic device having an incubation channel may have a greater sensitivity and/or specificity to an analyte compared to an essentially identical fluidic device that lacks the incubation channel. For instance, FIG. 8 shows a schematic of the assay described above with respect to FIG. 7 performed in a fluidic device 190 that comprises a channel 195 and a reaction area 200 comprising a binding partner 205 for the analyte, but lacks an incubation channel. The reagent 180 may be deposited on at least a portion of a surface of the channel as shown in FIG. 8A. In some such cases, the reagent may be deposited at a location that is relatively close (e.g., adjacent) to the sample inlet. As in FIG. 7B, the sample may dissolve or suspend the reagent in at least a portion of the sample as illustrated in FIG. 8B. In certain embodiments, due to the lack of the incubation channel coupled with the feedback system in fluidic device 190, the sample may proceed toward and arrive at the reaction area more quickly than the fluidic device comprising an incubation channel, e.g., as shown in FIG. 8C. In some such embodiments, little or no dissociation of the analyte and the molecule may have occurred by the time the sample reaches the reaction area as shown in FIG. 8D. In some embodiments, the flow rate in fluidic device 190 may not be able to be reduced to increase the duration of incubation due to its effects on fluid flow, e.g., issues with clogging.

Figure 9A:
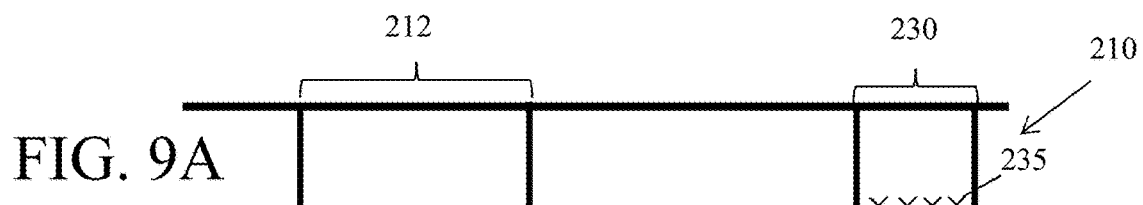
FIGS. 9A-9D show schematic diagrams of an assay comprising an incubation step in a fluidic device comprising an incubation channel according to one set of embodiments.
Figure 9B:
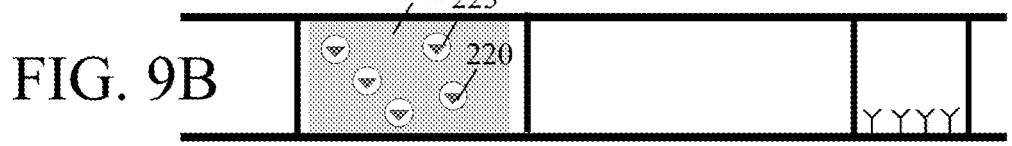
Figure 9C:
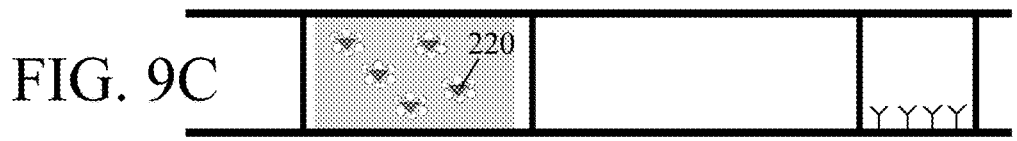
Figure 9D:
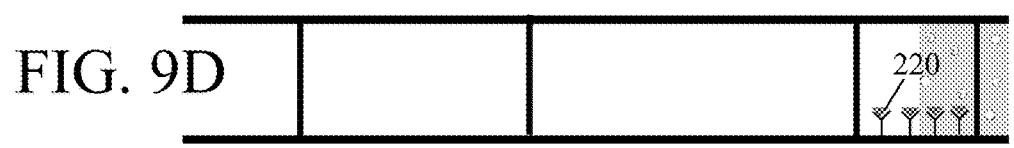

Another non-limiting example of an assay comprising an incubation step that may be performed in the fluidic device comprising an incubation channel is shown in FIGS. 9A-9D. In some embodiments, a sample 215 containing an analyte 220 associated with a molecule 225 may be analyzed in a fluidic device 210 comprising a reaction area 230 comprising a binding partner 235 for the analyte downstream of the incubation channel 212. The association between the analyte and the molecule may prevent the analyte from binding with the binding partner in the reaction area. In some such embodiments, the sample may be flowed into the incubation channel, as shown in FIG. 9B, and exposed to certain conditions to cause the analyte to dissociate from the molecule. For instance, as illustrated in FIG. 9C, the sample or sample component may be incubated at a certain pH and/or temperature that cause the molecule to degrade or denature and thereby dissociate from the analyte. In some embodiments, once the requisite incubation has occurred, the at least one condition may be altered in or outside of the incubation channel. For instance, in embodiments in which the sample is incubated at a certain temperature, the heating of the sample in the incubation channel may cease after a predetermined temperature or period of time has been met. In embodiments in which at least one condition is a chemical property, the chemical property may be changed after sufficient incubation has occurred. For instance, a sample incubated at a certain pH may be mixed with an acid and/or base to alter the pH of the sample within the incubation channel and/or prior to the sample arriving at a downstream location such as the reaction area. Mixing of assay components in the incubation channel is described in more detail below. Regardless of whether the condition(s) that the sample is exposed to in the incubation channel are altered, after the incubation step, the free analyte may be flowed to the reaction area where the analyte can bind to its binding partner (FIG. 9D).

Figure 10A:
FIGS. 10A-10D show schematic diagrams of an assay comprising an incubation step in a fluidic device lacking an incubation channel according to one set of embodiments.
Figure 10B:
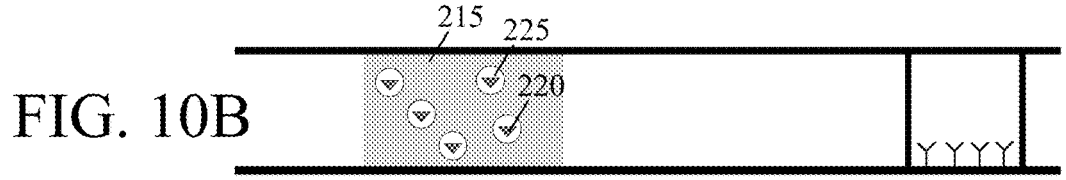
Figure 10C:

In some embodiments, the assay, described above with respect to FIG. 9, may have a reduced sensitivity and/or specificity when performed in an essentially identical fluidic device that lacks an incubation channel. For instance, FIGS. 10A-10D show a schematic of the assay performed in a fluidic device 240 that comprises a channel 245 and a reaction area 250 comprising a binding partner 235 for the analyte, but lacks an incubation channel. In some such embodiments, the sample 215 containing the analyte 220 associated with the molecule 215 may be exposed to the certain conditions and flowed along the channel as shown in FIG. 10B. In certain embodiments, due to the movement of the sample and/or lack of an incubation channel, the exposure of the sample to the condition may be limited. For instance, the mobility of the sample may prevent sufficient heating of the sample due to the inability to locally heat a moving sample. In some embodiments in which at least one condition is a chemical property (e.g., pH, reagent concentration), the requisite exposure time may not be achieved because the sample may proceed toward and arrive at the reaction area relatively quickly compared to the fluidic device comprising incubation channel, as shown in FIG. 10C.

Figure 10D:

The limited exposure of the sample to one or more condition may result in little or no dissociation of the analyte as shown in FIG. 10D. In some embodiments, prolonged exposure to certain conditions and/or maintaining those conditions throughout the assay may negatively affect the sensitivity and/or specificity of the assay. For instance, the pH used to dissociate an analyte may negatively affect the binding of the analyte to the binding partner. In some instances, prolonged exposure of an analyte to certain pHs may lead to degradation or denaturation of the analyte.

As described herein, in some embodiments, e.g., for certain assays in which the sample is capillary whole blood drawn from a finger stick, venous whole blood, or other samples matrices, the temperature and duration of incubation may cause the leading edge of the sample to dry and/or coagulate and thereby present an obstacle to resuming the flow of the sample after incubation. In such cases, it may be desirable to position the sample in the device such that the sample's leading edge (e.g., the downstream-most sample/air interface) is positioned within a channel having a relatively larger cross-section, such as the incubation channel, during the incubation step. In some such embodiments, the relatively larger cross-sectional area (e.g., of the incubation channel) will present a lesser flow restriction upon resuming flow of the sample compared to a relatively smaller cross-sectional area. Referring to the device shown in FIG. 1A, the sample leading edge can be maintained within a larger channel during incubation by, for example, applying pre-determined vacuum or pressure levels for a pre-determined time to bring the majority of the sample into the incubation channel 15 but not reach the detection channel 20 or detection zone 25, as previously described. In the device shown in FIG. 1B, detection zone 27 within the incubation channel 15 would permit the sample to be detected when it reaches this location, and the vacuum or pressure levels can be modulated as previously described in order to maintain the sample within the incubation channel, but not reach portions of the detection channel in detection zone 25, during the incubation time.

Figure 11A:
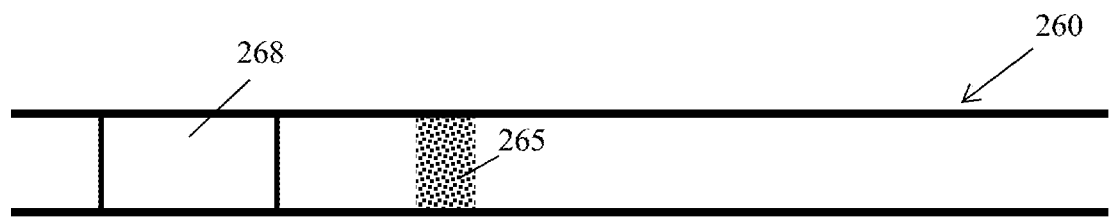
FIGS. 11A-11E show methods of mixing fluids in an incubation channel according to one set of embodiments.
Figure 11B:
Figure 11C:
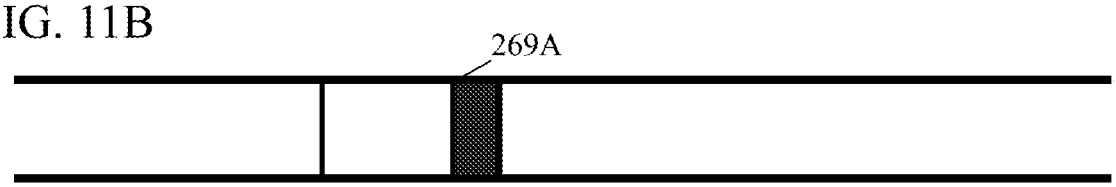
Figure 11D:
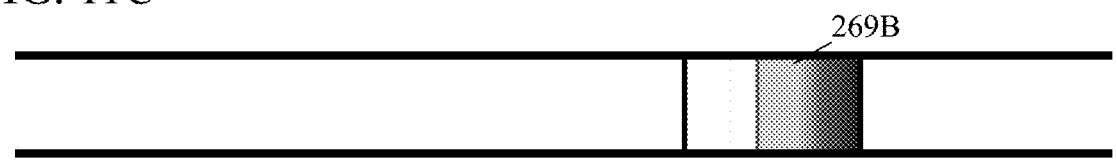
Figure 11E:

In some embodiments, the incubation channel may be used to mix two or more assay components, as illustrated in FIGS. 11A-11E. For instance, in some embodiments, a sample 268 may be introduced into an incubation channel 260 having a reagent 265 deposited on at least a portion of a surface of the incubation channel as illustrated in FIG. 11A. The sample 268 may dissolve, reconstitute and/or suspend at least a portion of the reagent as it flows along the channel as illustrated in FIG. 11B. In some instances, a concentration gradient 269A may exist within the sample after dissolving, reconstituting, or suspending the reagent as illustrated in FIG. 11C. The incubation channel may be designed to promote mixing 269B, e.g., via diffusion as the sample flows along the channel as illustrated in FIG. 11D. In some embodiments, a substantially homogenous mixture 269D of the sample and the reagent may exist prior to the sample plug exiting the incubation channel as illustrated in FIG. 11E.

In some embodiments, a method may involve mixing two or more fluids in the incubation channel of the fluidic device. In such embodiments, mixing may occur instead of or in addition to an incubation step described herein. Mixing may take place when at least some of the fluids are positioned in series in the incubation channel. For example, the fluids may be in the form of, for example, at least first, second and third fluid plugs, composed of first, second, and third fluids, respectively. The second fluid may be immiscible with the first and third fluids. In certain embodiments, the fluid plugs may be flowed in series in the incubation channel, e.g., in linear order. As the first fluid plug flows in the incubation channel, at least a portion of the first fluid may be removed from the first plug, thereby reducing the volume of the first fluid plug. For instance, portions of the first fluid (and/or components within the first fluid) may be deposited on the surface of the incubation channel during this flowing step. As the third fluid plug flows in the incubation channel, the third fluid may mix with portions of the deposited fluid to form a mixture of the first and third fluids in the third fluid plug. The mixing of fluids in a channel as described herein may allow for improved performance and simplification in the design and operations of fluidic devices that rely on mixing of fluids.

Another example of a method of mixing fluids in an incubation channel is shown in FIGS. 12A-12E. As shown illustratively in FIG. 12A, an incubation channel 270, including an upstream portion 272 and a downstream portion 274, may contain a first fluid plug 275 containing a first fluid 280, a second fluid plug 285 containing a second fluid 290, and a third fluid plug 295, containing a third fluid 300.

As shown illustratively in this figure, the second fluid plug may be positioned between and directly adjacent to the first and third fluid plugs, although in other embodiments additional fluid plugs may be positioned between the first and third fluid plugs. In some embodiments, the second fluid may be immiscible with the first and third fluids, while the first and third fluids may optionally be miscible with one another. For example, the second fluid may be a gas (e.g., air) and the first and third fluids may be liquids. Other fluid plugs may also be present in the channel as described in more detail below.

As used herein, when a fluid or fluid plug is referred to as being "adjacent" another fluid or fluid plug, it can be directly adjacent the fluid or fluid plug, or an intervening fluid or fluid plug also may be present. A fluid or fluid plug that is "directly adjacent" or "in contact with" another fluid or fluid plug means that no intervening fluid or fluid plug is present.

Figure 12A:
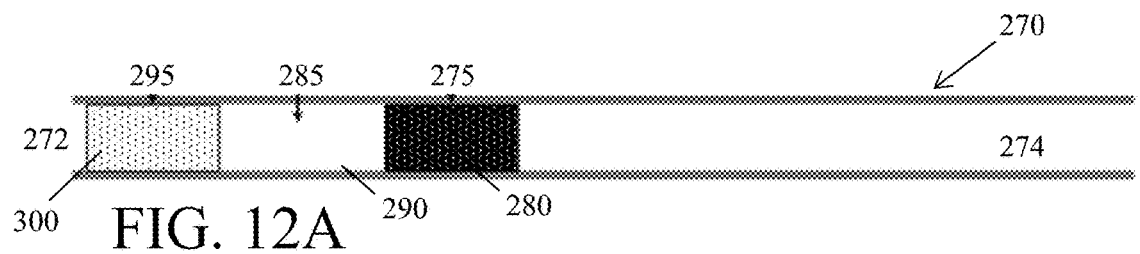
FIGS. 12A-12E show methods of mixing fluids in an incubation channel according to one set of embodiments.
Figure 12B:

As shown in FIG. 12B, the fluids may be flowed in series, e.g., from upstream to downstream in the direction of arrow 305. The incubation channel may be configured such that the flowing of the fluid plugs leads to the reduction of volume of the first fluid plug. For example, at least a portion of the first fluid (e.g., fluid portion 275) may deposit onto a surface of the incubation channel during fluid flow. Various channel configurations and methods for reducing the volume of the first fluid plug are described in more detail herein in U.S. Patent Publication No. 2014/0272935, filed Feb. 7, 2014, entitled "Mixing of Fluids in Fluidic Systems" [C1256.70011US01], which is incorporated by reference in its entirety. In certain embodiments in which the second fluid is immiscible with the first fluid, fluid portion 275 does not combine with the second fluid plug and as the second fluid plug flows in the channel. In embodiments in which the third fluid is miscible with the first fluid, the first and third fluids may combine to form a mixture 310 of at least portions of the two fluids, as shown illustratively in FIG. 12C.

Figure 12C:
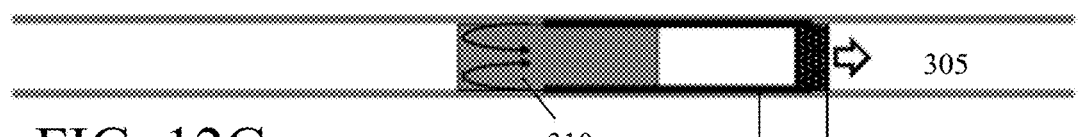

In some cases, as the first fluid plug flows, its volume may continue to reduce to a desired extent, for example, until mixture 310 includes a certain ratio of the first and third fluids, until a particular reduced volume of the first fluid plug has been reached, until a particular concentration of a component is present, or until a particular physical or chemical property is achieved. In some cases, the volume of the first fluid may be reduced by, for example, at least 50% as shown in FIG. 12C (or at least 25%, at least 75%, or at least 90%). In other cases, as shown illustratively in FIG. 12D, the entire volume of the first fluid plug may be reduced, such that only the second and third fluid plugs remain. The third fluid plug may then mix with the entire volume of the first fluid, as shown in FIG. 12E.

In some embodiments, the first and third fluids may contain a first and second component, respectively, for a chemical and/or biological reaction. In some cases, the first and second components are the same. In other embodiments, the first and second components are different. In some instances, a chemical and/or biological reaction involving the first and second components may be performed within the third fluid plug containing the mixture of the first and third fluids. For example, the first fluid may contain a silver salt and the third fluid may contain a reducing agent. The mixture of the first and third fluid may react with a reagent (e.g., gold colloids) to form detectable species (e.g., a silver film or particles that may be detected, for example, optically), as described in more detail below. Additional examples of chemical and/or biological reactions are described in more detail below. In certain embodiments, one or more fluid plugs contain a rinse solution, a diluent, a buffer, or a buffered reagent. Other types of fluids are also possible.

In some embodiment, mixing may occur between two or more assay components that are downstream (or upstream) of the sample. For instance, the incubation channel may contain a liquid plug and a reagent deposited on at least a portion of a surface of the incubation channel that were stored within the incubation channel prior to first use or prior to addition of the sample into the device. In some such embodiments, the deposited reagent may be downstream of the liquid plug. The liquid plug may dissolve, reconstitute, or suspend the deposited reagent and serve as a diluent for the deposited reagent. After the liquid plug has mixed with the deposited reagent, at least a portion of the liquid plug comprising the reagent, or the reagent itself, may be deposited on at least a portion of the surface of the incubation channel, as described above. The next liquid plug (e.g., the sample) may mix with the liquid containing the reagent that is deposited on the surface of the incubation channel.

As described herein, reagents (e.g., for a chemical and/or biological reaction) may be deposited in fluid and/or in dry form on one or more channel surfaces (e.g., incubation channel, detection channel, sample collector). In some embodiments, the reagent deposited on a surface of the sample collector or a surface of the fluidic device is present at the surface at a concentration of at least 50% (e.g., at least 60%, at least 70%, at least 80%, at least 90%, at least 95%) higher than a concentration of the reagent at another position within an interior of the sample collector or fluidic device. The deposited reagent may be associated with a fluidic device in any suitable manner. For example, reagents may be cross-linked, covalently bound, ionically bound, absorbed, adsorbed (physisorbed), or otherwise present on a surface within the fluidic device (e.g., in a channel of the device). In some embodiments, the reagent is a lyophilized reagent, a substantially dry reagent, a labelled reagent, a conditioning reagent, a pH modifier, a viscosity modifier, a blocking reagent, and/or a surfactant.

In certain embodiments, the reagent is a reagent for a chemical and/or biological reaction (e.g., a binding reaction), a dye or otherwise optically detectable substance, or small particles. Non-limiting examples of reagents that may be deposited on a channel surface include anti-coagulants (e.g., heparin, dipyridamole, EDTA, citrate), surfactants, buffers, conditioning reagents, pH modifiers, viscosity modifiers, release/displacement agents (e.g., comprising a carboxyl or amine oxide head group and a fluorinated or non-fluorinated carbon chain; detergents like perfluorohexanoic acid, FS50, FS51, and Empigen BB; steroids like 2-bromoestradiol and danazol), small molecules, proteins (e.g., albumin), antibodies (e.g., anti-vit-D antibodies and/or fragments thereof), transfer molecules (e.g., members of the beta-cyclodextrin family such as methyl-beta-cyclodextrin and/or acetyl-, succinyl-2-(hydroxypropyl)-, 2-hydroxypropyl-, carboxymethyl-, sulfate, 2-hydroxyethyl, succinyl-, and/or butyl groups), vitamin D (e.g., exogenous vitamin D) covalently coupled to a binding entity (e.g., bovine serum albumin), multivalent forms of small molecules (e.g., large molecule or protein labelled with more than one small molecules of interest, e.g., testosterone conjugate of bovine serum albumin with a 8:1 loading ratio), a labelled version of the molecule to be analyzed in the sample, such as exogenous, labelled/tagged vitamin D, labelled multivalent forms of small molecules and antibodies including non-labelled and labelled monoclonal and polyclonal antibodies. For example, in some embodiments the reagents are anti-vitamin D tracer monoclonal antibodies and/or fragments thereof labeled with metal (e.g., gold) or metal nanoparticles. Small molecules that can be measured by competitive immunoassays include: testosterone, hydroxytestosterone, cortisol, dehydroepiandrosterone (DHEA), digoxin, estradiol, estrone, folate, progesterone, T3 or triiodothyronine, T4 or thyroxin, vitamins (A, B1, B12, B2, B3, B6, D, 25-OH-D, and/or E). In some embodiments, the small molecule is vitamin D. In some embodiments, blocking reagents such as anti-species blocking agents (including HAMA blockers), bovine serum albumin (BSA), or any other scaffold molecule (a molecule or biochemical species that might be present in the solid phase to present a binding partner) can be included.

In some embodiments, a reagent is stored in the fluidic device prior to first use and/or prior to introduction of a sample into the device. Reagents may be disposed in or at one or more sides of an article of a device. For example, a reagent may be disposed in the incubation channel on a first side of the article, while another reagent is positioned in the detection channel positioned at a second side of the article. In other embodiments, one or more reagents are disposed in at least a portion of an intervening channel. In certain embodiments, one or more channels of a fluidic device include a stored liquid reagent. Certain fluidic devices may be designed to include both liquid and dry reagents stored in a single article prior to first use and/or prior to introduction of a sample into the device.

In certain embodiments, a reagent that is present (e.g., deposited) on a surface of a channel is deposited during use of the device. In some embodiments, prior to first use of the device and/or prior to introduction of a sample into the device, the reagent is not present on a surface of the device. During use, a fluid containing the reagent is flowed, and the act of flowing the fluid (e.g., fluid plug) may cause the reagent to be deposited onto the surface as described herein.

In some embodiments in which a reagent is deposited prior to use, prior to introduction of the sample, or during use, a method may comprise depositing at least a portion of the sample on a surface of the sample collector and/or fluidic device, and mixing the deposited sample with a diluting reagent to form a mixed fluid, such that a concentration of a component of the sample in the mixed fluid is less than or equal to about 97%, less than or equal to about 95%, less than or equal to about 90%, less than or equal to about 80%, less than or equal to about 70%, less than or equal to about 60%, less than or equal to about 50%, less than or equal to about 40%, less than or equal to about 30%, less than or equal to about 20%, less than or equal to about 10%; and/or at least about 0.1%, 1%, or 3%, of a concentration of the component of the sample prior to the depositing step. Combinations of the above-referenced ranges are also possible.

In some embodiments, the amount of mixing and/or the number of fluids plugs that are mixed together may be controlled by certain characteristics of the incubation channel. For instance, the geometry of the channel may be used to control mixing. Non-limiting examples of geometrical channel features that may influence mixing include cross-sectional shape, cross-sectional area, aspect ratio, hydraulic diameter, radius of curvature of internal corners, deviations in the channel (e.g., turns, bends), radius of curvature of deviations in the channel, and gradual and/or abrupt changes in channel geometry (e.g., changes in cross-section area). For instance, a channel cross-section with sharper corners may more readily facilitate removal of a fluid from a fluid plug (e.g., to cause the fluid or a reagent to be deposited on a channel surface) compared to a channel cross-section with blunt corners. In one example, a channel with a cross-section that includes a radius of curvature substantially smaller than the half-width and/or half-height of the channel may more readily facilitate removal of a fluid from a fluid plug compared to a channel cross-section that does not include such a radius of curvature, or a channel cross-section having a relatively larger radius of curvature. A radius of curvature substantially smaller than the half-width and/or half-height of the channel may be, for example, less than or equal to about 50%, less than or equal to about 40%, less than or equal to about 30%, less than or equal to about 20%, less than or equal to about 10%, or less than or equal to about 5% of the half-width and/or half-height of the channel. Additional examples of channel configurations and dimensions are provided in more detail below.

The length of the channel may also be used to control incubation and/or mixing. For example, longer channels may allow greater volume reduction of a fluid plug compared to a shorter channel, with all other factors being equal. In some cases, a channel that is substantially longer than the length occupied by the fluid plug may allow greater volume reduction of the fluid (e.g., the entire volume) than a channel that is not substantially longer than the length occupied by the fluid plug. In some instances, mixing and/or incubation may be controlled using more than one characteristic (e.g., cross-section shape and length). Other methods of controlling mixing based on characteristics of the channel are also possible.

In some embodiments, the amount of mixing and/or the number of fluids plugs that are mixed together may be controlled by certain characteristics of a channel surface (e.g., surface roughness, surface texture, surface energy, surface polarity, surface charge, interfacial surface tension between the channel surface and a fluid, local variations in the characteristics of the channel surface). For instance, the surface roughness of a channel surface may be selected to facilitate or prevent removal of a fluid portion from a fluid plug. A channel surface with a higher surface roughness may more readily facilitate removal of a fluid portion from a fluid plug than a channel surface with a lower surface roughness.

In some instances, a fluidic device comprises a combination of two or more separate components (e.g., articles, layers, or fluidic devices) mounted together. Independent channel networks, which may optionally include reagents stored and/or sealed therein prior to first use, may be included on or in the different components of the fluidic device. The separate components may be mounted together or otherwise associated with one another by any suitable means, such as by the methods described herein, e.g., to form a single (composite) fluidic device. In some embodiments, two or more channel networks are positioned in different components, articles or layers of the fluidic device and are not connected fluidically prior to first use, but are connected fluidically at first use, e.g., by use of a sample connector. In some embodiments, two or more channel networks are positioned in different components, articles or layers of the fluidic device and are not connected fluidically prior to connection of a fluidic connector (and/or sample connector) to the components, articles or layers including the fluidic network(s) of channels, but upon connection causes fluid communication between at least two channels on different components, articles or layers of the device.

Advantageously, each of the different components or layers that form a composite fluidic device may be tailored individually depending on the designed function(s) of that component or layer. For example, in one set of embodiments, one component of a composite fluidic device may be tailored for storing wet reagents. Additionally or alternatively, e.g., depending on the amount of fluids to be stored, the storage region(s) of that fluidic device may be made with larger (or smaller) cross-sectional dimensions than channels or regions of other components not used for storage of liquids. The material used to form the fluidic device may be compatible with fabrication techniques suitable for forming larger (or smaller) cross-sectional dimensions. By contrast, a second component that may be tailored for detection of an analyte, or a second component that may be tailored to include an incubation channel for incubation or mixing may, in some embodiments, include channel portions having relatively smaller (or larger) cross-sectional dimensions. Additionally or alternatively, a channel portion of the second component may have a lower (or higher) surface roughness compared to a channel portion of another component (e.g., a first component including a channel used for storage of a reagent). The cross sectional dimensions or surface roughness of the channel portions of the second component may, in certain embodiments, require a certain fabrication technique or fabrication tool different from that used to form a different component of the fluidic device. Furthermore, in some particular embodiments, the material used for the second component may be well characterized for protein attachment and detection. As such, it may be advantageous to form different channels used for different purposes on different components of a fluidic device, which can then be joined together prior to use by an intended user.

In some embodiments, a channel includes a feature on or in an article or substrate that at least partially directs the flow of a fluid. For instance, a feature that is formed in a surface or a side of an article or substantially embedded within the article may constitute a channel if it at least partially directs the fluid flow. An intervening channel refers to a channel that connects two channels lying on two different planes. In some embodiments, one or more channels are microfluidic.

Microfluidic may refer to a device, apparatus or system including at least one fluid channel having a cross-sectional dimension of less than 1 mm, and a ratio of length to largest cross-sectional dimension of at least 3:1. A microfluidic channel or microfluidic channel may refer to a channel meeting these criteria. Though in some embodiments, devices described herein may be microfluidic, in certain embodiments, the systems and devices are not limited to microfluidic systems and may relate to other types of fluidic systems. Furthermore, it should be understood that all or a majority of the channels described herein may be microfluidic in certain embodiments. Non-microfluidic channels may also be used.

A cross-sectional dimension (e.g., a diameter, a height, and/or a width) of a channel described herein is measured perpendicular to the direction of fluid flow. Examples of cross-sectional dimensions are provided below.

It should be understood that a channel can have any suitable cross-sectional dimension, which may depend on, for example, where the channel is positioned in the device, how the channel is to be used (e.g., for mixing or for storage of reagents), the size of the fluidic device, the volume of reagents intended to flow in the device, etc. For instance, in some embodiments, a channel (e.g., an incubation channel, a detection channel, a channel used for storing a reagent, an intervening channel, a bridging channel, a channel of the sample collector) may have a maximum cross-sectional dimension (e.g., a width or height) of less than or equal to about 5 mm, less than or equal to about 3 mm, less than or equal to about 1 mm, less than or equal to about 750 microns, less than or equal to about 600 microns, less than or equal to about 500 microns, less than or equal to about 300 microns, less than or equal to about 200 microns, less than or equal to about 100 microns, less than or equal to about 50 microns, less than or equal to about 25 microns, less than or equal to about 10 microns, or less than or equal to about 5 microns. In some instances, a channel, channel, or channel portion, may have a maximum cross-sectional dimension of greater than or equal to about 0.1 microns, greater than or equal to about 1 microns, greater than or equal to about 5 microns, greater than or equal to about 10 microns, greater than or equal to about 25 microns, greater than or equal to about 50 microns, greater than or equal to about 100 microns, greater than or equal to about 200 microns, greater than or equal to about 400 microns, greater than or equal to about 600 microns, greater than or equal to about 900 microns, greater than or equal to about 1 mm, greater than or equal to about 1.5 mm, or greater than or equal to about 3 mm. Combinations of the above-referenced ranges are also possible (e.g., greater than or equal to about 1 micron and less than or equal to about 1 mm). Other values of maximum cross-sectional dimensions are also possible.

In some cases, at least one or at least two cross-sectional dimensions (e.g., a height and a width) of a channel (e.g., an incubation channel, a detection channel, a channel used for storing a reagent, an intervening channel, a bridging channel, a channel of the sample collector) may be less than or equal to about 2 mm, less than or equal to about 1 mm, less than or equal to about 750 microns, less than or equal to about 500 microns, less than or equal to about 300 microns, less than or equal to about 200 microns, less than or equal to about 100 microns, less than or equal to about 50 microns, less than or equal to about 25 microns, less than or equal to about 10 microns, or less than or equal to about 5 microns. In some instances, at least one or at least two cross-sectional dimensions of a channel may be greater than or equal to about 0.1 microns, greater than or equal to about 1 micron, greater than or equal to about 5 microns, greater than or equal to about 10 microns, greater than or equal to about 25 microns, greater than or equal to about 50 microns, greater than or equal to about 100 microns, greater than or equal to about 200 microns, greater than or equal to about 400 microns, greater than or equal to about 600 microns, or greater than or equal to about 700 microns. Combinations of the above-referenced ranges are also possible (e.g., greater than or equal to about 10 µm and less than or equal to about 500 µm). Other values are also possible.

A channel (e.g., an incubation channel, a detection channel, a channel used for storing a reagent, an intervening channel, a bridging channel, a channel of the sample collector) may have a certain width-to-height ratio. In certain instances, the ratio of the width to height of a channel may be greater than or equal to about 1:1, greater than or equal to about 2:1, greater than or equal to about 5:1, greater than or equal to about 10:1, greater than or equal to about 15:1, or greater than or equal to about 20:1. In some instances the width-to-height ratio may be less than or equal to about 30:1, less than or equal to about 20:1, less than or equal to about 15:1, less than or equal to about 10:1, less than or equal to about 5:1, or less than or equal to about 2:1. Combinations of the above-referenced ranges are also possible (e.g., greater than or equal to about 1:1 and less than or equal to about 20:1). Other values are also possible.

A channel (e.g., an incubation channel, a detection channel, a channel used for storing a reagent, an intervening channel, a bridging channel, a channel of the sample collector) may also have an aspect ratio (length to largest average cross-sectional dimension) of at least 2:1, more typically at least 3:1, 5:1, or 10:1. In some cases, a channel has a very large aspect ratios e.g., at least 100:1, 500:1 or 1000:1. In certain embodiments, a channel, has a length to largest width of less than or equal to 10, 7, 5, 3, or 2.

A channel may have a length and/or volume for mixing, incubation, and/or storage as described herein. In some embodiments a channel (e.g., an incubation channel, a detection channel, a channel used for storing a reagent, an intervening channel, a bridging channel, a channel of the sample collector) may have a volume of greater than or equal to about 0.001 picoliters, greater than or equal to about 0.01 picoliters, greater than or equal to about 0.1 picoliters, greater than or equal to about 1 picoliters, greater than or equal to about 10 picoliters, greater than or equal to about 100 picoliters, greater than or equal to about 0.001 microliters, greater than or equal to about 0.01 microliters, greater than or equal to about 0.1 microliters, greater than or equal to about 1 microliter, greater than or equal to about 10 microliters, greater than or equal to about 25 microliters, greater than or equal to about 50 microliters, greater than or equal to about 100 microliters, greater than or equal to about 150, or greater than or equal to about 200 microliters. In some instances, a channel, may have a volume of less than or equal to about 250 microliters, less than or equal to about 200 microliters, less than or equal to about 150 microliters, less than or equal to about 100 microliters, less than or equal to about 50 microliters, less than or equal to about 25 microliters, less than or equal to about 15 microliters, less than or equal to about 10 microliters, less than or equal to about 5 microliters, less than or equal to about 1 microliters, less than or equal to about 0.1 microliters, or less than or equal to about 0.01 microliters, less than or equal to about 0.001 microliter, less than or equal to about 100 picoliters, less than or equal to about 10 picoliters, less than or equal to about 1 picoliter, or less than or equal to about 0.1 picoliter, less than or equal to about 0.01 picoliter. Combinations of the above-referenced ranges are also possible (e.g., greater than or equal to about 0.001 picoliters and less than or equal to about 200 microliters). Other volumes are also possible.

In some embodiments, a channel (e.g., an incubation channel, a detection channel, a channel used for storing a reagent, an intervening channel, a bridging channel, a channel of the sample collector) may have a length of greater than or equal to about 1 mm, greater than or equal to about 5 mm, greater than or equal to about 10 mm, greater than or equal to about 20 mm, greater than or equal to about 40 mm, greater than or equal to about 60 mm, or greater than or equal to about 80 mm. In some instances, the length may be less than or equal to about 100 mm, less than or equal to about 90 mm, less than or equal to about 70 mm, less than or equal to about 50 mm, less than or equal to about 30 mm, or less than or equal to about 10 mm. Combinations of the above-referenced ranges are also possible (e.g., greater than or equal to about 1 mm and less than or equal to about 100 mm). Other values of length are also possible.

Some fluidic devices and articles are designed such that a cross-sectional dimension of an intervening channel, such as one that passes from a first surface to a second surface of an article, is within a certain range of a cross-sectional dimension of a non-intervening channel (e.g., an incubation channel, a detection channel, a bridging channel, a channel of the sample collector). In one particular embodiment, an intervening channel may have one or more cross-sectional dimensions (e.g., a smallest, largest, or average width or height) within a certain percentage of a cross-sectional dimension (e.g., a smallest, largest, or average width or height) of a channel directly connected to the intervening channel but which does not pass through the article from a first surface to a second surface.

In other cases, an intervening channel, such as one that passes from a first surface to a second surface of an article, has one or more cross-sectional dimensions within 40%, 30%, 20%, or 10% of the smallest width of a channel directly connected to the intervening channel (e.g., an incubation channel, a detection channel, a bridging channel, a channel of the sample collector). The channel that is directly connected to the intervening channel may optionally be formed in a surface of the article. Having an intervening channel with dimensions that are proportional to the dimensions of the channels in which the intervening channel is directly connected can reduce the number and volume of reagents and/or air bubbles that are trapped in the intervening channel during use of the device.

In some cases, an intervening channel has a volume less than or equal to one or more volumes of fluid reagents stored in the fluidic device prior to first use of the device. For instance, an intervening channel may have a volume that is less than or equal to 5, 3, 2, 1, 0.75, 0.5, or 0.25 times the volume of the largest volume of fluid reagent stored in a device prior to first use. In some instances, such configurations may facilitate transfer of fluids between channels so as to reduce or prevent fluids from being trapped in certain portions of the channels (e.g., at the connection between two channels).

In some cases, a channel (e.g., an intervening channel) that passes through the device from a first surface to a second surface of the article (e.g., through the thickness of the device) has a length the same as or substantially similar to the thickness of the article. The thickness of the article may depend on a variety of factors such as the material in which the article is formed, the fabrication technique, and the use of the channel (e.g., for storage of reagents or for detection). The article may have a thickness of, for example, less than or equal to 3 mm, 10 mm, 8 mm, 5 mm, 3 mm, 2 mm, 1 mm or 0.5 mm, and/or at least 0.5 mm, 1 mm, 2 mm, 3 mm, 5 mm, 8, mm, or 10 mm. Accordingly, a channel that passes through the thickness of the device may have a same such length.

In some embodiments, a channel (e.g., an incubation channel, a detection channel, a channel used for storing a reagent, an intervening channel, a bridging channel, a channel of the sample collector) may include one or more corners (e.g., curved corners) having a certain radius of curvature. The curved corner may be, for example, a convex portion of a surface that mates with a cover. The convex portion of the surface may be formed during fabrication of the channel by various techniques (e.g., injection molding). In certain embodiments, a channel may include one or more corners (e.g., curved corners) having a radius of curvature of, for example, less than or equal to about 100 µm, less than or equal to about 50 µm, less than or equal to about 30 µm, less than or equal to about 20 µm, less than or equal to about 10 µm, less than or equal to about 5 µm, less than or equal to about 3 µm, less than or equal to about 2 µm, less than or equal to about 1 µm, less than or equal to about 0.5 µm, or less than or equal to about 0.1 µm. In some embodiments, the radius of curvature of a curved corner of a channel may be, e.g., greater than or equal to about 0.1 µm, greater than or equal to about 0.5 µm, greater than or equal to about 1 µm, greater than or equal to about 2 µm, greater than or equal to about 3 µm, greater than or equal to about 5 µm, greater than or equal to about 10 µm, greater than or equal to about 20 µm, greater than or equal to about 30 µm, greater than or equal to about 50 µm, or greater than or equal to about 100 µm. Combinations of the above-noted ranges are also possible (e.g., a radius of curvature of greater than or equal to about 1 micron and less than or equal to about 20 microns). Other ranges are also possible. In some embodiments in which it is desirable to deposit a fluid or a reagent from a fluid plug onto a surface of a channel, a curved corner having a relatively smaller radius of curvature may increase the amount of fluid being deposited from the fluid plug flowing along a portion of the channel, compared to a fluid plug flowing in a channel having a relatively larger radius of curvature.

A channel (e.g., an incubation channel, a detection channel, a channel used for storing a reagent, an intervening channel, a bridging channel, a channel of the sample collector) having a substantially curved corner (e.g., a convex portion of a surface that mates with a cover) may have a ratio of a cross-sectional dimension (e.g., a width or a height) of the channel to the radius of curvature of the substantially curved corner (or convex portion) of at least 1:1, 2:1, 3:1, 5:1, 10:1, 20:1, 30:1, 50:1, 100:1, 200:1, or 500:1. In some embodiments, the ratio is less than or equal to 500:1, 200:1, 100:1, 50:1, 30:1, 20:1, 10:1, 5:1, 3:1, 2:1 or 1:1. Combinations of the above-referenced ranges are also possible. Other values are also possible.

It should be understood, that a channel (e.g., an incubation channel, a detection channel, a channel used for storing a reagent, an intervening channel, a bridging channel, a channel of the sample collector) may have any suitable cross-sectional shape and may be, for example, substantially-circular, oval, triangular, irregular, square, rectangular, trapezoidal, semi-circular, semi-ovular or the like.

A channel (e.g., an incubation channel, a detection channel, a channel used for storing a reagent, an intervening channel, a bridging channel, a channel of the sample collector) may have any suitable configuration. In some embodiments, a channel, may be a common channel, a branching channel, a channel on a side of a device that is separated from another channel by an intervening channel (e.g., a channel passing through the thickness of the device, as part of a two-sided device), or any other suitable configuration. In some cases, channels or channel portions may be separated from one another by a component (e.g., a vent valve or port), or may differ from one another based on a feature of the channel or portion (e.g., surface roughness, dimension, etc.). Other configurations are also possible.

A channel (e.g., an incubation channel, a detection channel, a channel used for storing a reagent, an intervening channel, a bridging channel, a channel of the sample collector) can be covered or uncovered. In embodiments where it is covered, at least one portion of the channel can have a cross-section that is substantially enclosed, or the entire channel may be substantially enclosed along its entire length with the exception of its inlet(s) and outlet(s). One or more inlet(s) and/or outlet(s) may also be enclosed and/or sealed. In certain embodiments, one or more covers is adapted and arranged such that a channel, an inlet, and/or an outlet is substantially enclosed and/or sealed prior to first use of the device by a user, but opened or unsealed at first use. In some embodiments, such a configuration may substantially prevent fluids and/or other reagents stored in the device from being removed from the device (e.g., due to evaporation) during fabrication, shipping, and/or storage of the device, as described herein.

Fluids can be flowed in a device described herein using any suitable method. In some embodiments, a fluidic device employs one or more valves (e.g., vent valves) to controllably flow and/or mix portions of fluid within the system. A vent valve can comprise, for example, a port in fluid communication with the channel in which a fluid is positioned, and may be actuated by positioning a seal over the port opening or by removing the seal from the port opening. In certain embodiments, the seal may include a valving mechanism such as a mechanical valve operatively associated with a tube in fluid communication with the port. Generally, opening the vent valve allows the port to function as a vent. When the port functions as a vent, the fluid located on one side of the vent valve flows, while the fluid located on the opposite side of the vent valve relative to the first fluid remains stationary. When the valve is closed, the port no longer functions as a vent, and the fluid located on both sides of the vent valve can flow through the system towards an outlet. Advantageously, fluid control such as a sequence of fluid flow and/or a change in flow rate can be achieved by opening and closing one or more vent valves and by applying a single source of fluid flow (e.g., a vacuum) operated at a substantially constant pressure. This can simplify the operation and use of the device by an intended user. Vent valves are described in more detail in U.S. Patent Publication No. 2011/0120562, filed Nov. 24, 2010 and entitled "Fluid Mixing and Delivery in Microfluidic Systems," which is incorporated herein by reference in its entirety for all purposes.

In some embodiments, when the fluid flow source is activated, one or more channels in the fluidic device may be pressurized (e.g., in the range of −10 kPa to −60 kPa, such as approximately −30 kPa) which may drive the fluids within the channel toward the outlet. In some embodiments, fluids can be stored serially in a channel upstream of a vent valve positioned along the channel, and after closing the vent valve, the fluids can flow sequentially towards the channel outlet. In some cases, fluids can be stored in separate, intersecting channels, and after closing a vent valve the fluids can be flowed sequentially. The timing of delivery and the volume of fluid can be controlled, for example, by the timing of the vent valve actuation.

Advantageously, vent valves can be operated without constricting the cross-section of the microfluidic channel on which they operate, as might occur with certain valves in the prior art. Such a mode of operation can be effective in preventing leaking across the valve. Moreover, because vent valves can be used, some systems and methods described herein do not require the use of certain internal valves, which can be problematic due to, for example, their high expense, complexity in fabrication, fragility, limited compatibility with mixed gas and liquid systems, and/or unreliability in microfluidic systems.

It should be understood that while vent valves are described, other types of valving mechanisms can be used with the systems and methods described herein. Non-limiting examples of a valving mechanism which may be operatively associated with a valve include a diaphragm valve, ball valve, gate valve, butterfly valve, globe valve, needle valve, pinch valve, poppet valve, or pinch valve. The valving mechanism may be actuated by any suitable means, including a solenoid, a motor, by hand, by electronic actuation, or by hydraulic/pneumatic pressure.

In certain embodiments, one or more channels of a fluidic device include a stored liquid reagent (e.g., in the form of a fluid plug). In some cases, more than one liquid reagents (e.g., fluid plugs) are stored in a channel. The liquid reagents may be separated by a separation fluid, which may be immiscible with the liquid reagents. The fluid reagents may be stored in the device prior to first use, prior to introduction of a sample, or prior to forming a fluidic connection between two previously unconnected channels (e.g., using a fluidic connector). In other embodiments, a fluid reagent may be introduced into the device at first use. In some cases, the liquid reagents may be kept separate during storage of the fluids (e.g., while the device is sealed). During use of the device, at least portions of the liquids may be combined (e.g., mixed) using the methods described herein.

Certain fluidic devices may be designed to include both liquid and dry reagents stored in a single article prior to first use and/or prior to introduction of a sample into the device. In some cases, the liquid and dry reagents are stored in fluid communication with each other prior to first use. In other cases, the liquid and dry reagents are not in fluid communication with one another prior to first use, but at first use are placed in fluid communication with one another. For instance, one or more liquid reagents may be stored in a first common channel and one or more dry reagents stored in a second common channel, the first and second common channels not being connected or in fluidic communication with one another prior to first use, prior to introduction of a sample, or prior to forming a fluidic connection between the two common channels (e.g., using a fluidic connector). Additionally or alternatively, the reagents may be stored in separate vessels such that a reagent is not in fluid communication with the fluidic device prior to first use. The use of stored reagents can simplify use of the fluidic device by a user, since this minimizes the number of steps the user has to perform in order to operate the device. This simplicity can allow the fluidic devices described herein to be used by untrained users, such as those in point-of-care settings, and in particular, for devices designed to perform immunoassays.

In various embodiments involving the storage of fluid (e.g., liquid) reagents prior to first use, the fluids may be stored (and, in some embodiments, statically maintained without mixing) in a fluidic device for greater than 10 seconds, one minute, one hour, one day, one week, one month, or one year. By preventing contact between certain fluids, fluids containing components that would typically react or bind with each other can be prevented from doing so, e.g., while being maintained in a common channel. For example, while they are stored, fluids (e.g., in the form of fluid plugs) may be kept separated at least in part by immiscible separation fluids so that fluids that would normally react with each other when in contact may be stored for extended periods of time in a common channel. In some embodiments, the fluids may be stored so that they are substantially statically maintained and do not move in relation to their position in the channel. Even though fluids may shift slightly or vibrate and expand and contract while being statically maintained, certain fluidic devices described herein are adapted and arranged such that fluids in a common channel do not mix with one another during these processes.

Fluidic devices that are used for storage of one or more reagents (e.g., prior to first use) may be stored at reduced temperatures, such as less than or equal to 10° C., 4° C., 0° C., or −10° C. Fluids may also be exposed to elevated temperatures such as greater than 25° C., greater than 35° C. or greater than 50° C. Fluids may be shipped from one location to the other by surface or air without allowing for mixing of reagent fluids contained in the channel. The amount of separation fluid may be chosen based on the end process with which the fluids are to be used as well as on the conditions to which it is expected that the fluidic device will be exposed. For example, if the fluidic device is expected to receive physical shock or vibration, and/or is expected to be exposed to a depressurized environment, fluids may only fill portions but not all of a channel. Furthermore, larger plugs of immiscible separation fluid may be used along with one or more channel configurations described herein. In this manner, distinct fluids within a channel system of a fluidic device may avoid mixing.

A fluidic device may include one or more characteristics that facilitate control over fluid transport and/or prevent fluids from mixing with one another during storage. For example, a device may include structural characteristics (e.g., an elongated indentation or protrusion) and/or physical or chemical characteristics (e.g., hydrophobicity vs. hydrophilicity) or other characteristics that can exert a force (e.g., a containing force) on a fluid. In some cases, a fluid may be held within a channel using surface tension (e.g., a concave or convex meniscus). For example, certain portions of a channel may be patterned with hydrophobic and hydrophilic portions to prevent movement and/or mixing of fluids during storage. In some cases, a common channel may have an absence of inner surfaces or other dividers to keep the fluids apart and fluids may be separated by a separation fluid.

In certain embodiments, the surface tension between a fluid and a channel surface may be selected as desired. In some cases, a wetting agent may be added to a fluid or fluid plug to control the surface tension. The wetting agent may be added, for example, prior to mixing, as a result of mixing, or as a result of a fluid being removed from a fluid plug. In certain cases, a wetting agent may be added to the channel surface to control surface tension, e.g., during manufacturing of the device, prior to fluid flow, and/or as a result of fluid flow. In general, any suitable wetting agent at any desired concentration may be used. Examples of suitable wetting agents include, but are not limited to, polyvinyl alcohol, non-ionic detergents (e.g., poly(ethylene oxide) derivatives like Tween 20 and Triton, fatty alcohols), anionic detergents (e.g., sodium dodecyl sulfate and related detergents with shorter or longer alkane chains such as sodium decyl sulfate, sodium dodecyl sulfate, or sodium octadecyl sulfate, or fatty acid salts), cationic detergents (e.g., quaternary ammonium cations such as cetyl trimethylammonium bromide), zwitterionic detergents (e.g., dodecyl betaine), detergents including carboxyl head groups and fluorinated or non-fluorinated carbon chain(s), detergents including amine oxide head groups and fluorinated or non-fluorinated carbon chain(s), perfluorodetergents (e.g., Capstone FS-10, perfluoroheptanoic acid, or perfluorooctanoic acid), low surface tension liquids (e.g., alcohols such as isopropanol or 1-butanol), and combinations thereof. In certain embodiments, a non-wetting agent (e.g., ionic compounds) may be added to increase the surface tension.

In embodiments in which a wetting agent is added to a fluid or fluid plug, the percentage (by weight/volume) of the wetting agent in the fluid or fluid plug may be greater than or equal to about 0.001%, greater than or equal to about 0.01%, greater than or equal to about 0.025%, greater than or equal to about 0.05%, greater than or equal to about 0.1%, greater than or equal to about 0.1%, greater than or equal to about 0.5%, greater than or equal to about 1%, greater than or equal to about 5%, greater than or equal to about 10%, greater than or equal to about 20%, greater than or equal to about 30%, greater than or equal to about 40%, or greater than or equal to about 40%. In some instances, the percentage of wetting agent in the fluid or fluid plug may be less than or equal to about 75%, less than or equal to about 50%, less than or equal to about 40%, less than or equal to about 30%, less than or equal to about 20%, less than or equal to about 10%, less than or equal to about 5%, less than or equal to about 1%, less than or equal to about 0.5%, less than or equal to about 0.01%, or less than or equal to about 0.01%. Combinations of the above-referenced ranges are also possible (e.g., greater than or equal to about 0.01% or less than or equal to about 50%). Other ranges of wetting agent percentages are also possible.

Figure 12D:
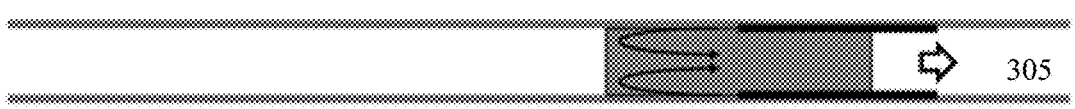
Figure 12E:
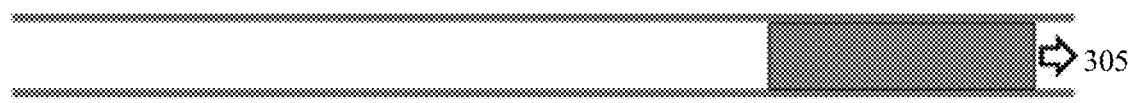

In certain cases, as shown in illustratively FIG. 12D the entire volume of a fluid (e.g., a first fluid, a second fluid) may be incorporated into one or more fluid plugs downstream such that the fluid plug is no longer present in the channel. In some cases, the volume of the fluid in the fluid plug may be reduced by a certain percentage (e.g., compared to the initial volume of the fluid plug). For instance, in some embodiments, the volume of a fluid plug may be reduced by greater than or equal to about 50%, greater than or equal to about 60%, greater than or equal to about 70%, greater than or equal to about 80%, greater than or equal to about 90%, or greater than or equal to about 95%. In some instances, the volume of a fluid in a fluid plug may be reduced by less than or equal to about 100%, less than or equal to about 90%, less than or equal to about 80%, less than or equal to about 70%, or less than or equal to about 60%. Combinations of the above-referenced ranges are also possible (e.g., greater than or equal to about 50% and less than or equal to about 100%). In some cases, 100% of the volume of the fluid is removed from a fluid plug, such that the fluid plug no longer remains in the system. In such embodiments, the fluid removed from the fluid plug may be entirely deposited or dispersed along or within the channel. In other embodiments, 0% of the fluid is removed from a fluid plug during fluid flow. Other values of volume reduction percentage are also possible. As described herein, in some embodiments the volume of more than one fluid plugs is reduced by the amounts noted above.

Detection of a sample in a fluidic device may have a variety of forms. In some cases, detection occurs continuously. In other embodiments, detection occurs periodically; and yet other embodiments, detection occurs sporadically. In some cases, detection occurs upon a specific event or condition taking place.

As described herein, detection can take place at any suitable position with respect to a fluidic device. In some cases, one or more detectors are stationery with respect to a fluidic device during use and/or during detection. For example, a stationery detector may be positioned adjacent a certain region of the fluidic device, such as a detection zone/detection channel, where one or more events (e.g., a chemical or biological reaction, introduction of a fluid into the zone/channel) may take place. The detector may detect, for example, the passing of fluids across the detection zone and/or analysis region. Additionally or alternatively, the detector may detect the binding or association of other components at that region (e.g., the binding of a component to surface of the analysis region). In some embodiments, stationery detector(s) may monitor multiple analysis regions within a detection zone simultaneously. For example, a detector such as a camera may be used to image an entire fluidic device, or large portion of the device, and only certain areas of the device scrutinized. Components such as optical fibers may be used to transmit light from multiple analysis regions to a single detector. In other embodiments, multiple detectors may each be aligned with an analysis region in a detection zone, as described in more detail in U.S. Pat. No. 8,501,416, issued Aug. 6, 2013 and entitled "Fluidic Structures Including Meandering and Wide Channels" [H0498.70244US01], which is incorporated herein by reference in its entirety.

A fluidic device, or portions thereof (e.g., a substrate, an article, a layer, a component), can be fabricated of any material suitable for forming a channel or other component. Non-limiting examples of materials include polymers (e.g., polypropylene, polyethylene, polystyrene, poly(styrene-co-acrylonitrile), poly(styrene-co-butadiene), poly(acrylonitrile, butadiene, styrene), poly(styrene-co-maleic anhydride), poly(styrene-co-acrylate), poly(styrene-co-methyl methacrylate), poly(methyl methacrylate), polycarbonate, poly(dimethylsiloxane), PVC, PTFE, PET, cyclo-olefin copolymer, or blends of two or more such polymers, or metals including nickel, copper, stainless steel, bulk metallic glass, or other metals or alloys, or ceramics including glass, quartz, silica, alumina, zirconia, tungsten carbide, silicon carbide, or non-metallic materials such as graphite, silicon, or others.

In certain embodiments in which a copolymer is used to form a component of a device described herein (e.g., a substrate, an article, a layer), the copolymer may include a first polymer component that is substantially non-reactive (e.g., a styrene-containing group, an acrylonitrile group, a butadiene group) and a second polymer component. In some embodiments, the second polymer component may be reactive (e.g., include reactive functional groups) for further functionalization (e.g., with a biomolecule (e.g. protein) or other entity that may be involved in, or associated with, an analysis to be performed). In other embodiments, the second polymer component may be non-reactive (e.g., does not include reactive functional groups). Non-limiting examples of second polymer components (e.g., that may be reactive) include anhydride-containing groups, such as maleic anhydride, ethyl maleic anhydride; maleimide-containing groups; amine-containing groups; aldehyde-containing groups; and acrylate-containing groups. Additional non-limiting examples of second polymer components (e.g., that are non-reactive) include acrylonitrile groups, butadiene groups, and methyl methacrylate groups. Such materials may be used to form a component of a device including, for example, an incubation channel, a detection channel, a channel used for storing a reagent, an intervening channel, a bridging channel, and/or a channel of the sample collector.

In embodiments in which a copolymer, such as one noted above, is used to form a component of a device described herein (e.g., a substrate, an article, a layer), the wt % of a first polymer component (e.g., styrene) in the copolymer may be, for example, at least 50 wt %, at least 50 wt %, at least 60 wt %, at least 70 wt %, at least 80 wt %, at least 85 wt %, at least 87 wt %, at least 90 wt %, at least 92 wt %, at least 94 wt %, at least 96 wt %, or at least 98 wt %. The wt % of a first polymer component in the copolymer may be, in some embodiments, less than 100 wt %, less than or equal to 99 wt %, less than or equal to 95 wt %, less than or equal to 90 wt %, less than or equal to 80 wt %, less than or equal to 70 wt %, less than or equal to 60 wt %, or less than or equal to 50 wt %. Combinations of the above-referenced ranges are possible (e.g., at least 90 wt % and less than or equal to 99 wt %). Other ranges are also possible.

In embodiments in which a copolymer, such as one noted above, is used to form a component of a device described herein (e.g., a substrate, an article, a layer), the wt % of a second polymer component in the copolymer may be, for example, at least 2 wt %, at least 5 wt %, at least 8 wt %, at least 10 wt %, at least 12 wt %, at least 15 wt %, at least 20 wt %, at least 25 wt %, at least 28 wt %, at least 30 wt %, at least 35 wt %, at least 40 wt %, at least 45 wt %, at least 50 wt %, at least 55 wt %, at least 60 wt %, at least 65 wt %, at least 70 wt %, at least 75 wt %, or at least 80 wt % (with respect to the total weight of the copolymer). The wt % of a second polymer component in the copolymer may be, in some embodiments, less than or equal to 90 wt %, less than or equal to 80 wt %, less than or equal to 70 wt %, less than or equal to 60 wt %, less than or equal to 50 wt %, less than or equal to 40 wt %, less than or equal to 30 wt %, less than or equal to 25 wt %, less than or equal to 20 wt %, less than or equal to 15 wt %, less than or equal to 10 wt %, less than or equal to 8 wt %, or less than or equal to 5 wt % (with respect to the total weight of the copolymer). Combinations of the above-referenced ranges are possible (e.g., at least 2 wt % and less than or equal to 30 wt %). Other ranges are also possible.

In certain embodiments in which a blend of two polymers or copolymers is used to form a component of a device described herein (e.g., a substrate, an article, a layer), the proportion of the first polymer or copolymer in the blend may be, for example, at least 50 wt %, at least 50 wt %, at least 60 wt %, at least 70 wt %, at least 80 wt %, at least 90 wt %, at least 92 wt %, at least 94 wt %, at least 96 wt %, or at least 98 wt %. The wt % of a first polymer component in the copolymer may be, in some embodiments, less than 100 wt %, less than or equal to 99 wt %, less than or equal to 95 wt %, less than or equal to 90 wt %, less than or equal to 80 wt %, less than or equal to 70 wt %, less than or equal to 60 wt %, or less than or equal to 50 wt %. Combinations of the above-referenced ranges are possible (e.g., at least 90 wt % and less than or equal to 99 wt %). Other ratios are also possible. Blends of more than two polymers or copolymers are also possible.

In some embodiments, the first polymer of the copolymer (or polymer blend) is non-reactive and the second polymer of the copolymer (or polymer blend) is chemically reactive.

The material forming the fluidic device and any associated components (e.g., a cover, a substrate, an article, a layer) may be hard or flexible. Those of ordinary skill in the art can readily select suitable material(s) based upon e.g., its rigidity, its inertness to (e.g., freedom from degradation by) a fluid to be passed through it, its ability to be functionalized (e.g., with a biomolecule (e.g. protein) or other entity that may be involved in, or associated with, an analysis to be performed), its robustness at a temperature at which a particular device is to be used, its transparency/opacity to electromagnetic waves (e.g., light in the ultraviolet and visible regions, terahertz waves, microwaves, and so on), its water vapor permeability, and/or the method used to fabricate features in the material. For instance, for molded or extruded articles, the material used may include a thermoplastic (e.g., polypropylene, polyethylene, polystyrene, poly (styrene-co-acrylonitrile), poly(styrene-co-butadiene), poly (acrylonitrile, butadiene, styrene), poly(styrene-co-maleic anhydride), poly(styrene-co-acrylate), poly(styrene-co-methyl methacrylate), poly(methyl methacrylate), polycarbonate, PVC, PTFE, PET, cyclo-olefin polymers or copolymers, or blends of two or more such polymers), an elastomer (e.g., polyisoprene, isobutene-isoprene, nitrile, neoprene, ethylene-propylene, hypalon, poly(dimethylsiloxane), silicone), a thermoset (e.g., epoxy, unsaturated polyesters, phenolics), or combinations thereof. The article may be formed by injection molding in certain embodiments. In some embodiments, fluidic devices including two or more components, layers, or substrates may be formed in different materials to tailor the components to the major function(s) of the each of the components, e.g., based upon the factors described herein.

In some embodiments, a material used to form a fluidic device, or portions thereof (e.g., a substrate, an article, a layer, a component) may be chosen, at least in part, for its water vapor permeability. For instance, all or portions of a section or component of a device (e.g., a substrate, an article, a layer) may have a water vapor permeability of, for example, less than or equal to about 10.0 g·mm/m$^2$·d, less than or equal to about 7.0 g·mm/m$^2$·d, less than or equal to about 5.0 g·mm/m$^2$·d, less than or equal to about 4.0 g·mm/m$^2$·d, less than or equal to about 3.0 g·mm/m$^2$·d, less than or equal to about 2.0 g·mm/m$^2$·d, less than or equal to about 1.0 g·mm/m$^2$·d, less than or equal to about 0.5 g·mm/m$^2$·d, less than or equal to about 0.3 g·mm/m$^2$·d, less than or equal to about 0.1 g·mm/m$^2$·d, less than or equal to about 0.05 g·mm/m$^2$·d, less than or equal to about 0.03 g·mm/m$^2$·d, less than or equal to about 0.02 g·mm/m$^2$·d, less than or equal to about 0.01 g·mm/m$^2$·d, less than or equal to about 0.005 g·mm/m$^2$·d, less than or equal to about 0.001 g·mm/m$^2$·d, or less than or equal to about 0.0005 g·mm/m$^2$·d. In some embodiments, the water vapor permeability may be at least 0.001 g·mm/m$^2$·d, at least 0.01 g·mm/m$^2$·d, at least 0.02 g·mm/m$^2$·d, at least 0.05 g·mm/m$^2$·d, at least 0.1 g·mm/m$^2$·d, at least 0.3 g·mm/m$^2$·d, at least 0.5 g·mm/m$^2$·d, at least 1.0 g·mm/m$^2$·d, at least 2.0 g·mm/m$^2$·d, at least 3.0 g·mm/m$^2$·d, at least 4.0 g·mm/m$^2$·d, at least 5.0 g·mm/m$^2$·d, or at least 10.0 g·mm/m$^2$·d. In some cases, the water vapor permeability may be, for example, between about 0.001 g·mm/m$^2$·d and 0.01 g·mm/m$^2$·d, between about 0.01 g·mm/m$^2$·d and about 2.0 g·mm/m$^2$·d, between about 0.01 g·mm/m$^2$·d and about 1.0 g·mm/m$^2$·d, between about 0.01 g·mm/m$^2$·d and about 0.4 g·mm/m$^2$·d, between about 0.01 g·mm/m$^2$·d and about 0.04 g·mm/m$^2$·d, or between about 0.01 g·mm/m$^2$·d and about 0.1 g·mm/m$^2$·d. Combinations of the above-referenced ranges are also possible. Other ranges are also possible. The water vapor permeability may be measured at, for example, 40° C. at 90% relative humidity (RH). It should be appreciated that different portions of a device (e.g., substrates, articles, layers, components) may have different combinations of the above-references ranges for water vapor permeability. In some embodiments, a material having a water vapor permeability in one or more of the above-referenced ranges may be used to form a component of a device including, for example, an incubation channel, a detection channel, a channel used for storing a reagent, an intervening channel, a bridging channel, and/or a channel of the sample collector.

In some embodiments, a material used to form a fluidic device, or portions thereof (e.g., a substrate, an article, a layer, a component) may be chosen, at least in part, for its optical transmission. For instance, all or portions of a section or component of a device (e.g., a substrate, an article, a layer) may have an optical transmission of at least 90% between 400 and 800 nm wavelengths of light (e.g., light in the visible range). Optical transmission may be measured through a material having a thickness of, for example, at least about 2 mm (or in other embodiments, at least about 1 mm or at least about 0.1 mm). In some instances, the optical transmission may be at least 80%, at least 85%, at least 88%, at least 92%, at least 94%, or at least 96% between 400 and 800 nm wavelengths of light. In certain embodiments, the optical transmission may be less than 100%, less than or equal to 98%, less than or equal to 96%, less than or equal to 94%, less than or equal to 92%, less than or equal to 90%, less than or equal to 85%, less than or equal to 80%, less than or equal to 50%, less than or equal to 30%, or less than or equal to 10% between 400 and 800 nm wavelengths of light. Combinations of the above-referenced ranges are possible. Other values are also possible. It should be appreciated that different portions of a device (e.g., substrates, articles, layers, components) may have different combinations of the above-references ranges for optical transmission. In some embodiments, a material having an optical transmission in one or more of the above-referenced ranges may be used to form a component of a device including, for example, an incubation channel, a detection channel, a channel used for storing a reagent, an intervening channel, a bridging channel, and/or a channel of the sample collector.

In some embodiments, a material used to form all or a portion of a fluidic device (e.g., a substrate, an article, a layer, a component), such as a reaction area/analysis region, may include an additive. The addive may, for example, improve performance of optical measurements at the reaction area/analysis region compared to a similar component or portion of the device but absent the additive. For instance, in some embodiments, the additive may improve luminescence measurements (e.g., fluorescence, time-resolved fluorescence, chemiluminescence, electro-chemiluminescence, or other measurement-types described herein). Non-limiting examples of additives include an opaque filler (e.g., white opaque filler, black opaque filler) and a dye (e.g., a dye having an absorbance band overlapping with the auto-fluorescence of the material or resin used to form the component or portion of the device).

In some embodiments, a fluidic device, or portions thereof (e.g., a substrate, an article, a layer, a component) may be formed in a material that makes it more suitable for processing under certain conditions. For example, a material may be chosen in part based on its melting temperature to allow it to be compatible with certain fabrication tools and/or methods (e.g., for forming channels of certain dimensions) such as those described herein. In some embodiments, a fluidic device, or portions thereof (e.g., a substrate, an article, a layer, a component) may be formed in a material having a melting temperature of at least about 80° C., at least about 100° C., at least about 130° C., at least about 160° C., or at least about 200° C. In certain embodiments, the material may have a melting temperature of less than or equal to about 200° C., less than or equal to about 160° C., less than or equal to about 130° C., less than or equal to about 100° C., or less than or equal to about 80° C. Other melting temperatures are also possible. It should be appreciated that different portions of a device (e.g., substrates, articles, layers, components) may have different combinations of the above-references ranges for melting temperature. In some embodiments, a material having a melting temperature in one or more of the above-referenced ranges may be used to form a component of a device including, for example, an incubation channel, a detection channel, a channel used for storing a reagent, an intervening channel, a bridging channel, and/or a channel of the sample collector.

In some embodiments, a fluidic device, or portions thereof (e.g., a substrate, an article, a layer, a component) may be formed in a material having a certain glass transition temperature ($T_g$). For instance, in some embodiments, the glass transition temperature of a material may be greater than or equal to about 75° C., greater than or equal to about 80° C., greater than or equal to about 85° C., greater than or equal to about 90° C., greater than or equal to about 95° C., greater than or equal to about 100° C., greater than or equal to about 105° C., greater than or equal to about 110° C., greater than or equal to about 115° C., greater than or equal to about 120°

C., greater than or equal to about 125° C., greater than or equal to about 130° C., greater than or equal to about 135° C., greater than or equal to about 140° C., greater than or equal to about 150° C., greater than or equal to about 160° C., greater than or equal to about 170° C. In some instances, the glass transition temperature of a material may be less than or equal to about 170° C., less than or equal to about 160° C., less than or equal to about 150° C., less than or equal to about 140° C., less than or equal to about 130° C., less than or equal to about 120° C., less than or equal to about 110° C., less than or equal to about 100° C., less than or equal to about 90° C., less than or equal to about 80° C., or equal to about 70° C. Combinations of the above-referenced ranges are also possible (e.g., greater than or equal to about 80° C. and less than or equal to about 140° C.). Other values of glass transition temperature of the first component are also possible. The glass transition temperature of a material may be determined using differential scanning calorimetry (DSC), thermomechanical analysis (TMA), dynamic mechanical analysis (DMA), or may be obtained from a manufacturer's specifications.

In some instances, a fluidic device is comprised of a combination of two or more materials, such as the ones listed above. For instance, channels of the fluidic device may be formed in polystyrene or other polymers (e.g., by injection molding) and a tape such as a biocompatible tape (e.g., a tape compatible with the biological and chemical reagents used in the assay) may be used to seal the channels. The tape or flexible material may include a material known to improve vapor barrier properties (e.g., metal foil, polymers or other materials known to have high vapor barriers), and may optionally allow access to inlets and outlets by puncturing or unpeeling the tape. A variety of methods can be used to seal a microfluidic channel or portions of a channel, or to join multiple layers of a device, including but not limited to, the use of adhesives, use adhesive tapes (e.g., pressure-sensitive adhesives), gluing, solvent bonding, plasma-activated thermal bonding, UV-activated thermal bonding, welding, brazing, lamination of materials, or by mechanical methods (e.g., clamping, snapping mechanisms, etc.).

The choice of the bonding technique can be influenced by the temperature at which the device will be exposed during storage and operation. Adhesives and glues may flow and produce interference with the flow of sample and/or reagents on devices, when exposed to elevated temperatures, especially during the operation of the device when pressure difference are applied between the microfluidic channels and the ambient conditions. Application of vacuum in the channels may result in flow of adhesive (or glue) from the interface between two surfaces towards the microfluidic channels, and interfere with the flow. Application in the channels of a pressure greater than ambient pressure (or exposure of the product to a depressurized environment) may result in delamination of the cover in the vicinity of the channels and erratic flow performances. Accordingly, one or more of these factors may be considered when choosing appropriate materials and/or methods for forming the fluidic device. For example, in some embodiments involving heating of the device, microfluidic channels may be covered with an adhesive-free lid/cover using solvent bonding.

In some embodiments, a first material used to form a first portion of a fluidic device (e.g., a substrate, an article, a layer) may include a channel (e.g., an incubation channel, a detection channel, a channel used for storing a reagent, an intervening channel, a bridging channel, and/or a channel of a sample collector) having one or more corners (e.g., curved corners) having a particular radius of curvature, such as a radius of curvature within one or more of the ranges noted above. In certain embodiments, the first material may be a copolymer described herein (and in particular, may include a first polymer component and a second polymer component as described above), and the channel may have a radius of curvature within one or more of the ranges noted above. In some instances involving a material having first and second polymer components, the second polymer component includes a reactive group for further functionalization of the first material. The second polymer component may be functionalized with, for example, a biomolecule (e.g. protein) or other entity that may be involved in, or associated with, an analysis to be performed, In certain embodiments, the first material may have an optical transmission as described herein, e.g., 90% between 400 nm and 800 nm wavelengths of light. In some instances, the first portion of the fluidic device (e.g., a substrate, an article, a layer) is formed by a molding process (e.g., injection molding). The first portion of the fluidic device may mate with a cover (e.g., a first cover layer), which may be used to enclose a channel of the first portion of the fluidic device. Other configurations are also possible.

In some embodiments, a second material used to form a second portion of a fluidic device (e.g., a substrate, an article, a layer) may have a water vapor permeability of less than about 0.05 g·mm/mm$^2$·d. The second portion of the fluidic device may include a channel (e.g., an incubation channel, a detection channel, a channel used for storing a reagent, an intervening channel, a bridging channel, and/or a channel of a sample collector) having one or more corners (e.g., curved corners) having a particular radius of curvature, such as a radius of curvature within one or more of the ranges noted above. The second portion of the fluidic device may mate with a cover (e.g., a second cover layer), which may be used to enclose a channel of the second portion of the fluidic device. Other configurations are also possible.

In some embodiments, the first material may have a water vapor permeability higher than the water vapor permeability of the second material.

In some embodiments, the first material may have a glass transition temperature higher than the glass transition temperature of the second material. In other embodiments, the first material may have a glass transition temperature lower than the glass transition temperature of the second material.

In one particular set of embodiments, the first material is used to form a first layer of a fluidic device, and the second material is used to form a second layer of the fluidic device. The first and second layers may be integrally connected to one another in some embodiments. As used herein, the term "integrally connected," when referring to two or more objects, means objects that do not become separated from each other during the course of normal use, e.g., cannot be separated manually; separation requires at least the use of tools, and/or by causing damage to at least one of the components, for example, by breaking, peeling, or separating components fastened together via adhesives or tools. Integrally connected components may be irreversibly attached to one another during the course of normal use e.g., by use of an adhesive or by other bonding methods. In other embodiments, two or more layers may be reversibly attached to one another.

The methods and systems described herein may involve variety of different types of analyses, and can be used to determine a variety of different samples. In some cases, an analysis involves a chemical and/or biological reaction. In some embodiments, a chemical and/or biological reaction involves binding. Different types of binding may take place in fluidic devices described herein. Binding may involve the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of molecules including proteins, nucleic acids, glycoproteins, carbohydrates, hormones, and the like. Specific examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc. Binding may also occur between proteins or other components and cells. In addition, devices described herein may be used for other fluid analyses (which may or may not involve binding and/or reactions) such as detection of components, concentration, etc.

In some embodiments, a chemical and/or biological reaction involves a reducing agent (e.g., hydroquinone, chlorohydroquinone, pyrogallol, metol, 4-aminophenol and phenidone, $Fe(+2)$, $Ti(+3)$, and $V(+2)$). In some cases, a chemical and/or biological reaction involves a metal precursor (e.g., a solution of a metal salt, such as a silver salt or gold salt).

In some cases, a heterogeneous reaction (or assay) may take place in a fluidic device; for example, a binding partner may be associated with a surface of a channel, and the complementary binding partner may be present in the fluid phase. Other solid-phase assays that involve affinity reaction between proteins or other biomolecules (e.g., DNA, RNA, carbohydrates), or non-naturally occurring molecules (e.g., aptamers, or peptoids), can also be performed. In some embodiments, a binding partner may include a biomolecule such as an antibody, a small molecule attached to an antibody, bovine serum albumin or other protein, and/or an antigen such as a cell surface protein and peptide, the binding partner may be attached, in some embodiments, to a surface of a channel, e.g., by reaction with a second polymer component described herein. Non-limiting examples of typical reactions that can be performed in a fluidic device include chemical reactions, enzymatic reactions, immuno-based reactions (e.g., antigen-antibody), and cell-based reactions.

A biomolecule or other entity can be associated with a surface of the fluidic device (e.g., a surface of a channel) in any suitable manner. For example, a biomolecule or other entity may be cross-linked, covalently bound, ionically bound, absorbed, adsorbed (physisorbed), or otherwise present on a surface and/or within the fluidic device (e.g., in a channel of the device). In some embodiments, the biomolecule or other entity is a lyophilized molecule, a substantially dry molecule, a labelled molecule, a conditioning molecule, a pH modifier, a viscosity modifier, and/or a surfactant. In certain embodiments, the biomolecule or other entity is a reagent for a chemical and/or biological reaction (e.g., a binding reaction), or a linker for such a reagent. Non-limiting examples of analytes that can be determined (e.g., detected) using fluidic devices described herein include specific proteins, viruses, hormones, drugs, nucleic acids and polysaccharides; specifically antibodies, e.g., IgD, IgG, IgM or IgA immunoglobulins to HTLV-I, HIV, Hepatitis A, B and non A/non B, Rubella, Measles, Human Parvovirus B19, Mumps, Malaria, Chicken Pox or Leukemia; autoantibodies; human and animal hormones, e.g., thyroid stimulating hormone (TSH), thyroxine (T4), vitamin D, vitamin B12, luteinizing hormone (LH), follicle-stimulating hormones (FSH), testosterone, progesterone, human chorionic gonadotropin, estradiol; other proteins or peptides, e.g. troponin I, troponin T, c-reactive protein, myoglobin, brain natriuretic protein, prostate specific antigen (PSA), free-PSA, intact PSA, complexed-PSA, pro-PSA, EPCA-2, PCADM-1, ABCA5, free-hK2, total hK2, beta-MSP (PSP94), AZGP1, Annexin A3, PSCA, PSMA, JM27, PAP; drugs, e.g., paracetamol or theophylline; marker nucleic acids, e.g., PCA3, TMPRS-ERG; polysaccharides such as cell surface antigens for HLA tissue typing and bacterial cell surface material. Chemicals that may be detected include explosives such as TNT, nerve agents, and environmentally hazardous compounds such as polychlorinated biphenyls (PCBs), dioxins, hydrocarbons, and MTBE. Typical sample fluids include physiological fluids such as human or animal whole blood, blood serum, blood plasma, semen, tears, urine, sweat, saliva, cerebro-spinal fluid, vaginal secretions; in-vitro fluids used in research or environmental fluids such as aqueous liquids suspected of being contaminated by the analyte.

In some embodiments, one or more reagents that can be used to determine an analyte of a sample (e.g., a binding partner of the analyte to be determined) is stored and/or sealed in a channel or chamber of a fluidic device, e.g., prior to first use, in order to perform a specific test or assay.

In cases where an antigen is being analyzed, a corresponding antibody or aptamer can be the binding partner associated with a surface of a microfluidic channel. If an antibody is the analyte, then an appropriate antigen or aptamer may be the binding partner associated with the surface. When a disease condition is being determined, it may be preferred to put the antigen on the surface and to test for an antibody that has been produced in the subject. Such antibodies may include, for example, antibodies to HIV.

In some embodiments, a fluidic device is adapted and arranged to perform an analysis involving accumulating an opaque material on a region of a channel, exposing the region to light, and determining the transmission of light through the opaque material. An opaque material may include a substance that interferes with the transmittance of light at one or more wavelengths. An opaque material does not merely refract light, but reduces the amount of transmission through the material by, for example, absorbing or reflecting light. Different opaque materials or different amounts of an opaque material may allow transmittance of less than, for example, 90, 80, 70, 60, 50, 40, 30, 20, 10, or 1 percent of the light illuminating the opaque material. Examples of opaque materials include molecular layers of metal (e.g., elemental metal), ceramic layers, dyes, polymeric layers, and layers of an opaque substance (e.g., a dye). The opaque material may, in some cases, be a metal that can be electrolessly deposited. These metals may include, for example, silver, gold, copper, nickel, cobalt, palladium, and platinum. Precursors of these metals may be stored and/or flowed in the devices described herein.

An opaque material that forms in a channel may include a series of discontinuous independent particles that together form an opaque layer, but in one embodiment, is a continuous material that takes on a generally planar shape. The opaque material may have a dimension (e.g., a width of length) of, for example, greater than or equal to 1 micron, greater than or equal to 5 microns, greater than 10 microns, greater than or equal to 25 microns, or greater than or equal to 50 microns. In some cases, the opaque material extends across the width of the channel (e.g., an analysis region) containing the opaque material. The opaque layer may have a thickness of, for example, less than or equal to 10 microns, less than or equal to 5 microns, less than or equal to 1 micron, less than or equal to 100 nanometers or less than or equal to 10 nanometers. Even at these small thicknesses, a detectable change in transmittance can be obtained. The opaque layer may provide an increase in assay sensitivity when compared to techniques that do not form an opaque layer.

In one set of embodiments, a fluidic device described herein is used for performing an immunoassay (e.g., for human IgG or PSA) and, optionally, uses silver enhancement for signal amplification. In such an immunoassay, after delivery of a sample (e.g., containing human IgG) to a reaction site or analysis region, binding between two components (e.g., between the human IgG and anti-human IgG) can take place. One or more reagents, which may be optionally stored in a channel of the device prior to use, can then flow over this binding pair complex. Optionally, one of the stored reagents may include a solution of metal colloid (e.g., a gold conjugated antibody) that specifically binds to the antigen to be detected (e.g., human IgG). In other embodiments, the metal colloid can be bound with the sample prior to arriving at the reaction site or analysis region. This metal colloid can provide a catalytic surface for the deposition of an opaque material, such as a layer of metal (e.g., silver), on a surface of the analysis region. The layer of metal can be formed by using a two component system: a metal precursor (e.g., a solution of silver salts) and a reducing agent (e.g., hydroquinone, chlorohydroquinone, pyrogallol, metol, 4-aminophenol and phenidone, Fe(+2), Ti(+3), and V(+2)), which can optionally be stored in different channels prior to use.

Mixing and/or incubation of the two reagents can be performed using the methods described herein. In certain embodiments, as a positive or negative pressure differential is applied to the system, the silver salt and reducing solutions can be combined and mixed (e.g., due to diffusion) in a channel (e.g., an incubation channel), and then flow over the analysis region. If antibody-antigen binding occurs in the analysis region, the flowing of the metal precursor solution through the region can result in the formation of an opaque layer, such as a silver layer, due to the presence of the catalytic metal colloid associated with the antibody-antigen complex. The opaque layer may include a substance that interferes with the transmittance of light at one or more wavelengths. An opaque layer that is formed in the channel can be detected optically, for example, by measuring a reduction in light transmittance through a portion of the analysis region (e.g., a serpentine channel region) compared to a portion of an area that does not include the antibody or antigen.

Alternatively, a signal can be obtained by measuring the variation of light transmittance as a function of time, as the film is being formed in an analysis region. The opaque layer may provide an increase in assay sensitivity when compared to techniques that do not form an opaque layer. Additionally, various amplification chemistries that produce optical signals (e.g., absorbance, fluorescence, glow or flash chemiluminescence, electrochemiluminescence), electrical signals (e.g., resistance or conductivity of metal structures created by an electroless process), or magnetic signals (e.g., magnetic beads) can be used to allow detection of a signal by a detector.

Various types of fluids can be used with the fluidic devices described herein. As described herein, fluids may be introduced into the fluidic device at first use, and/or stored within the fluidic device prior to first use. Fluids include liquids such as solvents, solutions, and suspensions. Fluids also include gases and mixtures of gases. The fluids may contain any suitable species such as a component for a chemical and/or biological reaction, a buffer, and/or a detecting agent. When multiple fluids are contained in a fluidic device, the fluids may be separated by another fluid that is preferably substantially immiscible in each of the first two fluids. For example, if a channel contains two different aqueous solutions, a separation plug of a third fluid may be substantially immiscible in both of the aqueous solutions. When aqueous solutions are to be kept separate, substantially immiscible fluids that can be used as separators may include gases such as air or nitrogen, or hydrophobic fluids that are substantially immiscible with the aqueous fluids. Fluids may also be chosen based at least in part on the fluid's reactivity with adjacent fluids, or based on other factors described herein. For example, an inert gas such as nitrogen may be used in some embodiments and may help preserve and/or stabilize any adjacent fluids. An example of a substantially immiscible liquid for separating aqueous solutions is perfluorodecalin.

The choice of a separator fluid may be made based on other factors as well, including any effect that the separator fluid may have on the surface tension of the adjacent fluid plugs. In some embodiments, it may be preferred to maximize the surface tension within any fluid plug to promote retention of the fluid plug as a single continuous unit under varying environmental conditions such as vibration, shock, and temperature variations. Other factors relevant to mixing between fluids and fluid plugs can also be considered as described herein.

Separator fluids may also be inert to a reaction site (e.g., an analysis region) to which the fluids will be supplied. For example, if a reaction site includes a biological binding partner, a separator fluid such as air or nitrogen may have little or no effect on the binding partner. The use of a gas (e.g., air) as a separator fluid may also provide room for expansion within a channel of a fluidic device should liquids contained in the device expand or contract due to changes such as temperature (including freezing) or pressure variations.

In some embodiments, a fluidic device may be used in connection with an analyzer that may include one or more detectors (e.g., optical system that may include detector(s) and/or light source(s)), temperature control systems (e.g., heater(s)/cooler(s)), pressure-control system (e.g., configured to pressurize the at least one channel in the cassette to move the sample through the at least one channel). For example, an analyzer as described in more detail in U.S. Patent Publication No. 2011/0256551, filed Apr. 15, 2011, entitled "Systems and Devices for Analysis of Samples," may be used.

Any suitable heater can be used to heat a fluid in a fluidic device. In some embodiments, the heater is a part of an analyzer as described herein, although other configurations are also possible. In some cases, a heater includes a resistive heater (e.g., a 12 volt 10 watt resistive heater) sandwiched between a conductive bracket (e.g., a sheet metal bracket) and a conductive plate (e.g., an anodized aluminum plate). The resistive heater may be designed with a through hole at the center of the component; this through hole can allow for a thermistor to be mounted to the anodized aluminum plate. The conductive plate may have a thickness of, for example, about 4 mm at the area where the heater is located. The flat surface of the conductive plate above where the heater is located is the area where the assay cassette can rest (e.g., when the cassette is inserted into the analyzer). For instance, when a solenoid is activated it can apply a force on the assay cassette that is inserted in the analyzer, causing it to become into intimate/physical contact with the flat surface of the conductive plate. The conductive plate conducts and transfers heat from the heater to the assay cassette. The heat then transfers through the lid/cover (e.g., COC lid) of the assay cassette (e.g., a top or bottom of the cassette). The lid or cover may have, for example, a thickness of about 0.004" (or 100 micrometers). The heat applied to the lid/cover can heat up a sample contained inside a channel (e.g., microfluidic channel, incubation channel) of the assay cassette.

Accordingly, in some embodiments, a heater (e.g., used to heat a sample or reagent) includes a conductive plate that is positioned in direct (or indirect) contact with a surface of a fluidic device. The heater may be used to heat all or portions of the device. For instance, the heater may be positioned over, or adjacent to, an incubation channel, but not over/adjacent other components or areas of the device (e.g., a detection zone).

In some embodiments, the heater (e.g., resistive heater) may include a conductor contained within a material (e.g., an insulating material such as silicone rubber). As current passes through the conductive material, heat is generated. The thermistor mounted to the conductive plate may be used to measure temperature of the plate. The resistance of the thermistor is dependent on the temperature it is exposed to. The analyzer may use a PID loop to regulate the temperature of this system.

A variety of determination (e.g., measuring, quantifying, detecting, and qualifying) techniques may be used, e.g., to analyze a sample component or other component or condition associated with a fluidic described herein. Determination techniques may include optically-based techniques such as light transmission, light absorbance, light scattering, light reflection, and visual techniques. Determination techniques may also include luminescence techniques such as photoluminescence (e.g., fluorescence, time-resolved fluorescence), chemiluminescence, bioluminescence, and/or electrochemiluminescence. In other embodiments, determination techniques may measure conductivity or resistance. As such, an analyzer may be configured to include such and other suitable detection systems.

Different optical detection techniques provide a number of options for determining reaction (e.g., assay) results. In some embodiments, the measurement of transmission or absorbance means that light can be detected at the same wavelength at which it is emitted from a light source. Although the light source can be a narrow band source emitting at a single wavelength it may also may be a broad spectrum source, emitting over a range of wavelengths, as many opaque materials can effectively block a wide range of wavelengths. In some embodiments, a system may be operated with a minimum of optical devices (e.g., a simplified optical detector). For instance, the determining device may be free of a photomultiplier, may be free of a wavelength selector such as a grating, prism or filter, may be free of a device to direct or collimate light such as a collimator, or may be free of magnifying optics (e.g., lenses). Elimination or reduction of these features can result in a less expensive, more robust device.

Additional examples of detection systems are described in more detail below in U.S. Patent Publication No. 2011/0256551, filed Apr. 15, 2011 and entitled "Systems and Devices for Analysis of Samples," which is incorporated herein by reference in its entirety for all purposes.

The articles, components, systems, and methods described herein may be combined with those described in International Patent Publication No. WO2005/066613 (International Patent Application Serial No. PCT/US2004/043585), filed Dec. 20, 2004 and entitled "Assay Device and Method" [H0498.70211WO00]; International Patent Publication No. WO2005/072858 (International Patent Application Serial No. PCT/US2005/003514), filed Jan. 26, 2005 and entitled "Fluid Delivery System and Method" [H0498.70219WO00]; International Patent Publication No. WO2006/113727 (International Patent Application Serial No.PCT/US06/14583), filed Apr. 19, 2006 and entitled "Fluidic Structures Including Meandering and Wide Channels" [H0498.70244WO00]; U.S. Pat. No. 8,202,492, issued Jun. 19, 2012 (filed May 1, 2008) and entitled "Fluidic Connectors and Microfluidic Systems" [C1256.70000US01]; U.S. Patent Publication No. 2009/0075390, filed Aug. 22, 2008, entitled "Liquid Containment for Integrated Assays" [C1256.70001US01]; U.S. Pat. No. 8,222,049, issued Jul. 17, 2012 (filed Apr. 25, 2008), entitled "Flow Control in Microfluidic Systems" [C1256.70002US01]; U.S. Pat. No. 8,221,700, issued Jul. 17, 2012 (filed Feb. 2, 2010), entitled "Structures for Controlling Light Interaction with Microfluidic Devices," [C1256.70003US01]; U.S. Patent Publication No. 2010/0158756, filed Dec. 17, 2009, entitled "Reagent Storage in Microfluidic Systems and Related Articles and Methods," [C1256.70004US01]; U.S. Patent Publication No. 2011/0120562, filed Nov. 24, 2010, entitled "Fluid Mixing and Delivery in Microfluidic Systems," [C1256.70005US01]; U.S. Patent Publication No. 2011/0253224, filed Apr. 15, 2011, entitled "Feedback Control in Microfluidic Systems," [C1256.70006US01]; U.S. Patent Publication No. 2011/0256551, filed Apr. 15, 2011, entitled "Systems and Devices for Analysis of Samples," [C1256.70010US01]; U.S. Patent Publication No. 2014/0272935, filed Feb. 7, 2014, entitled "Mixing of Fluids in Fluidic Systems," [C1256.70011US01], each of which is incorporated herein by reference in its entirety for all purposes.

In some embodiments, the articles, devices, and/or methods described herein can be used to diagnose, prevent, treat, or manage certain diseases or bodily conditions, or determine if a patient is eligible for food supplementation or other therapy, especially those associated with varying levels of vitamin D. In one example, the articles, devices, and/or methods described herein may involve a test for vitamin D that is used in clinical practice to select patients eligible for food supplementation or other therapy (therapeutics, drugs, biologicals or pharmaceuticals) that can modulate (increase or decrease) the level of vitamin D in the patient blood stream (25-OH D2, 25-OH D3, 1,25-OHD2, 1,25-OH-D3). People in normal populations not exposed to sufficient sunlight (e.g., in the winter time in northern parts of the northern hemisphere) may lack sufficient quantities of vitamin D in their blood. A level of vitamin D greater than 50 ng/mL in 25(OH)D is considered normal, whereas levels at 30-50 ng/mL are considered as potentially deficient. At Vitamin D levels below 30 ng/mL, the patient is subject to vitamin D deficiency, which can result in broad ranges of symptoms, including impaired immune system functioning, rickets, insulin resistance, thin or brittle bones, and elevated risk for osteoporosis. Some conditions may be treated by intake of vitamin D, and therefore would benefit from a diagnostic measure of vitamin D. These conditions include hypophosphatemia, kidney diseases, osteomalacia, psoriasis, rickets, thyroid conditions, dental cavities, muscle weakness/pain, osteoporosis, renal osteodystrophy, and autoimmune diseases. Accordingly, the articles, devices, and/or methods described herein may be used (at least in part) to diagnose, prevent, treat, or manage one or more such diseases or bodily conditions in some embodiments.

The role of vitamin D has also been weakly associated with a number of heath indications including asthma, autoimmune diseases, bone density (children), bone diseases (kidney disease or kidney transplant), cancer prevention (breast, colorectal, prostate, other), cognition, fertility, fibromyalgia (long-term, body-wide pain), fractures (prevention and/or treatment), hepatic osteodystrophy (bone disease in people with liver disease), high blood pressure, HIV infection, immune function, increasing lifespan, inflammatory bowel disease, kidney disease (chronic), loose teeth, mood disorders, multiple sclerosis, muscle strength, muscle wasting/weakness, myelodysplastic syndrome (disease of blood cell production), osteoarthritis, osteogenesis imperfecta (disorder in which bones break easily), osteomalacia (bone softening caused by anti-seizure drugs), osteoporosis (due to corticosteroids, drugs, and/or cystic fibrosis), pregnancy, prevention of respiratory tract infections, seasonal affective disorder (SAD), senile warts, sexual dysfunction, skin conditions, skin pigmentation disorders, stroke, tuberculosis, Type 1 diabetes, Type 2 diabetes, vitiligo (irregular white patches on the skin), weight gain (in women with menopause), atopic eczema (skin condition causing itchy, scaly rashes), cancer treatment (prostate), heart disease, high cholesterol. The articles, devices, and/or methods described herein may be used (at least in part) to diagnose, prevent, treat, or manage one or more such diseases or bodily conditions in some embodiments.

In one set of embodiments, the articles, devices, and/or methods described herein may involve an assay for clinical use that may be designed to measure the total vitamin D in the sample. The assay may involve, for example, determination of multiple markers including the concentration of free vitamin D or bioavailable vitamin D, the concentration of albumin, the concentration of vitamin D binding protein and/or the concentration of intact PTH (parathyroid hormone). The concentration of the total vitamin D can be extrapolated with an algorithm that relies on the multiple markers. Other factors may be included in the algorithm, including gender, pregnancy, and/or race. An algorithm may also rely on the measured or calculated affinity between vitamin D and the vitamin D binding protein of the patient, as normal differences in such affinity can be found across normal individuals. In some embodiments, the amount of bioavailable vitamin D may be determined based on the difference in affinity between vitamin D and selected carrier proteins; the affinity constant of albumin for vitamin D is $6 \cdot 10^5$ M$^{-1}$, and the affinity between vitamin D binding protein and vitamin D is $9.3 \cdot 10^8$ M$^{-1}$. The affinity between vitamin D and the vitamin D binding protein of the patient may be measured or calculated using an assay in an article, device, and/or method described herein.

In one set of embodiments, the articles, devices, and/or methods described herein may involve an assay for 1,25 (OH) vitamin D. 25-OH vitamin D3 (calcifediol) is a prohormone of the active form of vitamin D3, 1,25(OH) vitamin D3 (calcitriol). 25-hydroxyergocalciferol (also known as 25-hydroxyvitamin D2, or 25(OH)D2) may also be converted into 1,25(OH) vitamin D. Since the 1,25(OH) forms are the most biologically active, a clinical assay for vitamin D may be designed to quantify the concentration of 1,25 (OH) in the blood (or serum or plasma components). The assay for 1,25(OH) vitamin D may benefit from being equimolar between the D2 and D3 forms, and may, for example, directly measure the free 1,25(OH) vitamin D, the biologically available 1,25(OH) vitamin D, and/or the total 1,25(OH) vitamin D. In some embodiments, algorithms relying on the concentration of free 1,25(OH) vitamin D, or bioavailable 1,25(OH) vitamin D, the concentration of albumin, the concentration of vitamin D binding protein and/or the concentration of intact PTH (parathyroid hormone) can be used to calculate (e.g., extrapolate) the concentration of total 1,25(OH) vitamin D from the measured data.

In one set of embodiments, the articles, devices, and/or methods described herein may involve an assay that is calibrated to determine a value for the vitamin D in a whole blood sample that correlates with the value for the vitamin D in a plasma or serum sample, as obtained by commercial immunoassay system or a validated LC/MS method. The fluidic device may be designed such that normal variations in hematocrit between samples do not significantly impact the calibration of the assay or the accuracy of the vitamin D measurement in the samples across a range of hematocrit between 20% and 65% (e.g., at least 20%, at least 30%, at least 40%, at least 50%; and/or less than or equal to 65%, less than or equal to 55%, less than or equal to 45%, less than or equal to 35%, or combinations thereof). More specifically, any or all of following parameters may be varied to allow a continuous flow of the sample when the sample interacts with the surface of the detection zone: the size of the channel (depth, width and length), the sample volume and viscosity, and the applied vacuum. In some embodiments, the method may involve implementing flow conditions such that the blood cells may move away from the surface of the channel (e.g., microchannel), leaving only the plasma component of the sample to interact with the surface (where the immunoreaction takes place). In this configuration, the presence of blood cells does not interfere with the kinetics of the binding of anti-vitamin D antibodies to the surface coated with a vitamin D derivative (such as a vitamin D conjugate of mouse IgG, BSA or other carrier proteins).

In some embodiments, the articles, devices, and/or methods described herein can involve a vitamin D assay that is used as a companion diagnostic for therapeutics (or another drug, in general). A method may involve, for example, administering a drug to a patient and then determining one or more levels of vitamin D (e.g., bioavailable vitamin D, vitamin D free in solution, vitamin D bound to proteins other than the vitamin D binding protein, vitamin D binding protein, total endogenous vitamin D) using an articles, devices, and/or method described herein.

For example, the vitamin D assay can be used as a companion diagnostic for therapeutics (or other drugs in general) whose active ingredient(s) is or includes an active form of vitamin D, including but not limited to: 25-OH D2, 25-OH D3, 1,25-OHD2, 1,25-OH-D3. The formulation of the drug may be optimized for efficient delivery to the patient, for instance by presenting the active ingredient in a formulation made of a poorly or non-water soluble material (or combination of materials including at least one such material). The material may be made of, for example, a wax, a gel, or a hydrogel. Release of the active ingredient from the material may occur at a rate that is optimized for intake by the metabolism of the patient. One such case is where the release of the active ingredient is substantially unchanged over a period of a multiple hours. That is, the instantaneous rate of release throughout a period of multiple hours is at least 0.1 times the release rate at the maximum rate of release. Other instantaneous release rates can also be appropriate, including at least 0.9, 0.5, 0.2, 0.05, 0.01, and/or 0.005 times the release rate at the maximum rate of release. Eventually, and after the intended time of release, the release rate will asymptotically approach zero. In some cases, the companion diagnostic may be used in conjunction with the drug RAYALDEE, or in conjunction with a pharmaceutical used for the control (or replenishment) of vitamin D in an adult or pediatric patient being treated for secondary hyperparathyroidism. The use of the companion diagnostic may also be used for patients with stage 3 or 4 chronic kidney disease and/or serum total 25-hydroxyvitamin D levels less than 30 ng/mL.

EXAMPLES

Example 1

This example describes conditions for release of vitamin D from its binding protein and an assay involving vitamin D performed in a fluidic device comprising a detection zone.

Vitamin D serum samples spanning the range of 10-120 ng/mL were obtained from New York Biologics, Southampton, N.Y. In order to release vitamin D from its binding protein (vitamin D binding protein) and/or from other binding entities (e.g., albumin), serum was diluted 1:10 in acetate buffer, pH adjusted to 5.5 with acetic acid, which included 2.5% of the detergent perfluorohexanoic acid and 50 ng/mL gold-labeled anti-vitamin D antibody. Nine serum samples with varying vitamin D levels were prepared: three each at approximately 10, 40 and 80 ng/mL. One mL of each sample was placed in a 1.5 mL Eppendorf tube and incubated in a heating block with metal pellets. The temperature of each sample was measured using a thermocouple to ensure that the release temperature was accurate and the heating block setting was adjusted to provide an accurate sample temperature. For each vitamin D level, one of the serum samples was heated to 40° C. for 30 minutes, one of the serum samples was heated to 40° C. for 5 minutes, and one serum sample was heated to 50° C. for 5 minutes.

After thermal treatment, the serum samples were each transferred to microfluidic cassettes which contained detection zones coated with vitamin D covalently coupled to bovine serum albumin. The microfluidic cassettes used were Sangia™ cassettes, similar to the ones described in U.S. Patent Publication No. 2011/0256551, filed Apr. 15, 2011, entitled "Systems and Devices for Analysis of Samples," and International Patent Publication No. WO2005/066613 (International Patent Application Serial No. PCT/US2004/043585), filed Dec. 20, 2004 and entitled "Assay Device and Method," which are incorporated herein by reference. The cassette was inserted into an analyzer (e.g., Claros® 1 Analyzer) as described in U.S. Patent Publication No. 2011/0256551, filed Apr. 15, 2011, entitled "Systems and Devices for Analysis of Samples," for determining the amount of vitamin D in the sample. The procedure described in Example 3 was generally followed, including the procedure for silver amplification.

Released vitamin D binds to a fraction of the gold-labeled anti-vitamin D antibodies during the release step; the remainder of the gold-labeled antibodies are unbound at this point and later bind to the immobilized vitamin D in the detection zone. Thus, the concentration of vitamin D in the initial sample (e.g., released vitamin D and free vitamin D) is inversely proportional to the measured signal level of the immobilized gold-labeled anti-vitamin D antibodies in the detection zone.

Signal responses from samples at each vitamin D level and undergoing each thermal program were compared. Table 1 compares the measured signal levels for each incubation condition.

TABLE 1

| [Vitamin-D] | B/B$_0$ | | |
|---|---|---|---|
| (ng/ml) | 5 min 40 C. n = 4 | 5 min 50 C. n = 4 | 30 min 40 C. n = 7 |
| 10 | 100% | 100% | 100% |
| 40 | 113%* | 64% | 65% |
| 80 | 92% | 24% | 21% |

*Assay imprecision may have led to a value greater than 100%.

Samples incubated for 5 minutes at 50° C. or 30 minutes at 40° C. showed significant signal reduction in the detection zone (e.g., B/B$_0$, which measures the ratio of optical absorption at a set wavelength (630 nm on a commercial plate reader or 670 nm in the Claros® 1 Analyzer) of the sample to the optical absorption at the same wavelength of serum containing no Vitamin D) for 40 ng/mL or 80 ng/mL samples, indicating greater amounts of release of vitamin D from its binding protein during thermal treatment (compared to incubation of such samples at 5 minutes at 40° C.). Samples incubated for 5 minutes at 40° C. showed either no or minor reductions in signal level, indicating the release of little vitamin D from its binding protein during thermal treatment.

Example 2

This example describes a vitamin D assay performed in a fluidic device comprising a detection zone.

Vitamin D serum samples spanning the range of 10-120 ng/mL were obtained from New York Biologics, Southampton, N.Y. In order to release vitamin D from its binding protein (vitamin D binding protein) and/or from other binding entities (e.g., albumin), serum was diluted 1:10 in pH 5.5 100 mM buffer which included 0.8% of the detergent FS50, 0.125% of the transfer molecule beta-cyclodextrin, and 50 ng/mL gold-labeled anti-vitamin D antibody. Six serum samples with varying vitamin D levels were prepared: two each at approximately 20, 60 and 90 ng/mL. One mL of each sample was placed in a 1.5 mL Eppendorf tube and incubated for 5 minutes at 50° C. in a heating block with metal pellets. The temperature of each sample was measured using a thermocouple to ensure that the release temperature was accurate and the heating block setting was adjusted to provide an accurate sample temperature. For each vitamin D level, one sample was diluted into malonate buffer and one sample was diluted into acetate buffer.

After thermal treatment, 12.5 μL of each sample were transferred to microfluidic cassettes which contained detection zones coated with vitamin D covalently coupled to bovine serum albumin. The microfluidic cassettes used were SangiaTM cassettes, similar to the ones described in U.S. Patent Publication No. 2011/0256551, filed Apr. 15, 2011, entitled "Systems and Devices for Analysis of Samples," and International Patent Publication No. WO2005/066613 (International Patent Application Serial No. PCT/US2004/043585), filed Dec. 20, 2004 and entitled "Assay Device and Method," which are incorporated herein by reference. The cassette was inserted into an analyzer (e.g., Claros® 1 Analyzer) for determining the amount of vitamin D in the sample. The procedure described in Example 3 was generally followed, including the procedure for silver amplification.

Released vitamin D binds to a fraction of the gold-labeled anti-vitamin D antibodies during the release step; the remainder of the gold-labeled antibodies are unbound at this point and later bind to the immobilized vitamin D in the detection zone. Thus, the concentration of vitamin D in the initial sample is inversely proportional to the measured signal level of the immobilized gold-labeled anti-vitamin D antibodies in the detection zone.

Figure 13:
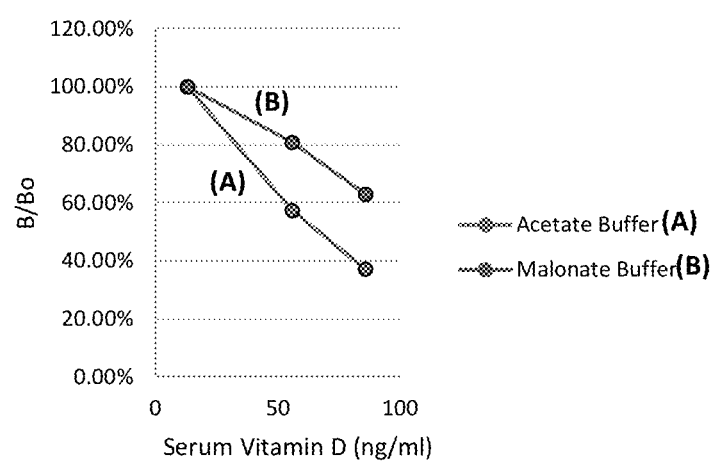
FIG. 13 shows a plot of optical readout versus time for determining binding of vitamin D using different buffers in a fluidic device according to one set of embodiments.

The signals from samples diluted into each buffer were compared. FIG. 13 shows a chart comparing the signal level from samples diluted into 100% acetate buffer to those diluted into 100% malonate buffer; it shows that both acetate and malonate buffers can serve as effective buffers for serum samples.

Example 3

This example describes a vitamin D assay performed in a fluidic device comprising a detection zone.

Vitamin D serum samples spanning the range of 10-120 ng/mL were obtained from New York Biologics, Southampton, N.Y. In order to release vitamin D from its binding protein (vitamin D binding protein) and/or from other binding entities (e.g., albumin), serum was diluted 1:10 in pH 5.5 100 mM buffer which included 0.8% of the detergent FS50, and 50 ng/mL gold-labeled anti-vitamin D antibody. Fifteen serum samples with varying vitamin D levels were prepared: five each at approximately 13, 20 and 56 ng/mL. One mL of each sample was placed in a 1.5 mL Eppendorf tube and incubated for 5 minutes at 50° C. in a heating block with metal pellets. The temperature of each sample was measured using a thermocouple to ensure that the release temperature was accurate and the heating block setting was adjusted to provide an accurate sample temperature. For each vitamin D level, the five samples were each diluted into different buffers. The five buffers used for dilution were: 30% acetate-70% malonate, 35% acetate-65% malonate, 50% acetate-50% malonate, and 60% acetate-40% malonate.

After thermal treatment, 12.5 µL of the serum samples were each transferred to microfluidic cassettes which contained detection zones coated with vitamin D covalently coupled to bovine serum albumin. The microfluidic cassettes used were Sangia™ cassettes, similar to the one shown in FIG. 5C, and as described herein and generally in U.S. Patent Publication No. 2011/0256551, filed Apr. 15, 2011, entitled "Systems and Devices for Analysis of Samples," and International Patent Publication No. WO2005/066613 (International Patent Application Serial No. PCT/US2004/043585), filed Dec. 20, 2004 and entitled "Assay Device and Method," which are incorporated herein by reference. The cassette was inserted into an analyzer (e.g., Claros® 1 Analyzer) for determining the amount of vitamin D in the sample.

The cassette included silver amplified nano-gold immunoassay technology, and included the use of a sample collector. The incubation channel of the device had a trapezoidal cross section with a maximum width of 500 um and a minimum width of 312 um, a depth of 350 um, and a length of 86.6 mm. Total volume was 12.31 uL. The detection channel had a maximum width of 120 um and a depth of 50 um. An intervening channel with a trapezoidal cross section (maximum width of 550 um and minimum width of 362 um) and depth of 350 um separated the incubation channel from the detection channel. The intervening channel was connected to the incubation channel and detection channels with tapered holes with average diameters of approximately 500 um, and a depth of about 0.86 mm.

The width, depth, and length of the incubation channel were sized to contain a sample volume of at least 12 uL (but less than or equal to about 24 uL). The ratio of channel depth to channel width (0.7) was designed to be close to but less than 1. As the ratio of depth to width increases, the parts become more difficult to manufacture by injection molding. As the ratio of depth to width becomes very small, the channels may be more prone to collapse. For example, the channel cover may flex into the full depth of the channel. A trapezoidal cross section was selected because the shape provides a draft angle making it easier to eject the part from a mold.

After filling the sample collector with the sample, the user connected the sample collector to the microfluidic device. The sample collector formed a bridge between the downstream microchannels in a first cassette which make up the incubation channel, detection channel/zone, and waste feature, and the upstream microchannels in a second cassette which stored liquid reagents necessary for an assay. Plugs of reagents including amplification reagents (e.g., silver nitrate, a reducing agent) and wash plugs were stored in a channel of the second cassette and separated by an immiscible fluid. The user inserted the microfluidic device into the analyzer, and then entered the patient information into the analyzer via a touchscreen, and finally initiated the test. All assay steps were performed automatically with no user intervention as follows.

To introduce the sample, the analyzer applied a vacuum to the microfluidic device, pulling the sample mixture from the sample collector into the incubation channel in the microfluidic device. Downstream of the incubation channel was a detection channel of a detection zone of the microfluidic device. Once the sample mixture entered into a part (but not all) of this zone/channel (which had a maximum width of 120 um and a depth of 50 um), and the presence of the sample was detected optically via a reduction in light transmission by the analyzer, the analyzer stopped the sample flow. This was accomplished by releasing the vacuum that was applied to the microfluidic device.

Sample incubation occurred while the fluid flow was stopped for five minutes. During this time, vit-D bound to VDBP in the sample was released, aided by pH, release agent, and temperature. The temperature in the region of the analyzer adjacent to the incubation channel was controlled. The vit-D in the sample mixture bound to the gold-labeled anti-vit-D antibodies to form labeled antigen-antibody complexes.

After five minutes, the fluid flow was resumed by re-application of the vacuum.

The unbound material was removed by flowing wash plugs that were stored upstream in the microfluidic device (e.g., upstream of the sample collector) through the sample collector and through the incubation channel, and detection channel of the detection zone. A sequence of automatic washing steps removed sample components and reagents which were not specifically bound to vit-D in the analysis regions of the detection zone. Amplification and detection of the signal was performed by flowing a silver amplification reagent following the wash plugs through the detection zone. The amplification agent reacted with the available nano-gold particles. The reaction resulted in the deposition of a visible silver metallic film within the analysis region, which blocked the transmission of light.

All reagents and the sample were contained by the waste zone within the microfluidic device. Upon completion of the assay, the user discarded the microfluidic device in a biohazard container.

Released vitamin D binds to a fraction of the gold-labeled anti-vitamin D antibodies during the release step; the remainder of the gold-labeled antibodies are unbound at this point and later bind to the immobilized vitamin D in the detection zone. Thus, the concentration of vitamin D in the initial sample is inversely proportional to the measured signal level of the immobilized gold-labeled anti-vitamin D antibodies in the detection zone.

Figure 14:
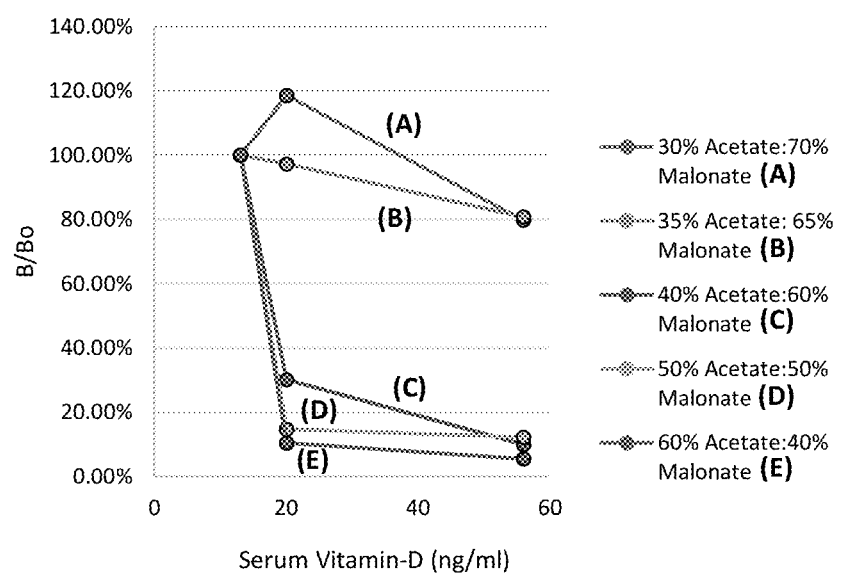
FIG. 14 shows a plot of optical readout versus time for determining binding of vitamin D using buffers with different malonate:acetate ratios according to one set of embodiments.

The signals from samples diluted into each buffer were compared. FIG. 14 shows a chart comparing the signal levels from samples diluted into each different buffer at each vitamin D level. This chart shows that acetate-malonate buffers containing at least 40% acetate are effective buffers for vitamin D release for serum samples.

Example 4

This example describes release of vitamin D from its binding protein and performance of an assay in a fluidic device comprising an incubation channel and a detection zone.

Vitamin D serum samples spanning the range of 10-120 ng/mL were obtained from New York Biologics, Southampton, N.Y. In order to release vitamin D from its binding protein (vitamin D binding protein) and/or from other binding entities (e.g., albumin), serum was diluted 1:10 in acetate buffer, pH adjusted to 5.5 with acetic acid, which included 0.4% of the detergent FS50 and 50 ng/mL gold-labeled anti-vitamin D antibody. Six serum samples with varying vitamin D levels were prepared: two each at approximately 10, 40 and 80 ng/mL. 12.5 µL of the serum samples were each transferred to microfluidic cassettes which contained detection zones coated with vitamin D covalently coupled to bovine serum albumin. The microfluidic cassettes used were Sangia™ cassettes, similar to the one shown in FIG. 5C, and as described herein and generally in U.S. Patent Publication No. 2011/0256551, filed Apr. 15, 2011, entitled "Systems and Devices for Analysis of Samples," and International Patent Publication No. WO2005/066613 (International Patent Application Serial No. PCT/US2004/043585), filed Dec. 20, 2004 and entitled "Assay Device and Method," which are incorporated herein by reference. The cassette was inserted into an analyzer (e.g., Claros® 1 Analyzer) for exposing the sample to appropriate temperature.

The procedure described in Example 3 for conducting the analysis using the cassette was followed, except in this example, for each vitamin D level, one of the serum samples was heated to 45° C. for 5 minutes, and one serum sample was heated to 50° C. for 5 minutes (e.g., in the incubation channel). The analyzer then performed the remaining assay step to determine the amount of vitamin D in the sample.

Released vitamin D binds to a fraction of the gold-labeled anti-vitamin D antibodies during the release step; the remainder of the gold-labeled antibodies are unbound at this point and later bind to the immobilized vitamin D in the detection zone. Thus, the concentration of vitamin D in the initial sample is inversely proportional to the measured signal level of the immobilized gold-labeled anti-vitamin D antibodies in the detection zone.

Figure 15:
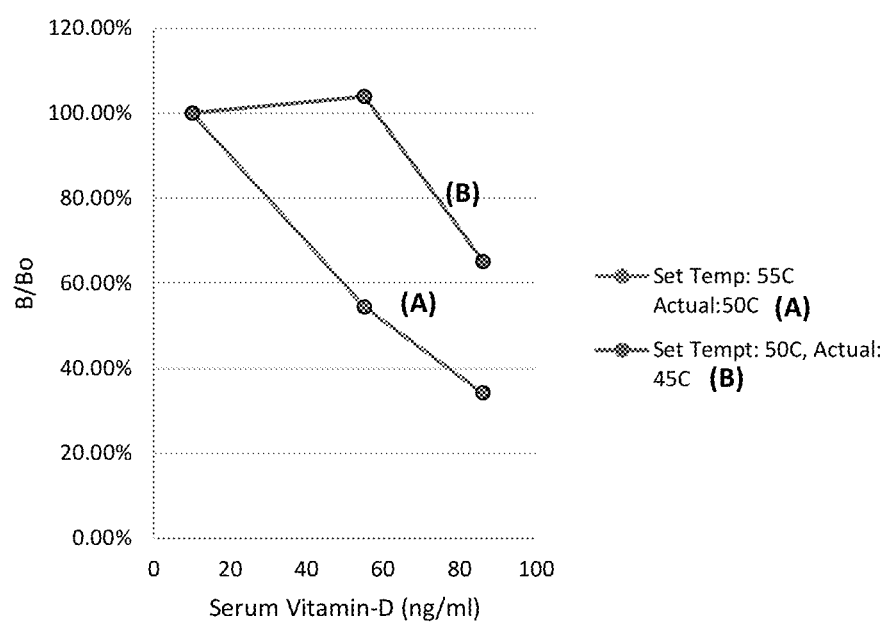
FIG. 15 shows a plot of optical readout versus time for determining binding of vitamin D after thermal treatment at different temperatures according to one set of embodiments.

Signal responses of vitamin D released after 5 minutes of incubation at 45° C. (wherein the actual temperature of the solution was 45° C., data labelled "B" in FIG. 15) was compared to that of vitamin D released after 5 minutes at 50° C. (wherein the actual temperature of the solution was 50° C., data labelled "A" in FIG. 15) for serum samples at each vitamin D level. FIG. 15 shows a chart comparing the measured signal levels for each incubation condition. Samples incubated for 5 minutes at 50° C. showed significant signal reduction in the detection zone for 60 ng/mL and 90 ng/mL samples, indicating the release of a significant amount of vitamin D during thermal treatment. Samples incubated for 5 minutes at 45° C. showed a comparatively smaller reduction in signal level, indicating the release of less vitamin D during thermal treatment.

Figure 16:
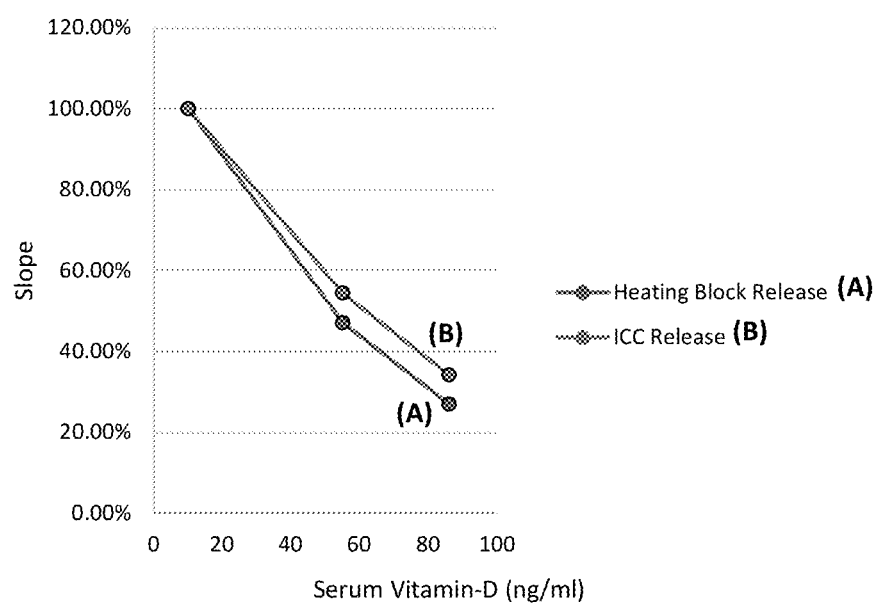
FIG. 16 shows a plot of optical readout versus time for determining binding of vitamin D after thermal treatment using different heating methods according to one set of embodiments.

FIG. 16 shows a chart comparing the measured signal levels for serum samples incubated for 5 minutes at 50° C. contained in an Eppendorf tube on a heating block (labelled "Heating Block Release" in FIG. 16) compared to those heated in the microfluidic cassettes (labelled "ICC Release" in FIG. 16). The measured signal levels were similar for both sets of samples, indicating good agreement across differing volumes of sample and heating procedures.

Example 5

This example describes release of vitamin D from its binding protein and performance of an assay in a fluidic device comprising an incubation channel and a detection zone. The method involved reducing the temperature of the sample after the incubation step.

The microfluidic cassettes used were Sangia™ cassettes, similar to the one shown in FIG. 5C, and as described herein and generally in U.S. Patent Publication No. 2011/0256551, filed Apr. 15, 2011, entitled "Systems and Devices for Analysis of Samples," and International Patent Publication No. WO2005/066613 (International Patent Application Serial No. PCT/US2004/043585), filed Dec. 20, 2004 and entitled "Assay Device and Method," which are incorporated herein by reference. The cassette was inserted into an analyzer (e.g., Claros® 1 Analyzer) for exposing the sample to appropriate temperature.

The procedure described in Example 3 for conducting the analysis using the cassette was followed, except in this example, the incubation temperature was 55 deg C. and the temperature of the sample was reduced after the incubation step.

It was observed that in some experiments without the temperature reduction step, the efficacy of the release of Vitamin D from the VDBP was favorable at a temperature of 50 deg C. (inside the incubation channel) but the flow of the sample after incubation through the detection channels was compromised, resulting in an elevated rate of clogging (or, a very slow flow rate that resulted in incomplete flow for the sample through the detection zone after 15 minutes). Reducing the temperature of the sample and microchannels to a temperature of less than 50 deg C. after the incubation step improved significantly the flow of sample, e.g., as shown in Table 2.

TABLE 2

| Sample matrix | Temperature during incubation | Temperature during flow through the detection channels | Rate of successful flow of sample through the detection channels |
|---|---|---|---|
| Whole blood | 55 deg C. | 55 deg C. | 20% (n = 20) |
|  |  | 37 deg C. | 77% (n = 26) |
| Undiluted plasma | 55 deg C. | 55 deg C. | 50% (n = 4) |
|  |  | 37 deg C. | 100% (n = 2) |

The experiments performed in the analyzer with the heating element set at 55 deg C. were incompatible with an adhesive-coated lid: the adhesive was found to flow inside the microchannels and interfere with the flow of sample through the microchannels. Instead, in some experiments, the microfluidic channels were covered with an adhesive-free lid using solvent bonding.

Example 6

This example describes a vitamin D assay for measuring the amount of bioavailable vitamin D in a sample. In this example, bioavailable vitamin D is measured in a fluidic device comprising a detection zone.

The fluidic device may include one or more release agents stored therein (e.g., in a sample collection device that may be sealed or unsealed prior to use). The one or more release reagents may have a primary function of releasing most vitamin D from albumin (and/or other proteins besides the vitamin D binding protein). The release agent was combined with a preparation containing detergents and buffer, such as pH 5.5 100 mM buffer (50% acetate-50% malonate) with 0.8% of the detergent FS50. Other detergents may optionally be included such as perfluorinated acids including perfluorohexanioc acid, perfluoroheptanoic acid or perfluorooctanoic acid. The release agents or preparation also included a labeled anti-vitamin D antibody (for example 50 ng/mL gold-labeled anti-vitamin D antibody). The preparation including release agent(s) may be dried or lyophilized in a portion of the device, such as in the sample collection device.

The assay can be performed using freshly obtained whole blood samples, either capillary whole blood or venous blood anti-coagulated with EDTA, citrate or heparin. In some instances venous blood drawn into neat tubes (i.e., tubes without any anti-coagulation reagents) may be used as well. The blood is introduced inside the sample collection device, where it reconstitutes the release reagent. Upon flowing inside the sample collection device, the whole blood reconstitutes the release reagent and the release reaction is initiated. After attachment of the collection device to the fluidic device, the fluidic device is inserted into an analyzer (e.g., Claros® 1 Analyzer) for determining the amount of vitamin D in the sample.

The analyzer applies a vacuum at the outlet of the fluidic system (downstream of the detection zone), resulting in the flow of the sample/release reagent mixture inside the fluidic device. Optionally, the mixture may be incubated in a segment of a channel (e.g., microchannel) located upstream of the detection zone at a fixed temperature ranging between 37 and 45° C. for five minutes (or for another amount of time, suitable values for which range from less than a second to more than 20 minutes). The release formulation and temperature during incubation can be chosen to achieve incubation times which are as short as possible in order to reduce the time that passes before results are obtained.

Released vitamin D binds to a fraction of the gold-labeled anti-vitamin D antibodies during the release step; the remainder of the gold-labeled antibodies are unbound at this point and later bind to the immobilized vitamin D (exogenous vitamin D) in the detection zone. Thus, the concentration of vitamin D in the initial sample is inversely proportional to the measured signal level of the immobilized gold-labeled anti-vitamin D antibodies in the detection zone. In some embodiments, the performance of the assay may be improved by using antibody fragments (such as Fab), such that a single binding site for vitamin D is present on each fragment. This configuration may be an improvement over the use of full antibodies (for example, IgG has 2 binding sites for the epitope), which can bind to a released Vitamin D at one of its binding sites, while binding to the solid phase through its second binding site.

After the optional on-chip incubation, the sample/reagent release mixture flows through the detection zone, followed by wash fluids and a silver enhancement reagent, consistent with the silver amplified nano-gold immunoassay (SANGIA) technology, and the signal is measured by monitoring changes in the optical density measured through the detection zone. The reagents and the sample are contained by the waste zone within the fluidic device. Upon completion of the assay, the user may discard the fluidic device in a biohazard container.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method, comprising:
   introducing a sample into a fluidic device comprising at least one microfluidic channel, wherein the sample comprises vitamin D bound to a vitamin D binding protein;
   flowing, at a first flow rate, at least a portion of the sample into a microfluidic incubation channel;
   reducing the flow rate of the sample to a second flow rate after a leading edge of the sample enters the incubation channel but prior to the leading edge reaching an exit of the incubation channel, wherein the leading edge is a sample/gas interface, wherein the second flow rate is less than the first flow rate and/or is zero to allow incubation of the sample in the incubation channel, and wherein the incubation occurs for at least one minute at a temperature of at least 30° C.;
   exposing the sample to a release agent;
   releasing the vitamin D from the vitamin D binding protein;
   modulating the flow rate of the sample to a third flow rate which is greater than the second flow rate; and
   determining an amount of vitamin D in the sample.

2. A method as in claim 1, wherein the fluidic device contains a buffer having a pH of at least 5 and less than or equal to 9.

3. A method as in claim 2, wherein the buffer comprises a citrate buffer, an acetate buffer, a malonate buffer, a tris buffer, or a combination thereof.

4. A method as in claim 2, wherein the buffer has an acidic pH.

5. A method as in claim 2, wherein the buffer has a concentration of between 50 mM and 150 mM.

6. A method as in claim 1, wherein the release agent comprises a detergent.

7. A method as in claim 6, wherein the detergent comprises at least one of perfluorohexanoic acid, FS50, FS51, and Empigen BB.

8. A method as in claim 6, wherein the detergent comprises at least one of 1-5% perfluorohexanoic acid, 0.4-0.8% FS50, 0.4% FS51, and 0.4% Empigen BB.

9. A method as in claim 1, wherein the fluidic device contains in a channel a labeled molecule, wherein the labelled molecule is a monoclonal or polyclonal antibody that binds with vitamin D.

10. A method as in claim 1, wherein the fluidic device contains, in a channel, a labeled molecule, wherein the labelled molecule is Vitamin D that binds with anti-Vitamin D antibody and/or fragments thereof.

11. A method as in claim 1, wherein the fluidic device contains, in a channel, a labeled molecule, and wherein the labeled molecule is a metal nanoparticle-labeled anti-vitamin D antibody, a metal nanoparticle-labeled anti-vitamin D antibody fragment, a gold-labeled anti-vitamin D antibody, or a gold-labeled anti-vitamin D antibody fragment.

12. A method as in claim 1, wherein the fluidic device contains, in a channel, a labeled molecule, and wherein the labeled molecule is a metal nanoparticle-labeled Vitamin D, or a gold-labeled Vitamin D.

13. A method as in claim 1 comprising diluting the sample between 0 vol % to 90 vol %.

14. A method as in claim 1, wherein the sample comprises whole blood.

15. A method as in claim 1, wherein the sample is serum or plasma.

16. A method as in claim 1, wherein the release agent is a dried or lyophilized solid derived from a liquid solution.

17. A method as in claim 1, wherein the release agent is a liquid solution.

18. A method as in claim 17, wherein the liquid solution further contains a transfer molecule.

19. A method as in claim 18, wherein the transfer molecule is a member of the beta-cyclodextrin family.

20. A method as in claim 18, wherein the transfer molecule is methyl-beta-cyclodextrin, or comprises an acetyl-, succinyl-(2-hydroxypropyl)-, 2-hydroxypropyl-, carboxymethyl-, sulfate, 2-hydroxyethyl, succinyl-, and/or butyl- group.

21. A method as in claim 1, wherein the release agent comprises a carboxyl or amine oxide head group and a fluorinated or non-fluorinated carbon chain.

22. A method as in claim 1, wherein the dried or lyophilized release agent contained in the fluidic channel is reconstituted by the sample.

23. A method as in claim 1, wherein the release agent is contained in a first fluid and the anti-vit-D antibody and/or fragments thereof is contained in a second fluid or the Vitamin D is contained in a second fluid, and wherein the second fluid is separated from the first fluid by a third fluid that is immiscible with the first and second fluids.

24. A method as in claim 1 comprising heating the sample to at least about 50° C. for at least 5 minutes and less than or equal to 15 minutes.

25. A method as in claim 1, wherein the steps of exposing the sample to a release agent and releasing the vitamin D from the vitamin D binding protein occur before or during the step of flowing, at the first flow rate, at least a portion of the sample into an incubation channel.

26. A method as in claim 1, wherein the steps of exposing the sample to a release agent and releasing the vitamin D from the vitamin D binding protein occur after the step of flowing, at the first flow rate, at least a portion of the sample into an incubation channel.

27. A method as in claim 1, further comprising binding the released vitamin D with a labelled anti-vit-D antibody, wherein a plurality of the labelled anti-vit-D antibodies are bound to released vitamin D or are bound to vitamin D immobilized on a surface of the at least one microfluidic channel, the method further comprising flowing a wash plug comprising a rinse solution past the plurality of labelled anti-vit-D antibodies, wherein the wash plug is separated from the sample by a fluid that is immiscible with both the sample and the rinse solution.

28. A method as in claim 1, further comprising binding the released vitamin D and/or labelled vitamin D with a plurality of anti-vit-D antibodies immobilized on a surface of the at least one microchannel, the method further comprising flowing a wash plug comprising a rinse solution past the plurality of anti-vit-D antibodies immobilized on the surface of the at least one microchannel, wherein the wash plug is separated from the sample by a fluid that is immiscible with both the sample and the rinse solution.

29. A method as in claim 1, wherein the step of exposing the sample to the release agent occurs before or during the step of introducing the sample into the fluidic device.

30. A method as in claim 1, wherein the step of exposing the sample to the release agent occurs after the step of introducing the sample into the fluidic device.

31. A method as in claim 1, wherein the method further comprises:
exposing the sample to a gold-labeled molecule; and
exposing the gold-labeled molecule to a reagent after the step of exposing the sample to the gold-labeled molecule,
wherein the step of determining the amount of vitamin D in the sample is based at least in part on a signal generated by a chemical reaction between the gold-labeled molecule with the reagent.

32. A method as in claim 31, wherein the chemical reaction between the gold-labeled molecule and the reagent occurs in a microfluidic channel.

33. A method, comprising:
exposing a sample comprising vitamin D bound to a vitamin D binding protein to a release agent;
releasing the vitamin D from the vitamin D binding protein;
introducing the sample subjected to the exposing step into a fluidic device comprising at least one microfluidic channel;
flowing, at a first flow rate, at least a portion of the sample into a microfluidic incubation channel;
reducing the flow rate of the sample to a second flow rate after a leading edge of the sample enters the incubation channel but prior to the leading edge reaching an exit of the incubation channel, wherein the leading edge is a sample/gas interface, wherein the second flow rate is less than the first flow rate and/or is zero to allow incubation of the sample in the incubation channel, and wherein the incubation occurs for at least one minute at a temperature of at least 30° C.;
modulating the flow rate of the sample to a third flow rate which is greater than the second flow rate; and
determining an amount of vitamin D in the sample.

* * * * *